US012564547B2

(12) United States Patent
Boppana et al.

(10) Patent No.: US 12,564,547 B2
(45) Date of Patent: Mar. 3, 2026

(54) COMPOSITIONS, FORMULATIONS, AND METHODS FOR SKIN TREATMENT

(71) Applicant: Oddity Labs, LLC, New York, NY (US)

(72) Inventors: Avinash Boppana, Boston, MA (US); Kongyu Zhang, Boston, MA (US); Evan Zhao, Woburn, MA (US); Connor Wilson Coley, Cambridge, MA (US); Elizabeth Lee, San Diego, CA (US); Victoria Shin-wei Fu, Monrovia, CA (US); Gloria Lu, Pasadena, CA (US)

(73) Assignee: ODDITY LABS, LLC, New York, NY (US)

( * ) Notice: Subject to any disclaimer, the term of this patent is extended or adjusted under 35 U.S.C. 154(b) by 538 days.

(21) Appl. No.: 18/094,001

(22) Filed: Jan. 6, 2023

(65) Prior Publication Data

US 2023/0240960 A1 Aug. 3, 2023

Related U.S. Application Data

(63) Continuation of application No. PCT/US2023/010270, filed on Jan. 6, 2023.

(60) Provisional application No. 63/297,413, filed on Jan. 7, 2022.

(51) Int. Cl.

*A61K 8/49* (2006.01)
*A61Q 19/00* (2006.01)
*A61Q 19/08* (2006.01)

(52) U.S. Cl.

CPC .......... *A61K 8/4953* (2013.01); *A61Q 19/007* (2013.01); *A61Q 19/08* (2013.01)

(58) Field of Classification Search

CPC .................................................... A61K 8/4953
See application file for complete search history.

(56) References Cited

U.S. PATENT DOCUMENTS

| | | | |
|---|---|---|---|
| 6,407,116 | B1 | 6/2002 | Kajino et al. |
| 2011/0213033 | A1 | 9/2011 | Tokuyama et al. |
| 2013/0225612 | A1 | 8/2013 | Lambeth et al. |
| 2020/0222295 | A1 | 7/2020 | Hood et al. |
| 2021/0109111 | A1 | 4/2021 | Bourgoin-Voillard et al. |

FOREIGN PATENT DOCUMENTS

| | | | |
|---|---|---|---|
| WO | WO-2023133240 | A1 | 7/2023 |

OTHER PUBLICATIONS

Can you prevent psoriasis? [online] retrieved on Jun. 27, 2025; URL: https://www.healthline.com/health/psoriasis-prevention.*
PCT/US2023/010270 International Preliminary Report on Patentability dated Jun. 20, 2024.
International search report with written opinion dated May 23, 2023 for PCT/US2023/010270.

* cited by examiner

*Primary Examiner* — Shawquia Jackson
(74) *Attorney, Agent, or Firm* — Mark S. Cohen; PEARL COHEN ZEDEK LATZER BARATZ LLP

(57) ABSTRACT

Compositions and formulations for skin treatment are provided herein. Methods for skin treatment, such as methods for preventing or treating skin conditions, disorder, or disease are also provided herein. The methods may prevent or reduce wrinkle(s) or fine line(s), increase skin tightness, or moisturize skin.

19 Claims, 15 Drawing Sheets

COMPOSITIONS, FORMULATIONS, AND METHODS FOR SKIN TREATMENT

CROSS REFERENCE

This application a continuation of International Patent Application No. PCT/US2023/10270, filed Jan. 6, 2023, which claims the benefit of U.S. Provisional Patent Application No. 63/297,413, filed Jan. 7, 2022, which is incorporated by reference herein in its entirety.

SUMMARY

A skin condition, disorder, or disease (whether or not a diagnosis of the skin condition, disorder, or disease has been made) is a common problem which is, for example, naturally occurring or chemically promoted through the long-term use of certain chemicals (e.g., commercial products or therapeutic drugs).

The disclosure provides a method for preventing or treating a skin condition, disorder, or disease (whether or not a diagnosis of the skin condition, disorder, or disease has been made), the method comprising administering to a subject in need thereof a composition comprising a compound having a structure of a compound of Formula (I), (II), (III), (IV), (V), (VI), or (VII). The compounds or salts thereof may be selected from those forth in Tables 1-8, or any subset thereof.

Provided herein is a method for preventing or treating a skin condition, disorder, or disease. In some embodiments, the method comprises administering to a subject in need thereof a composition comprising a compound having a structure of Formula (V):

(V)

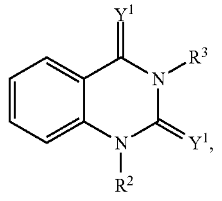

or salts thereof, wherein:

- $Y^1$ is O, S or $NR^1$, wherein $R^1$ is H, alkyl, or haloalkyl;
- $R^2$ is selected from H, alkyl, haloalkyl, alkenyl, haloalkenyl, aryl, and aralkyl; and
- $R^3$ is selected from H, alkyl, haloalkyl, $—(CH_2)_{m1}—OR^{a1}$, $—(CH_2)_{m2}—O—(CH_2)_{m3}—OR^{a2}$, $—(CH_2)_{m4}—NR^{b1}R^{b2}$, $(CH_2)_{m5}—C(O)OR^c$, wherein:
- $R^{a1}$, $R^{a2}$, $R^{b1}$, $R^{b2}$, and $R^c$ are each independently selected from H, alkyl, and haloalkyl; and
- m1, m2, m3, m4, and m5 are each independently selected from 1, 2, 3, and 4.

In some embodiments, $Y^1$ is O or S. In some embodiments, $Y^1$ is O. In some embodiments, $R^{a1}$, $R^{a2}$, $R^{b1}$, $R^{b2}$, and $R^c$ are each independently $C_1$-$C_6$ alkyl, such as $C_1$-$C_3$ alkyl. In some embodiments, $R^{a1}$, $R^{a2}$, $R^{b1}$, $R^{b2}$, and $R^c$ are each independently $C_1$ alkyl or $C_2$ alkyl. In some embodiments, m1, m2, m3, and m4 are each independently 2 or 3. In some embodiments, m5 is 1. In some embodiments, $R^2$ is H.

In some embodiments, the compound of Formula (V) or the salt thereof is selected from:

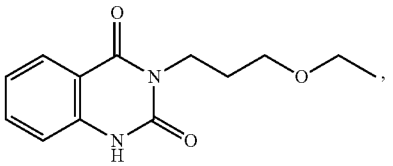

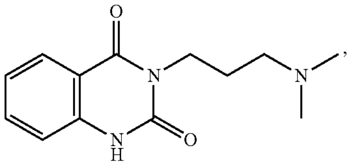

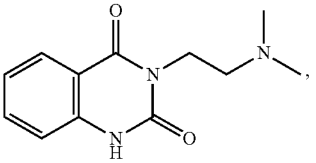

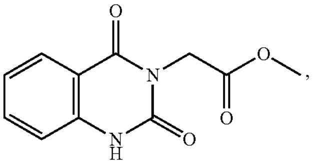

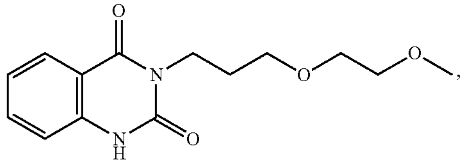

and salts of any one thereof.

Provided herein is a method for preventing or treating a skin condition, disorder, or disease, the method comprising administering to a subject in need thereof a composition comprising a compound having a structure of Formula (IV):

(IV)

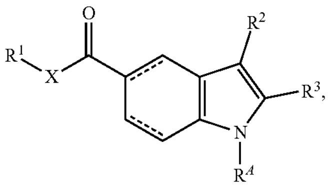

or salts thereof, wherein:

- $R^1$ is selected from alkyl, or heterocycloalkyl, wherein the alkyl or heterocycloalkyl of $R^1$ is optionally substituted with one or more substituents independently selected from heterocycloalkyl, $—C(O)NR^{x1}R^{x2}$, alkoxy, $—(C_1$-$C_3$ alkylene)-$C(O)OR^{y1}$, $—C(O)OR^{y2}$, and $—OR^z$; wherein:
- $R^{x1}$, $R^{x2}$, $R^{y1}$, $R^{y2}$, and $R^z$ are each independently selected from H, alkyl, and haloalkyl;
- $R^A$ is H or alkyl;
- X is —O—, —S—, or $—NR^B—$; $R^B$ is H, alkyl, or haloalkyl;
- $R^2$ and $R^3$ are each independently selected from H, linear $C_1$-$C_6$ alkyl, branched $C_1$-$C_6$ alkyl; or alternatively, $R^2$ and $R^3$ together with the atoms to which they are attached to form $C_4$-$C_6$ cycloalkyl or aryl, wherein the cycloalkyl or aryl is optionally substituted with one or more substituents independently selected from halogen, alkyl, and haloalkyl; and wherein the dotted lines indicate the presence of a single or double bond.

In some embodiments, the compound of Formula (IV) has a structural formula:

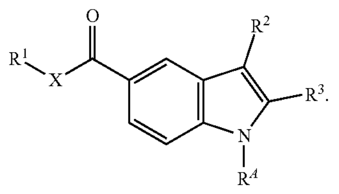

In some embodiments, the compound of Formula (IV) has a structural formula:

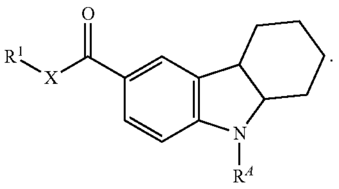

In some embodiments, the compound of Formula (IV) has a structural formula:

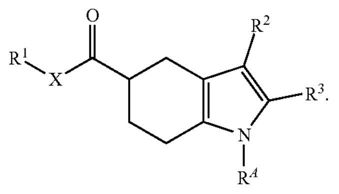

In some embodiments, the compound of Formula (IV) has a structural formula:

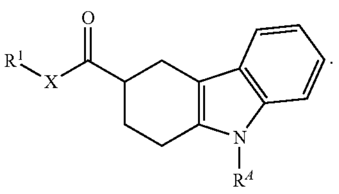

In some embodiments, $R^2$ and $R^3$ are each independently selected from $C_1$-$C_6$ alkyl.

In some embodiments, $R^2$ and $R^3$ together with the atoms to which they are attached to form a $C_4$-$C_6$ cycloalkyl, optionally substituted with one or more substituents independently selected from halogen, alkyl, and haloalkyl.

In some embodiments, $R^2$ and $R^3$ together with the atoms to which they are attached to form a cyclohexyl, optionally substituted with one or more substituents independently selected from halogen, alkyl, and haloalkyl.

In some embodiments, $R^2$ and $R^3$ together with the atoms to which they are attached to form an $C_{5-8}$ aryl, optionally substituted with one or more substituents independently selected from halogen, alkyl, and haloalkyl.

In some embodiments, $R^2$ and $R^3$ together with the atoms to which they are attached to form a phenyl, optionally substituted with one or more substituents independently selected from halogen, alkyl, and haloalkyl.

In some embodiments, $R^A$ is H.

In some embodiments, X is —O—. In some embodiments, X is —$NR^B$—, optionally wherein $R^B$ is H.

In some embodiments, $R^1$ is selected from: $-(CH_2)_aC(O)OH$, $-(CH_2)_aOCH_3$, $-(CH_2)_aCH(OH)CH_3$,

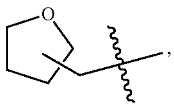,
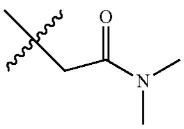, and
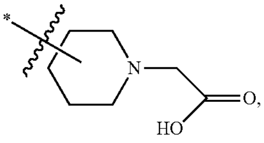

wherein: a is 0, 1, 2, or 3.

In some embodiments, $R^1$ is selected from: $-CH_2C(O)OH$, $-(CH_2)_2OCH_3$, $-CH_2CH(OH)CH_3$,

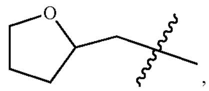,
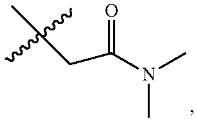, and
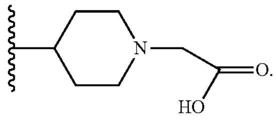

In some embodiments, $R^{x1}$ and $R^{x2}$ are each independently $C_1$-$C_6$ alkyl.

In some embodiments, $R^{x1}$ and $R^{x2}$ are each independently $C_1$-$C_3$ alkyl.

In some embodiments, $R^{y1}$ is H.

In some embodiments, $R^{y2}$ is H.

In some embodiments, $R^z$ is H.

In some embodiments, the compound of Formula (IV) or the salt thereof is selected from:

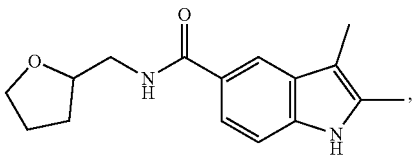,

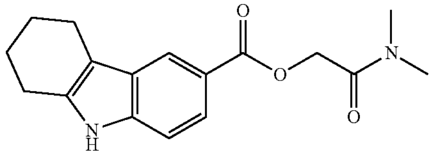,

-continued

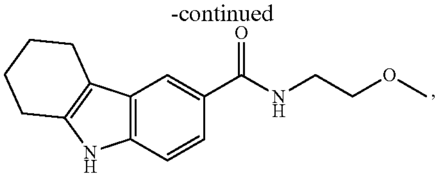

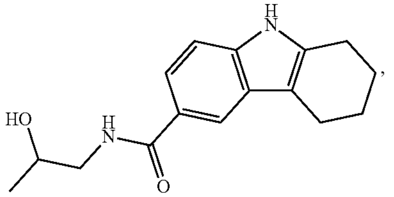

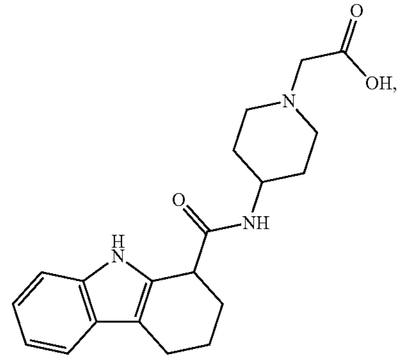

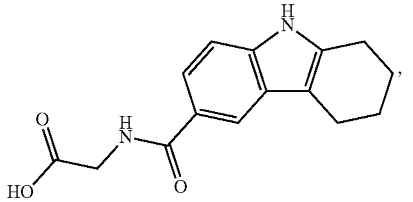

and salts of any one thereof.

Provided herein is a method for preventing or treating a skin condition, disorder, or disease, the method comprising administering to a subject in need thereof a composition comprising a compound having a structure of Formula (VII):

(VII)

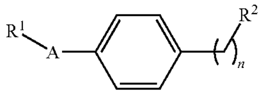

or salts thereof, wherein:

A is selected from O, NH, S;

$R^1$ is selected from hydrogen, $C_{1-6}$ alkyl, $C_{1-6}$ haloalkyl, $C_{2-6}$ alkenyl, $C_{2-6}$ alkynyl, $C_{2-10}$ alkynyl, $C_{3-12}$ carbocycle, and 3- to 12-membered heterocycle;

$R^2$ is selected from 6- to 10-membered heterocycle, wherein the 6- to 10-membered heterocycle is optionally substituted with one or more substituents independently selected from halogen, $C_{1-6}$ alkyl, $C_{2-6}$ alkenyl, and $C_{2-6}$ alkynyl, $—OR^{11}$, $—SR^{11}$, $—NO_2$, $=O$, $=NH$, $—CN$, $—C(O)R^{11}$, $—C(O)OR^{11}$, $—OC(O)R^{11}$, $—OC(O)N(R^{11})_2$, $—NR^{11}S(O)_2R^{11}$, $—C(O)N(R^{11})_2$, $—N(R^{11})C(O)R^{11}$, $—N(R^{11})C(O)N(R^{11})_2$, $—N(R^{11})C(O)OR^{11}$, $—S(O)_2(R^{11})$, $—S(O)_2N(R^{11})_2$, $C_{1-10}$ alkyl, $C_3$-$C_{12}$ carbocycle and 5- to 12-membered heterocycle;

n is selected from 1, 2, 3, 4, 5, and 6;

each $R^{11}$ is independently selected at each occurrence from hydrogen; $C_{1-6}$ alkyl, $C_{2-6}$ alkenyl, $C_{2-6}$ alkynyl, and $C_{3-12}$ carbocycle, each of which is optionally substituted with one or more substituents selected from 3- to 6-membered heterocycle.

In some embodiments, A is O.

In some embodiments, $R^1$ is $C_{1-6}$ alkyl. In some embodiments, $R^1$ is $C_1$ alkyl.

In some embodiments, n is selected 1 and 3. In some embodiments, n is 1. In some embodiments, n is 3.

In some embodiments, the 6- to 10-membered heterocycle of $R^2$ is selected from pyran, pyridine, piperidine, imidazole, thiazole, dioxane, morpholine, pyrimidine, benzimidazole, piperazine, thiadiazine, oxepane, thiepine, azocine, indole, isoindole, indolizine, quinoline, isoquinoline, purine, cabazole, and dibesofuran.

In some embodiments, $R^2$ is selected from benzimidazole and piperazine. In some embodiments, $R^2$ is

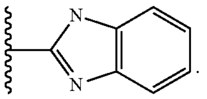 [SMILES: *c1nc2ccccc2[nH]1]

In some embodiments, $R^2$ is piperazine. In some embodiments, piperazine is optionally substituted with one or more substituents independently selected from with $=O$ and $—C(O)R^{11}$. In some embodiments, $R^{11}$ is $C_{1-6}$ alkyl substituted with one or more substituents selected from 3- to 6-membered heterocycle. In some embodiments, $C_{1-6}$ alkyl is $C_1$ alkyl or $C_2$ alkyl. In some embodiments, the 3- to 6-membered heterocycle is

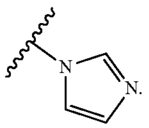 [SMILES: *n1ccnc1]

In some embodiments, each $R^2$ is selected from:

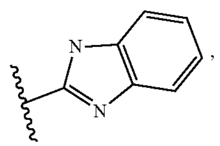

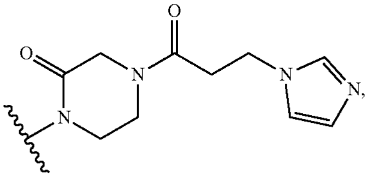

and

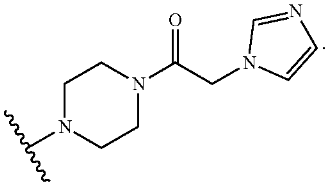

In some embodiments, the compound of Formula (VII) or the salt thereof is selected from:

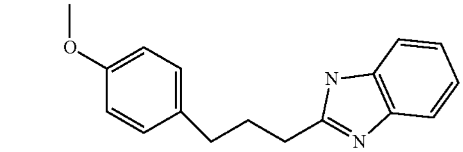,

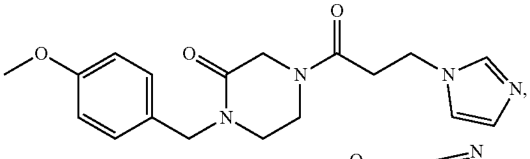,

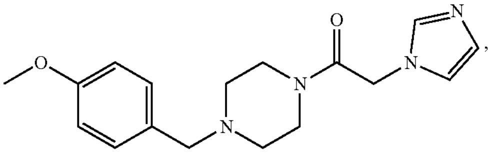, and salts of any one thereof.

Provided herein is also a method for preventing or treating a skin condition, disorder, or disease, the method comprising administering to a subject in need thereof a composition comprising a compound having a structure of Formula (III):

(III)

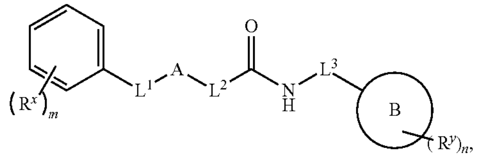

or a salt thereof wherein:

- $L^1$, $L^2$ and $L^3$ are each independently selected from bond, linear $C_{1-6}$ alkyl, or branched $C_{1-6}$ alkyl;
- A is N-amido, —NH—C(O)—, or —C(O)—NH—;
- Ring B is selected from $C_{4-6}$ cycloalkyl, 5- or 6-membered heterocyclyl, $C_{5-8}$ aryl, heteroaryl, and aralkyl;
- $R^x$ and $R^y$ are each independently selected from halogen, alkyl, haloalkyl, alkenyl, haloalkenyl, hydroxyl, alkoxy, haloalkoxy, nitro, —$NH_2$, alkylamino, dialkylamino, and haloalkylamino;
- m is 0, 1, or 2; and
- n is 0 or 1.

In some embodiments, Ring B is selected from $C_{5-8}$ aryl, heteroaryl, and aralkyl. In some embodiments, Ring B is selected from $C_{5-8}$ aryl and heteroaryl. In some embodiments, $C_{5-8}$ aryl is phenyl and heteroaryl is imidazolyl.

In some embodiments, $R^x$ is $C_1$-$C_3$ alkoxy. In some embodiments, $R^x$ is —$OCH_3$.

In some embodiments, Ring B is

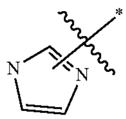 or 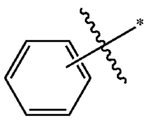.

In some embodiments, Ring B is

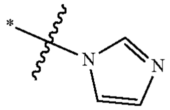 or 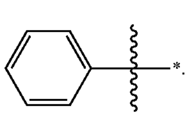.

In some embodiments, m is 0 or 1. In some embodiments, n is 0.

In some embodiments, the compound of Formula (III) or the salt thereof is selected from:

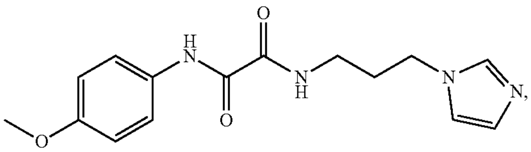,

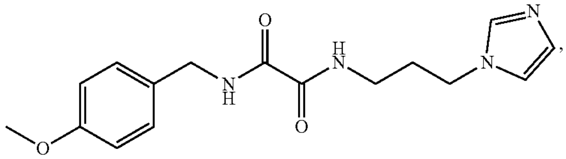,

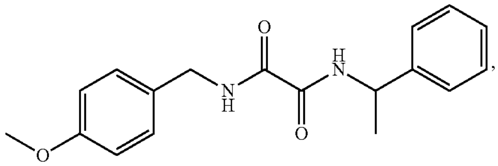,

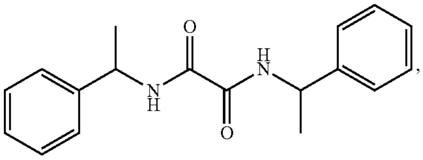,

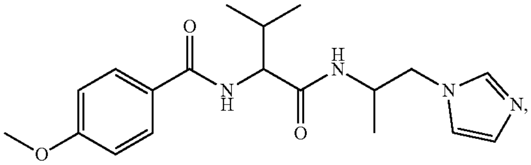, and salts of any one thereof.

Provided herein is a method for preventing or treating a skin condition, disorder, or disease, the method comprising administering to a subject in need thereof a composition comprising a compound having a structure of Formula (II):

(II)

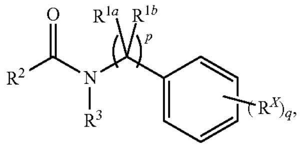

or a salt thereof, wherein:

- $R^{1a}$ and $R^{1b}$ are each independently selected from H, alkyl, haloalkyl, alkenyl, haloalkenyl, $C_{5-8}$ aryl, and aralkyl;

$R^x$ is each independently selected from halogen, alkyl, haloalkyl, alkenyl, haloalkenyl, —OH, alkoxy, haloalkoxy, nitro, —$NH_2$, alkylamino, dialkylamino, and haloalkylamino;

p is 1, 2, or 3;

q is 0, 1, or 2;

$R^2$ is selected from H, alkyl, alkenyl, haloalkyl, haloalkenyl, nitro, —$NH_2$, alkylamino, dialkylamino, alkyl-dialkylamino, and haloalkylamino; and $R^3$ is selected from H, alkyl, and haloalkyl.

In some embodiments, $R^{1a}$ and $R^{1b}$ are independently selected from H and $C_{1-6}$ alkyl. In some embodiments, $R^{1a}$ and $R^{1b}$ are H.

In some embodiments, $R^x$ is $C_1$ to $C_6$ alkoxy. In some embodiments, $R^x$ is —$OCH_3$.

In some embodiments, q is 0 or 1. In some embodiments, p is 1.

In some embodiments, $R^2$ is $C_{1-6}$ alkyl, alkyl-di($C_1$-$C_6$) alkylamino, mono-($C_1$-$C_6$)alkylamino, and di($C_1$-$C_6$)alkylamino. In some embodiments, $R^2$ is selected from methyl, ethyl, propyl, butyl, iso propyl, isobutyl, and

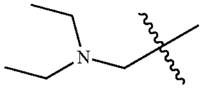.

In some embodiments, $R^3$ is H.

In some embodiments, the compound of Formula (II) or the salt thereof is selected from:

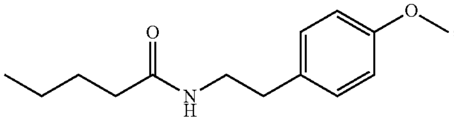,

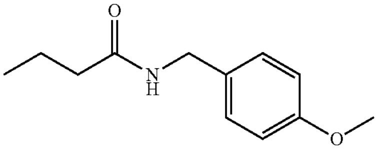,

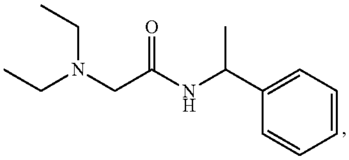,

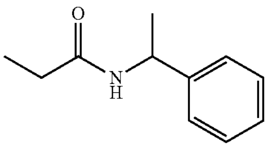,

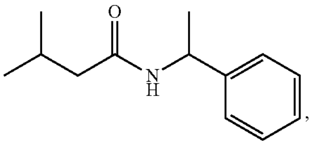,

-continued

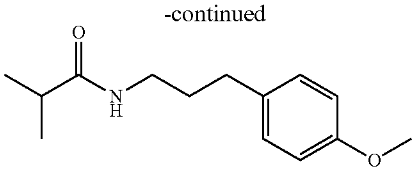, and salts of any one thereof.

Provided herein is a method for preventing or treating a skin condition, disorder, or disease, the method comprising administering to a subject in need thereof a composition comprising a compound having a structure of Formula (I):

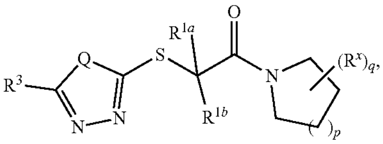

(I)

or salts thereof, wherein:

$R^{1a}$ and $R^{1b}$ are independently selected from H, alkyl, and haloalkyl;

$R^3$ is selected from cycloalkyl, heterocyclyl, aryl, heteroaryl, and aralkyl, wherein the cycloalkyl, heterocyclyl, aryl, heteroaryl, or aralkyl is optionally substituted with one or more substituents independently selected from halogen, alkyl, alkoxy, and haloalkoxy;

$R^x$ is each independently selected from halogen, alkyl, haloalkyl, alkenyl, haloalkenyl, —OH, alkoxy, haloalkoxy, —$NH_2$, alkylamino, dialkylamino, and haloalkylamino;

p is 1, 2, or 3;

q is 0, 1, or 2; and

Q is selected from O, S, and N—$R^2$, wherein $R^2$ is selected from H, alkyl, alkenyl, haloalkyl, haloalkenyl, nitro, —$NH_2$, alkylamino, dialkylamino, and haloalkylamino.

In some embodiments, Q is N—$R^2$.

In some embodiments, $R^2$ is selected from amino, $C_{1-3}$ alkyl, and $C_{1-3}$ alkenyl.

In some embodiments, $R^{1a}$ and $R^{1b}$ are independently selected from H, $C_{1-6}$ alkyl, and $C_{1-6}$ haloalkyl. In some embodiments, $R^{1a}$ and $R^{1b}$ are independently selected from H, $C_{1-4}$ alkyl, and $C_{1-4}$ haloalkyl. In some embodiments, $R^{1a}$ and $R^{1b}$ are H.

In some embodiments, $R^3$ is selected from $C_{4-6}$ cycloalkyl, 5- or 6-membered heterocyclyl, aryl, heteroaryl, alkylaryl, and aralkyl. In some embodiments, $R^3$ is

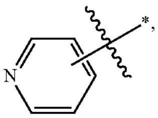, 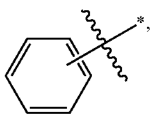, 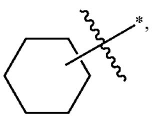, or

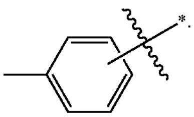.

In some embodiments, $R^3$ is

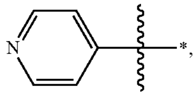, 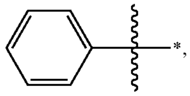, 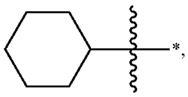, or 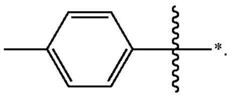.

In some embodiments, q is 0.

In some embodiments, the compound of Formula (I) or the salt thereof is selected from:

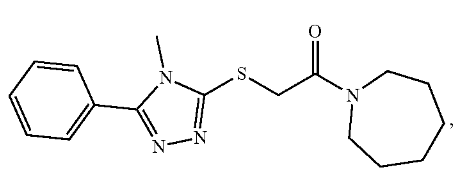,

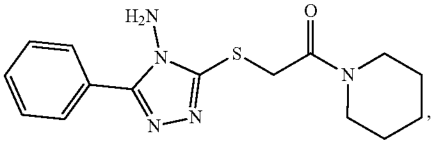,

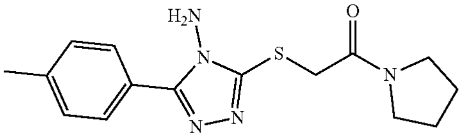,

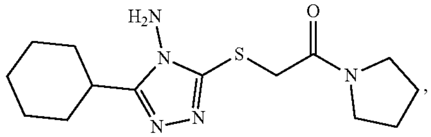,

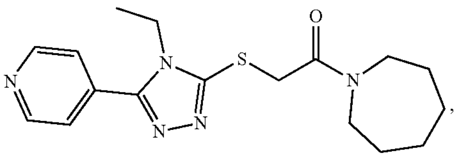,

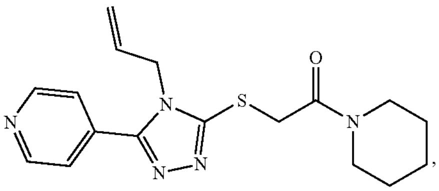,

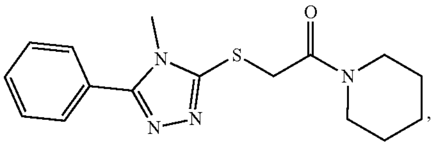, and salts of any one thereof.

Provided herein is a method for preventing or treating a skin condition, disorder, or disease, the method comprising administering to a subject in need thereof a composition comprising a compound having a structure of Formula (VI):

(VI)

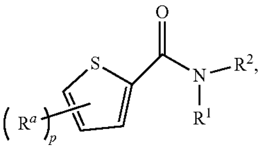

or salts thereof, wherein:

$R^a$ is each independently selected from alkyl, haloalkyl, alkenyl, haloalkenyl, and alkoxy;

one of $R^1$ and $R^2$ is H, or alkyl;

the other one of $R^1$ and $R^2$ is selected from H, alkyl, alkoxy, —($C_1$-$C_6$ alkylene)-C(O)$NR^{x1}$—($C_1$-$C_6$ alkylene)-aryl, and —($C_1$-$C_6$ alkylene)-C(O)$NR^{x2}$—($C_1$-$C_6$ alkyl), wherein $R^{x1}$ and $R^{x2}$ are each independently H, alkyl, or haloalkyl; and p is 0, 1, or 2.

In some embodiments, $R^{x1}$ is H. In some embodiments, $R^{x2}$ is H.

In some embodiments, one of $R^1$ and $R^2$ is H. In some embodiments, the other one of $R^1$ and $R^2$ is selected from $C_1$-$C_6$ alkyl,

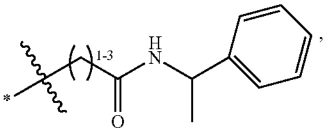, and

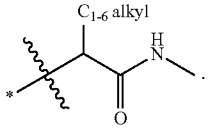.

In some embodiments, the other one of $R^1$ and $R^2$ is selected from isopropyl,

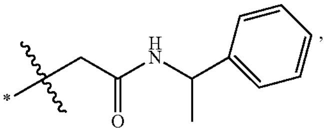, and

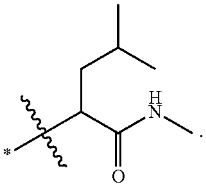.

In some embodiments, p is 0. In some embodiments, p is 1.

In some embodiments, $R^a$ is $C_1$-$C_6$ alkyl or $C_1$-$C_6$ alkoxy. In some embodiments, $R^a$ is $C_1$-$C_3$ alkyl or $C_1$-$C_3$ alkoxy. In some embodiments, $R^a$ is —$CH_3$ or —$OCH_3$.

In some embodiments, the compound of Formula (VI) or the salt thereof is selected from:
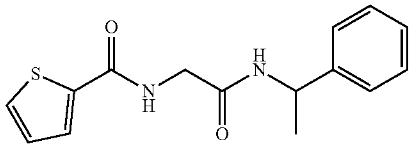
,
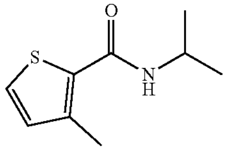
,
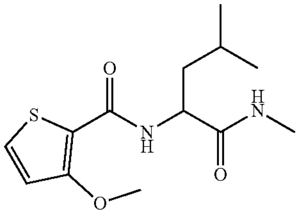
,
and salts of any one thereof.
Provided herein is a method for preventing or treating a skin condition, disorder, or disease, the method comprising administering to a subject in need thereof a composition comprising a compound selected from:
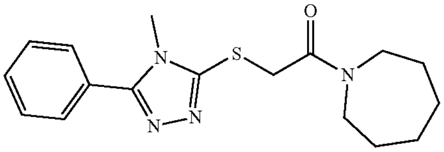
,
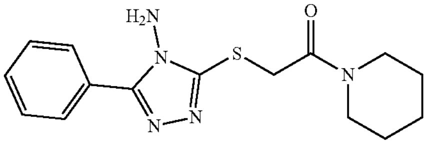
,
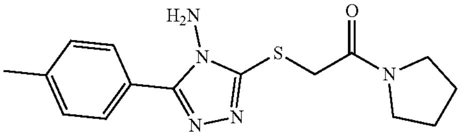
,
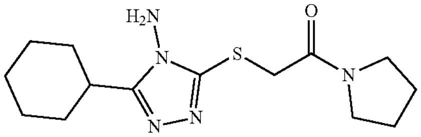
,
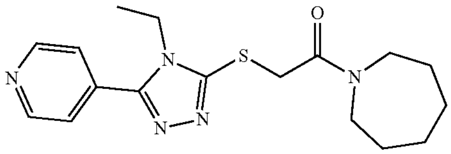
,
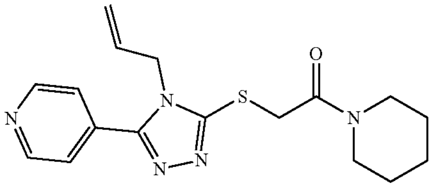
,
-continued
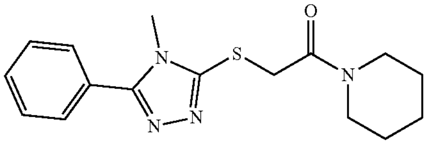
,
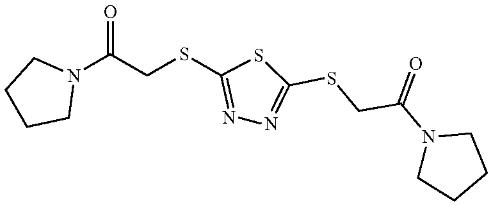
,
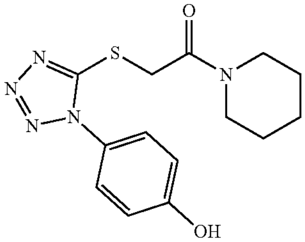
,
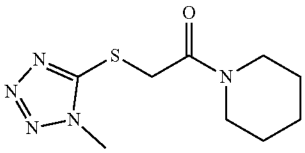
,
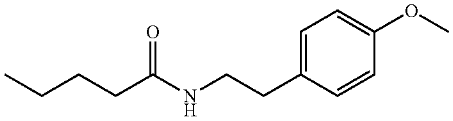
,
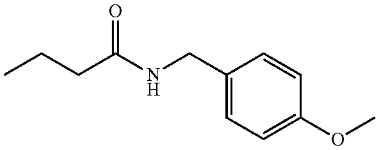
,
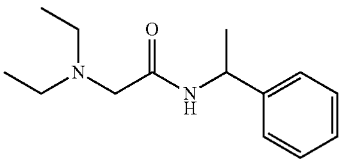
,
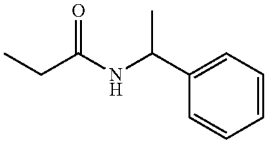
,
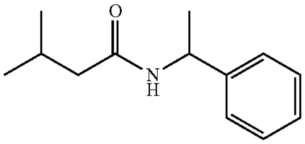
,
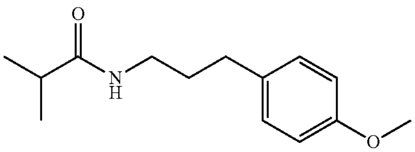
, -continued
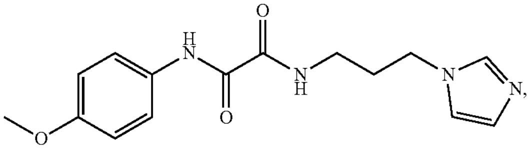
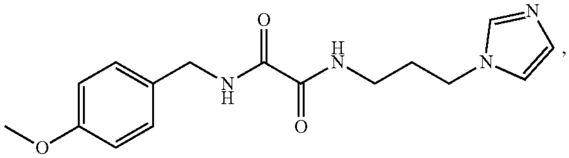
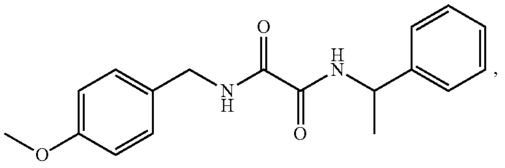
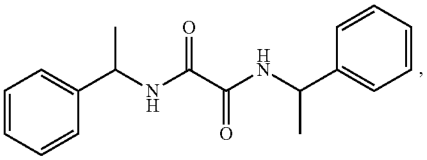
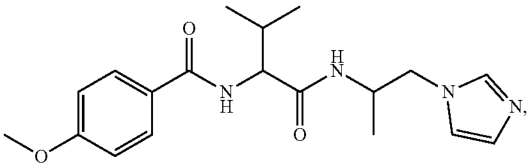
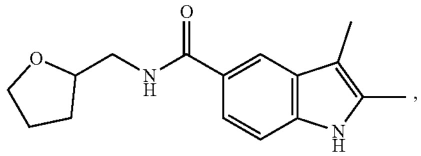
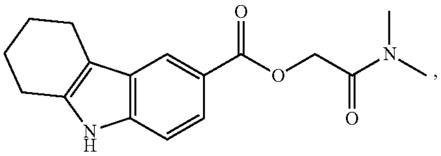
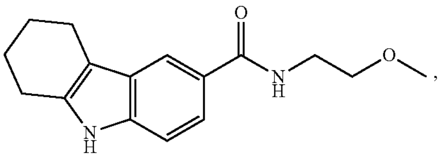
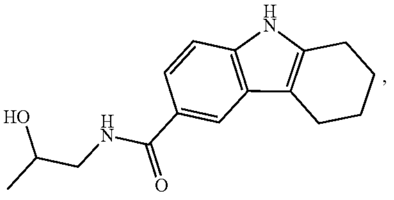
-continued
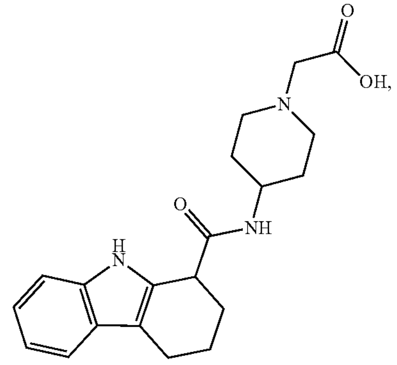
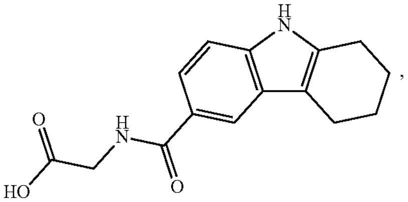
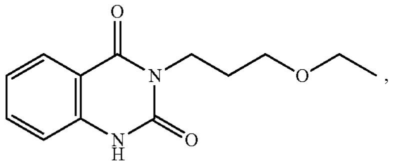
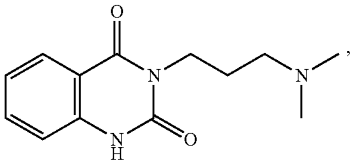
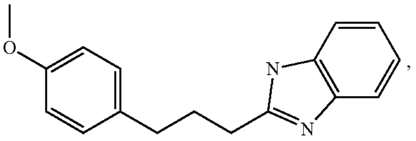
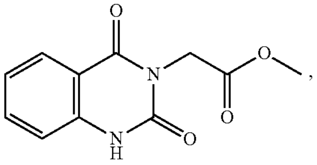
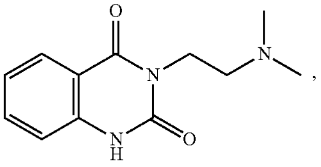
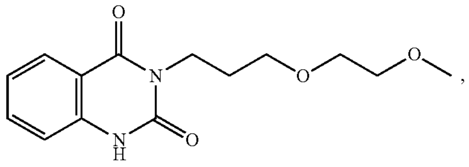
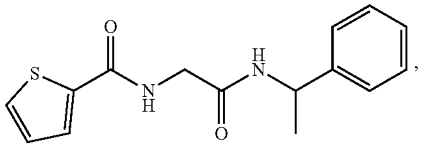

-continued

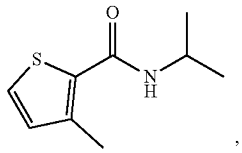

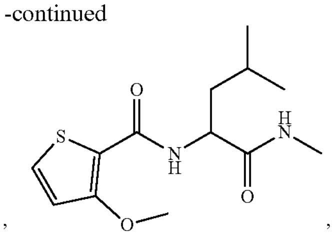

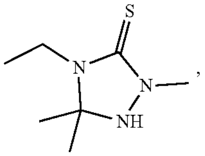

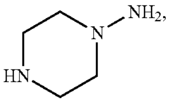

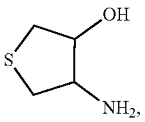

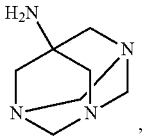

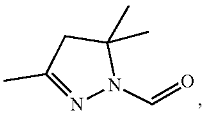

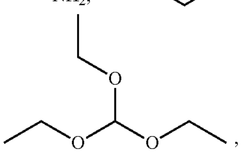

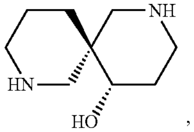

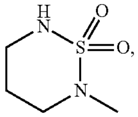

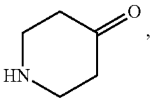

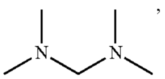

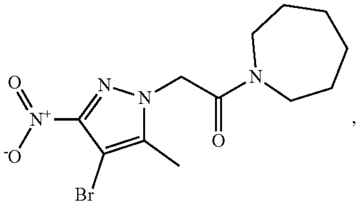

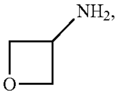

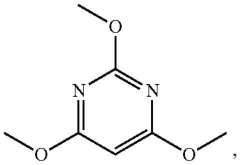

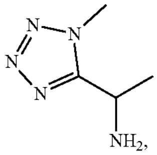

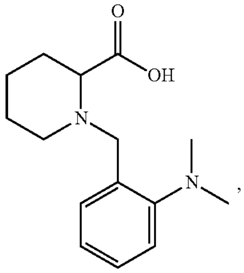

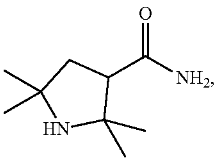

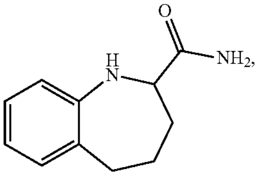

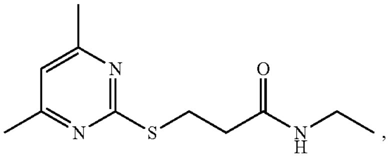

-continued

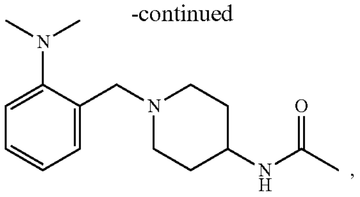

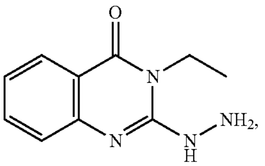

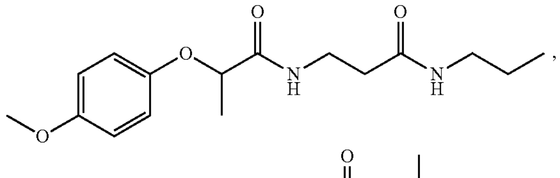

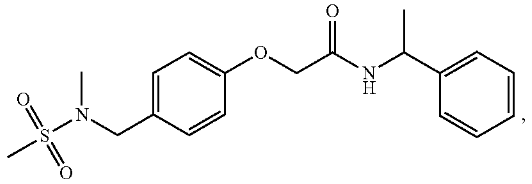

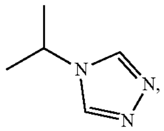

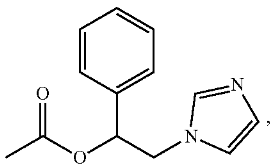

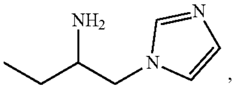

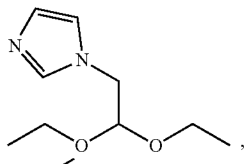

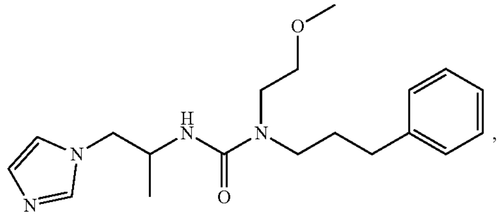

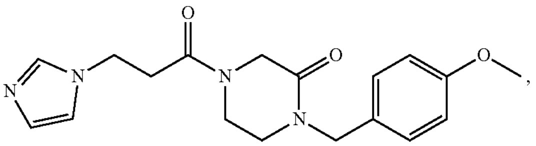

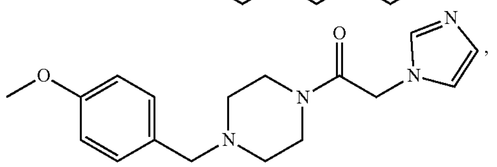

and salts of any one thereof.

In some embodiments, the subject has been diagnosed with the skin condition, disorder, or disease. In some embodiments, the subject has not been diagnosed with the skin condition, disorder, or disease.

In some embodiments, the composition is a pharmaceutical composition. In some embodiments, the composition further comprises at least one additive selected from the group consisting of pharmaceutically acceptable carriers, excipients, adjuvants, diluents, and combinations thereof.

In some embodiments, the composition is a cosmetic composition. In some embodiments, the composition further comprises at least one additive selected from the group consisting of cosmetically acceptable carriers, excipients, adjuvants, diluents, and combinations thereof.

In some embodiments, the composition is formulated as toner, cream, emulsion, lotion, ointment, paste, gel, suspension, serum, oil, spray, milk, mousse, or mist.

In some embodiments, said administering comprises administering said composition to a skin area of said subject. In some embodiments, the skin area comprises face skin, elbow skin, neck skin, hand skin, skin around a joint or combinations thereof. In some embodiments, the face skin comprises skin of forehead, temple, malar area, nasolabial fold, marionette line, chin, mandible, midface, preauricular zone, periorbital hollow, cheek, jaw contour, lip, or any combination of thereof.

In some embodiments, the method prevents or reduces wrinkle(s) or fine line(s). In some embodiments, the method increases skin tightness. In some embodiments, the method moisturizes/hydrates skin. In some embodiments, the method increases skin collagen production or collagen-depositing cell proliferation. In some embodiments, the method increases fibroblast proliferation.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 5A shows example plots of TK.6 cells treated with the compound V-1. Methyl methanesulfonate, a genotoxic, alkylating agent was used as a positive control for micronuclei detection. FIG. 5B shows quantification of the TK.6 micronuclei assay following treatment with various example compounds across a concentration range. FIG. 5C shows normalized β-galactosidase activity (as quantified via absorbance) from the SOS chromotest using a genotoxin (4-NQ; 4-nitroquinoline-1-oxide) and example compounds at varying concentrations. The SOS chromotest is a bacteria-based test for genotoxicity. FIG. 5D shows normalized reactive oxygen species (ROS) activity in human dermal papilla cells treated with g/mL example compounds relative to vehicle control (0.1% v/v DMSO) after 24 hr. All tested example compounds induced minimal change in ROS activity compared to baseline vehicle control. FIG. 5E shows normalized caspase 3/7 activity in HepG2 cells, an immortalized liver cell line used to study apoptosis induced by small molecules.

FIG. 6A shows normalized ARE-luciferase activity using a sensitizing compound (cinnamic aldehyde) and example compounds across a concentration range. FIG. 6B describes an in vitro dendritic cell sensitization test. Dendritic cell activation is widely-associated with downstream immunogenicity. FIGS. 6C-FIG. 6E are example plots showing change in HLA-DR expression. Expression of CD80 (FIG. 6C), PDL-1 (FIG. 6D), and CD141 (FIG. 6E) as quantified via mean fluorescence intensity (MFI) following dosing with example compounds.

DETAILED DESCRIPTION OF THE INVENTION

Figure 1:
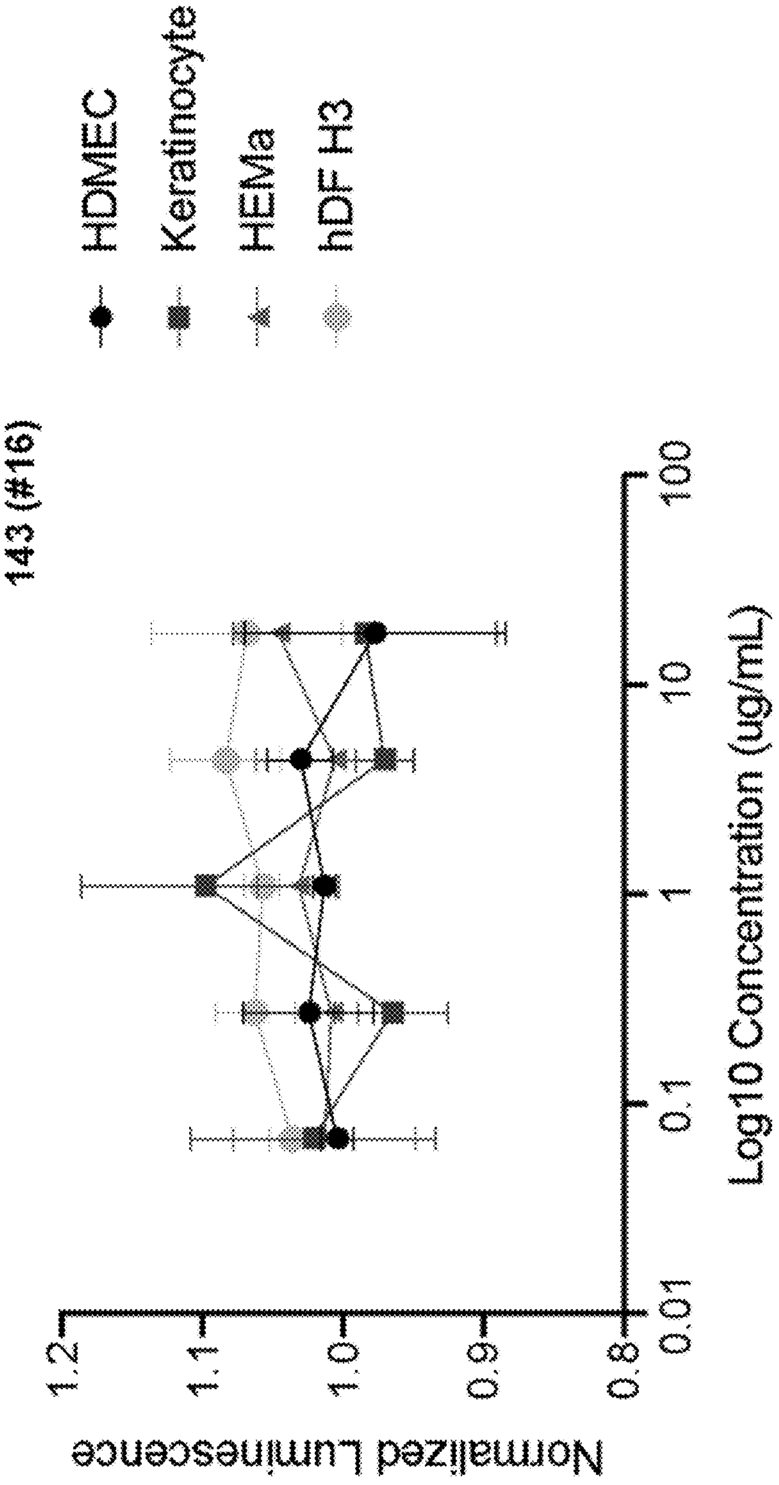
FIG. 1 shows an example depiction of dose response curves from compound I-1.
Figure 2:
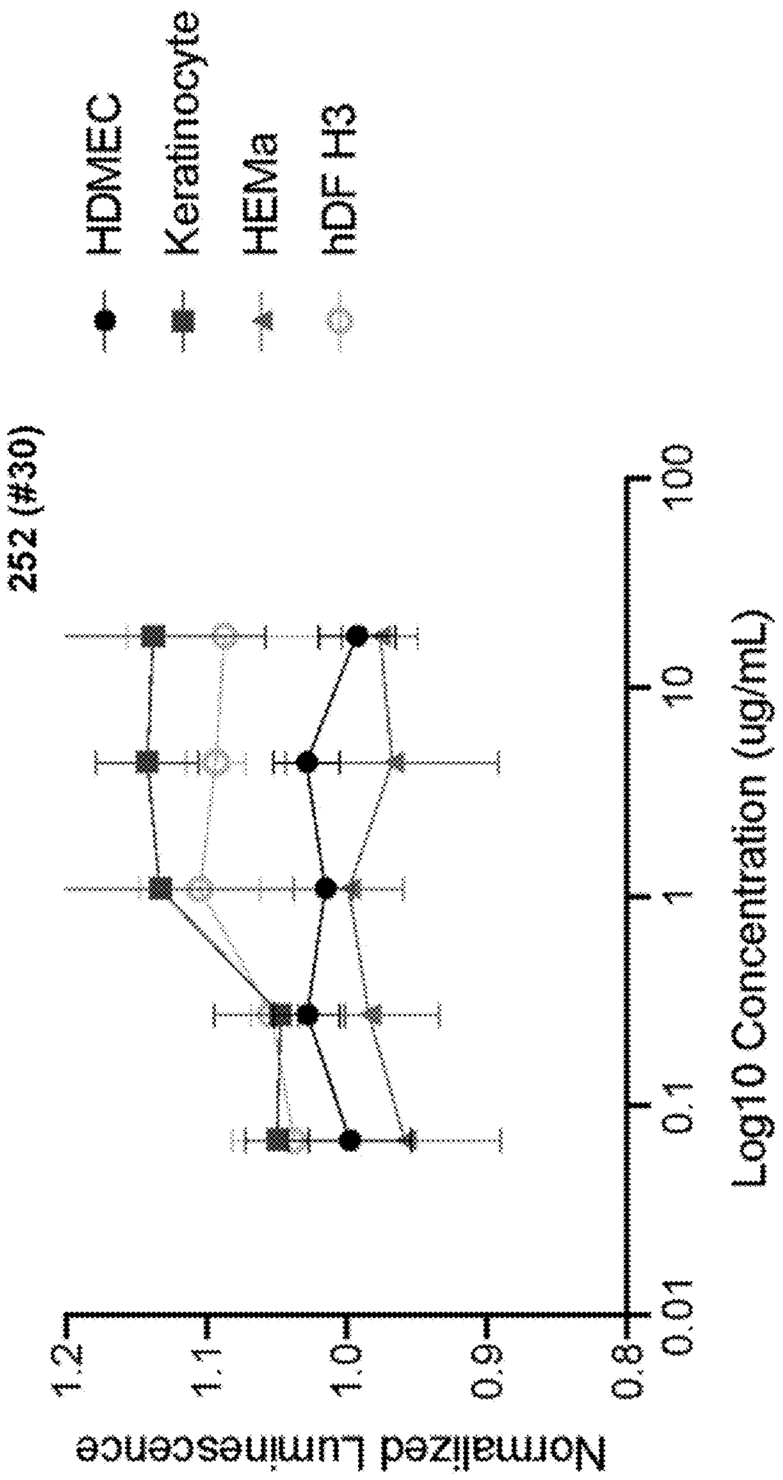
FIG. 2 shows an example depiction of dose response curves from compound II-1.
Figure 3:
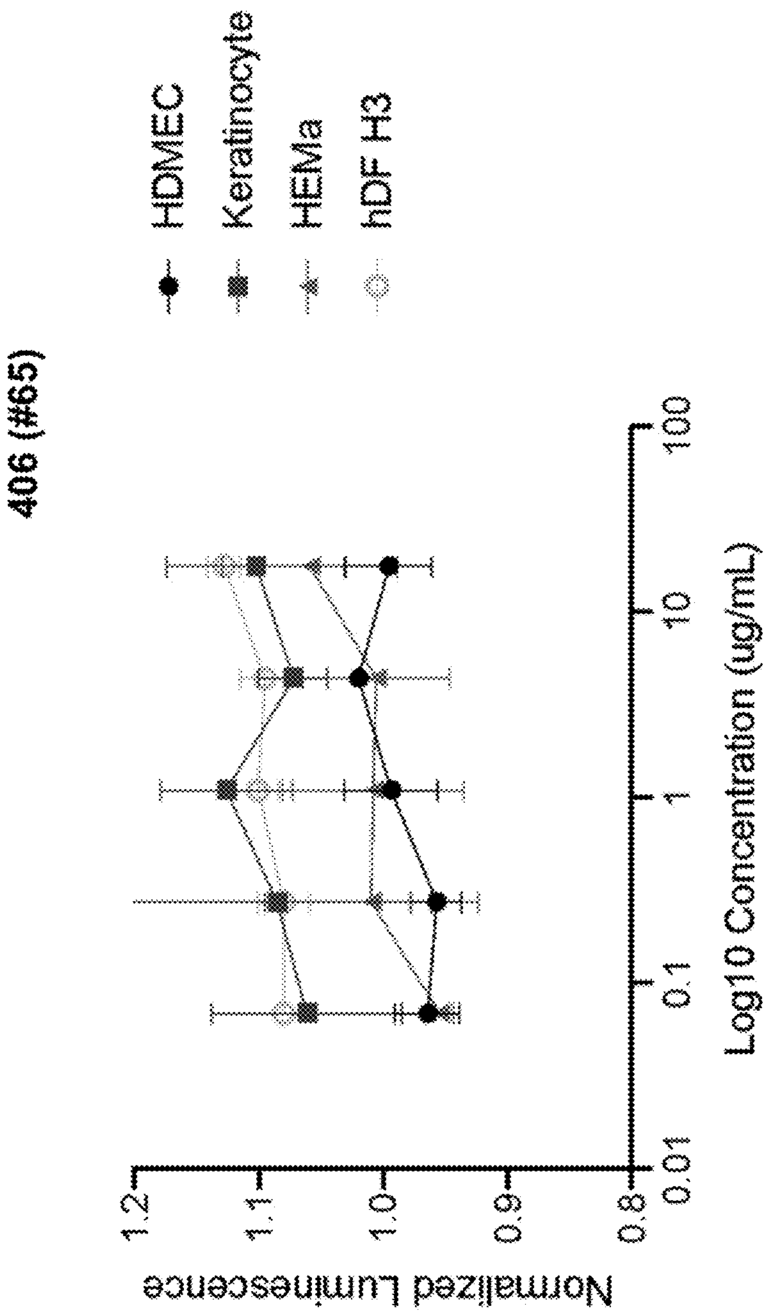
FIG. 3 shows an example depiction of dose response curves from compound IV-2.
Figure 4:
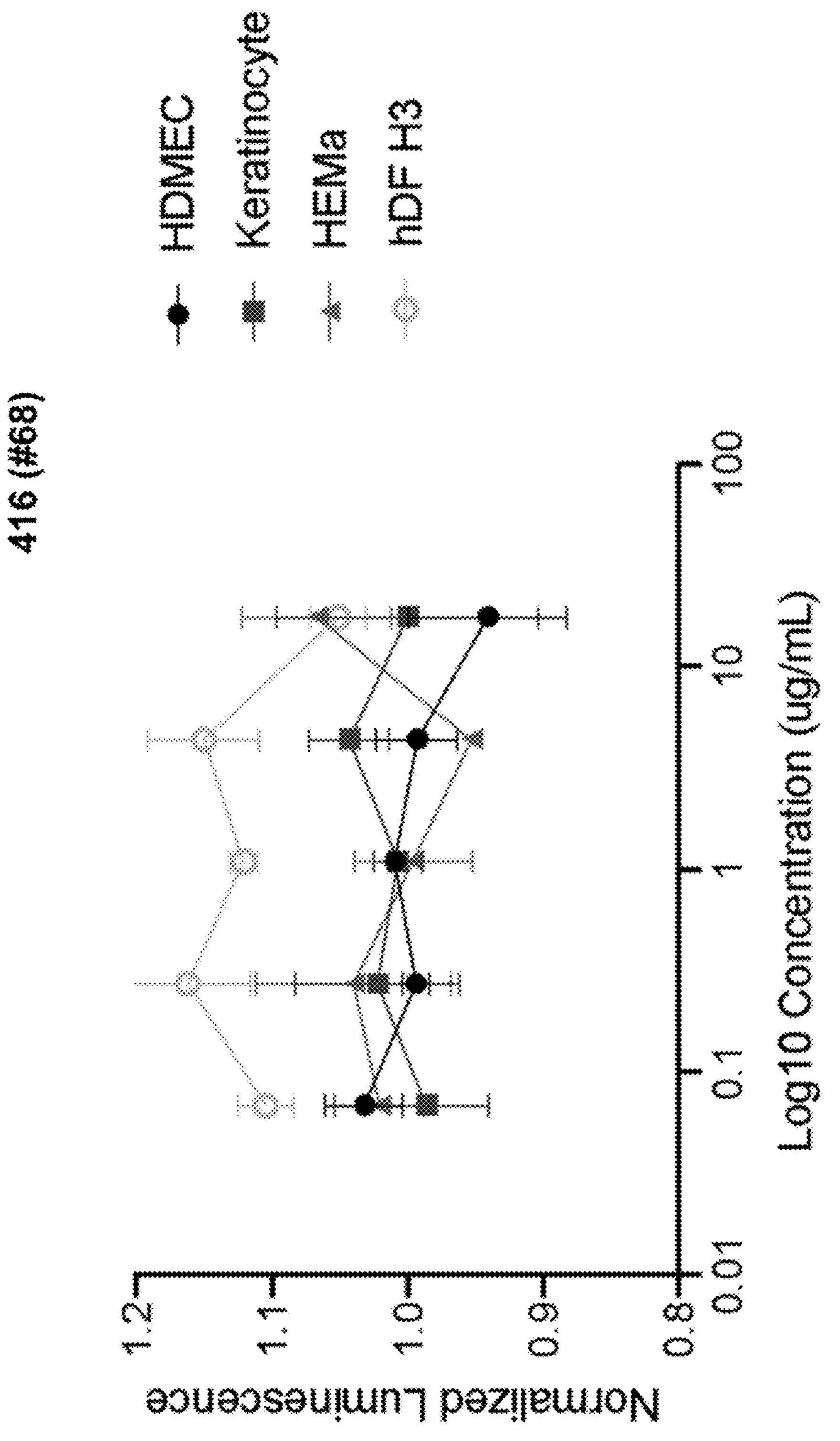
FIG. 4 shows an example depiction of dose response curves from compound V-1.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

In certain aspects, the disclosure provides compositions and compounds useful for preventing or treating hair loss or hair thinning. The compound may include a structure of a compound of Formula (I), (II), (III), (IV), (V), (VI), or (VII), or a salt thereof. The compound may include a structure in Table 1, Table 2, Table 3, Table 4, Table 5, Table 6, Table 7, or Table 8, or a salt thereof. The compound may be included in a pharmaceutical or cosmetic composition or formulation.

In certain aspects, the disclosure provides methods for preventing or treating hair loss or hair thinning (e.g. whether or not a diagnosis of hair loss or hair thinning has been made). Some aspects include a method for preventing or treating a skin condition, disorder, or disease. Some embodiments include a method for treating a skin condition, disorder, or disease. The skin condition, disorder, or disease may be on a subject. The subject may or may not have been diagnosed with the skin condition, disorder, or disease. The method may comprise administering to a subject in need thereof a composition comprising a compound having a structure of a compound of Formula (I), (II), (III), (IV), (V), (VI), or (VII), or a salt thereof. The method may comprise administering to a subject in need thereof a composition comprising a compound having a structure in Table 1, Table 2, Table 3, Table 4, Table 5, Table 6, Table 7, or Table 8, or a salt thereof.

Definitions

Unless defined otherwise, all technical and scientific terms used herein have the same meaning as is commonly understood by one of skill in the art to which this invention belongs.

As used in the specification and claims, the singular form "a", "an" and "the" includes plural references unless the context clearly dictates otherwise.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

The expressions "at least one of A and B" and "at least one of A or B" may be construed to mean at least A, at least B, or at least A and B (i.e., a set comprising A and B, which set may include one or more additional elements). The term "A and/or B" may be construed to mean only A, only B, or both A and B.

The expressions "at least about A, B, and C" and "at least about A, B, or C" may be construed to mean at least about A, at least about B, or at least about C. The expressions "at most about A, B, and C" and "at most about A, B, or C" may be construed to mean at most about A, at most about B, or at most about C.

The expression "between about A and B, C and D, and E and F" may be construed to mean between about A and about B, between about C and about D, and between about E and about F. The expression "between about A and B, C and D, or E and F" may be construed to mean between about A and about B, between about C and about D, or between about E and about F.

The expression "about A to B and C to D" may be construed to mean between about A and about B and between about C and about D. The expression "about A to B or C to D" may be construed to mean between about A and about B or between about C and about D.

The term "exemplary" as used herein means "serving as an example, instance, or illustration." Any embodiment described herein as "exemplary" is not to be construed as preferred or advantageous over other embodiments.

The term "$C_{x-y}$" or "$C_x$-$C_y$" when used in conjunction with a chemical moiety, such as alkyl, alkenyl, or alkynyl is meant to include groups that contain from x to y carbons in the chain. For example, the term "$C_{1-6}$alkyl" refers to substituted or unsubstituted saturated hydrocarbon groups, including straight-chain alkyl and branched-chain alkyl groups that contain from 1 to 6 carbons.

The terms "$C_{x-y}$alkenyl" and "$C_{x-y}$alkynyl" refer to substituted or unsubstituted unsaturated aliphatic groups analogous in length and possible substitution to the alkyls described above, but that contain at least one double or triple bond, respectively.

The term "aryl" refers to an aromatic monocyclic or aromatic multicyclic hydrocarbon ring system. The aromatic monocyclic or aromatic multicyclic hydrocarbon ring system contains only hydrogen and carbon and from five to eighteen carbon atoms, where at least one of the rings in the ring system is aromatic, i.e., it contains a cyclic, delocalized $(4n+2)$ π-electron system in accordance with the Hückel theory. The ring system from which aryl groups are derived include, but are not limited to, groups such as benzene, fluorene, indane, indene, tetralin and naphthalene.

The term "cycloalkyl" refers to a saturated ring in which each atom of the ring is carbon. Cycloalkyl may include monocyclic and polycyclic rings such as 3- to 10-membered monocyclic rings, 5- to 12-membered bicyclic rings, spiro bicycles, and 5- to 12-membered bridged rings. In certain embodiments, a cycloalkyl comprises three to ten carbon atoms. In other embodiments, a cycloalkyl comprises five to seven carbon atoms. The cycloalkyl may be attached to the rest of the molecule by a single bond. Examples of monocyclic cycloalkyls include, e.g., cyclopropyl, cyclobutyl, cyclopentyl, cyclohexyl, cycloheptyl, and cyclooctyl.

The term "halo" or, alternatively, "halogen" or "halide," means fluoro, chloro, bromo or iodo. In some embodiments, halo is fluoro, chloro, or bromo.

The term "haloalkyl" refers to an alkyl radical, as defined above, that is substituted by one or more halo radicals, for example, trifluoromethyl, dichloromethyl, bromomethyl, 2,2,2-trifluoroethyl, 1-chloromethyl-2-fluoroethyl, and the like. In some embodiments, the alkyl part of the haloalkyl radical is optionally further substituted as described herein.

The term "heterocycle" as used herein refers to a saturated, unsaturated or aromatic ring comprising one or more heteroatoms. Exemplary heteroatoms include N, O, Si, P, B, and S atoms. Heterocycles include 3- to 10-membered monocyclic rings, 6- to 12-membered bicyclic rings, 5- to 12-membered spiro bicycles, and 5- to 12-membered bridged rings. A bicyclic heterocycle includes any combination of saturated, unsaturated and aromatic bicyclic rings, as valence permits. In an exemplary embodiment, an aromatic ring, e.g., pyridyl, may be fused to a saturated or unsaturated ring, e.g., cyclohexane, cyclopentane, morpholine, piperidine or cyclohexene. A bicyclic heterocycle includes any combination of ring sizes such as 4-5 fused ring systems, 5-5 fused ring systems, 5-6 fused ring systems, 6-6 fused ring systems, 5-7 fused ring systems, 6-7 fused ring systems, 5-8 fused ring systems, and 6-8 fused ring systems. A bicyclic heterocycle further includes spiro bicylic rings e.g., 5 to 12-membered spiro bicycles.

The term "heterocycloalkyl" refers to a stable 3- to 12-membered non-aromatic ring radical that comprises two to twelve carbon atoms and at least one heteroatom wherein each heteroatom may be selected from N, O, Si, P, B, and S atoms. The heterocycloalkyl may be selected from monocyclic or bicyclic, and fused or bridged ring systems. The heteroatoms in the heterocycloalkyl radical are optionally oxidized. One or more nitrogen atoms, if present, are optionally quaternized. The heterocycloalkyl radical is partially or fully saturated. The heterocycloalkyl is attached to the rest of the molecule through any atom of the heterocycloalkyl, valence permitting, such as any carbon or nitrogen atoms of the heterocycloalkyl. Examples of heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl" refers to a radical derived from a 5 to 18 membered aromatic ring radical that comprises two to seventeen carbon atoms and from one to six heteroatoms selected from nitrogen, oxygen and sulfur. As used herein, the heteroaryl radical is a monocyclic, bicyclic, tricyclic or tetracyclic ring system, wherein at least one of the rings in the ring system is aromatic, i.e., it contains a cyclic, delocalized (4n+2) π-electron system in accordance with the Hückel theory. Heteroaryl includes fused or bridged ring systems. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to, azepinyl, acridinyl, benzimidazolyl, benzindolyl, 1,3-benzodioxolyl, benzofuranyl, benzoxazolyl, and thiophenyl (i.e. thienyl).

The term "substituted" refers to moieties having substituents replacing a hydrogen on one or more carbons or substitutable heteroatoms, e.g., an NH or $NH_2$ of a compound. It will be understood that "substitution" or "substituted with" includes the implicit proviso that such substitution is in accordance with permitted valence of the substituted atom and the substituent, and that the substitution results in a stable compound, i.e., a compound which does not spontaneously undergo transformation such as by rearrangement, cyclization, elimination, etc. In certain embodiments, substituted refers to moieties having substituents replacing two hydrogen atoms on the same carbon atom, such as substituting the two hydrogen atoms on a single carbon with an oxo, imino or thioxo group. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds.

In some embodiments, substituents may include any substituents described herein, for example: halogen, hydroxy, oxo (=O), thioxo (=S), cyano (—CN), nitro (—$NO_2$), imino (=N—H), oximo (=N—OH), hydrazino (=N—$NH_2$), —$R^{bb}$—$OR^{aa}$, —$R^{bb}$—OC(O)—$R^{aa}$, —$R^{bb}$—OC(O)—$OR^{aa}$, —$R^{bb}$—OC(O)—N($R^{aa}$)$_2$, —$R^{bb}$—N($R^{aa}$)$_2$, —$R^{bb}$—C(O)$R^{aa}$, —$R^{bb}$—C(O)$OR^{aa}$, —$R^{bb}$—C(O)N($R^{aa}$)$_2$, —$R^{bb}$—O—$R^{cc}$—C(O)N($R^{aa}$)$_2$, —$R^{bb}$—N($R^{aa}$)C(O)$OR^{aa}$, —$R^{bb}$—N($R^{aa}$)C(O)$R^{aa}$, —$R^{bb}$—N($R^{aa}$)S(O)$_t$$R^{aa}$ (where t is 1 or 2), —$R^{bb}$—S(O)$_t$$R^{aa}$ (where t is 1 or 2), —$R^{bb}$—S(O)$_t$$OR^{aa}$ (where t is 1 or 2), and —$R^{bb}$—S(O)$_t$N($R^{aa}$)$_2$ (where t is 1 or 2); and alkyl, alkenyl, alkynyl, aryl, aralkyl, aralkenyl, aralkynyl, cycloalkyl, cycloalkylalkyl, heterocycloalkyl, heterocycloalkylalkyl, heteroaryl, and heteroarylalkyl, any of which may be optionally substituted by alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^{bb}$—$OR^{aa}$, —$R^{bb}$—OC(O)—$R^{aa}$, —$R^{bb}$—OC(O)—$OR^{aa}$, —$R^{bb}$—OC(O)—N($R^{aa}$)$_2$, —$R^{bb}$—N($R^{aa}$)$_2$, —$R^{bb}$—C(O)$R^{aa}$, —$R^{bb}$—C(O)$OR^{aa}$, —$R^{bb}$—C(O)N($R^{aa}$)$_2$, —$R^{bb}$—O—$R^{cc}$—C(O)N($R^{aa}$)$_2$, —$R^{bb}$—N($R^{aa}$)C(O)$OR^{aa}$, —$R^{bb}$—N($R^{aa}$)C(O)$R^{aa}$, —$R^{bb}$—N($R^{aa}$)S(O)$_t$$R^{aa}$ (where t is 1 or 2), —$R^{bb}$—S(O)$_t$$R^{aa}$ (where t is 1 or 2), —$R^{bb}$—S(O)$_t$$OR^{aa}$ (where t is 1 or 2) and —$R^{bb}$—S(O)$_t$N($R^{aa}$)$_2$ (where t is 1 or 2); wherein each $R^{aa}$ is independently selected from hydrogen, alkyl, cycloalkyl, cycloalkylalkyl, aryl, aralkyl, heterocycloalkyl, heterocycloalkylalkyl, heteroaryl, or heteroarylalkyl, wherein each $R^{aa}$, valence permitting, may be optionally substituted with alkyl, alkenyl, alkynyl, halogen, haloalkyl, haloalkenyl, haloalkynyl, oxo (=O), thioxo (=S), cyano (—CN), nitro (—$NO_2$), imino (=N—H), oximo (=N—OH), hydrazine (=N—$NH_2$), —$R^{bb}$—$OR^{aa}$, —$R^{bb}$—OC(O)—$R^{aa}$, —$R^{bb}$—OC(O)—$OR^{aa}$, —$R^{bb}$—OC(O)—N($R^{aa}$)$_2$, —$R^{bb}$—N($R^{aa}$)$_2$, —$R^{bb}$—C(O)$R^{aa}$, —$R^{bb}$—C(O)$OR^{aa}$, —$R^{bb}$—C(O)N($R^{aa}$)$_2$, —$R^{bb}$—O—$R^{cc}$—C(O)N($R^{aa}$)$_2$, —$R^{bb}$—N($R^{aa}$)C(O)$OR^{aa}$, —$R^{bb}$—N($R^{aa}$)C(O)$R^{aa}$, —$R^{bb}$—N($R^{aa}$)S(O)$_t$$R^{aa}$ (where t is 1 or 2), —$R^{bb}$—S(O)$_t$$R^{aa}$ (where t is 1 or 2), —$R^{bb}$—S(O)$_t$$OR^{aa}$ (where t is 1 or 2) and —$R^{bb}$—S(O)$_t$N($R^{aa}$)$_2$ (where t is 1 or 2); and wherein each $R^{bb}$ is independently selected from a direct bond or a straight or branched alkylene, alkenylene, or alkynylene chain, and each $R^{cc}$ is a straight or branched alkylene, alkenylene or alkynylene chain.

Double bonds to oxygen atoms, such as oxo groups, are represented herein as both "=O" and "(O)". Double bonds to nitrogen atoms are represented as both "=NR" and "(NR)". Double bonds to sulfur atoms are represented as both "=S" and "(S)".

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient" or "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The term "salt" or "pharmaceutically acceptable salt" refers to salts derived from a variety of organic and inorganic counter ions well known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

In certain embodiments, the term "cosmetically acceptable salt" means any salt that is cosmetically tolerated if used appropriately for a cosmetic treatment especially if used on or applied to humans and/or mammals. In certain embodiments, these salts include, but are not restricted to the salts used to form base addition salts, either inorganic, such as for example and in a non-limiting sense, lithium, sodium, potassium, calcium, magnesium or aluminum, among others, or organic such as for example and in a non-limiting sense, ethylamine, diethylamine, ethylenediamine, ethanolamine, diethanolamine, arginine, lysine, histidine, or piperazine among others; or acid addition salts, either organic, such as for example and in a non-limiting sense, acetate, citrate, lactate, malonate, maleate, tartrate, fumarate, benzoate, aspartate, glutamate, succinate, oleate, trifluoroacetate, oxalate, pamoate or gluconate among others, or inorganic, such as for example and in a non-limiting sense, chloride, sulfate, borate, or carbonate among others.

A "cosmetically effective amount" as used herein refers to the amount of a compound sufficient to improve the outward physical appearance of a subject. It is to be understood that a "cosmetically effective" amount can vary from subject to subject, due to numerous factors including for example age, weight, general condition of the subject, the condition being treated, the severity of the condition being treated, and the judgment of the prescribing physician.

The phrase "cosmetically acceptable excipient" or "cosmetically acceptable carrier" as used herein comprises as a pharmaceutical cream base, an oil-in-water emulsion, a water-in-oil emulsion, a gel, or the like. The skilled artisan will understand that the appropriate carriers typically will contain ingredients, such as those typically found in the cosmetic and cosmeceutical fields: oils, waxes or other standard fatty substances, or conventional gelling agents and/or thickeners; emulsifiers; moisturizing agents; emollients; sunscreens; hydrophilic or lipophilic active agents; agents for combatting free radicals; preservatives; basifying or acidifying agents; fragrances; surfactants; fillers; natural products or extracts of natural product, such as aloe or green tea extract; vitamins; or coloring materials.

The term "in vivo" generally refers to an event that takes place in a subject's body.

The term "in vitro" generally refers to an event that takes place outside of a subject's body. For example, an in vitro assay encompasses any assay run outside of a subject. In vitro assays encompass cell-based assays in which cells alive or dead are employed. In vitro assays also encompass a cell-free assay in which no intact cells are employed.

"Optional" or "optionally" means that the subsequently described event of circumstances may or may not occur, and that the description includes instances where the event or circumstance occurs and instances in which it does not. For example, "optionally substituted aryl" means that the aryl group may or may not be substituted and that the description includes both substituted aryl groups and aryl groups having no substitution.

"Pharmaceutically acceptable carrier, diluent or excipient" includes without limitation any adjuvant, carrier, excipient, glidant, sweetening agent, diluent, preservative, dye, colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Compounds

The present disclosure provides compounds, salts thereof, and compositions and formulations thereof, for skin treatment. The compounds or salts thereof may have a structural formula (I), (II), (III), (IV), (V), (VI), or (VII). The compounds or salts thereof may be selected from those forth in Tables 1-8, or any subset thereof. The compounds and salts thereof disclosed herein may be used in method(s) of the disclosure.

Compounds of Formula (I) and Salts Thereof

In certain aspects, disclosed herein is a compound having a structure of Formula (I):

(I)

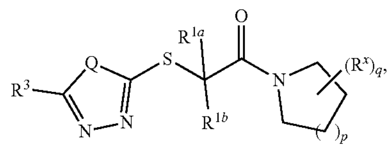

or a (e.g., pharmaceutically or cosmetically acceptable) salt thereof, wherein:

- $R^{1a}$ and $R^{1b}$ are independently selected from H, alkyl, and haloalkyl;
- $R^3$ is selected from cycloalkyl, heterocyclyl, aryl, heteroaryl, and aralkyl, wherein the cycloalkyl, heterocyclyl, aryl, heteroaryl, or aralkyl is optionally substituted with one or more substituents independently selected from halogen, alkyl, alkoxy, and haloalkoxy;
- $R^x$ is each independently selected from halogen, alkyl, haloalkyl, alkenyl, haloalkenyl, —OH, alkoxy, haloalkoxy, —$NH_2$, alkylamino, dialkylamino, and haloalkylamino;
- p is 1, 2, or 3;
- q is 0, 1, or 2; and
- Q is selected from O, S, and N—$R^2$, wherein $R^2$ is selected from H, alkyl, alkenyl, haloalkyl, haloalkenyl, nitro, —$NH_2$, alkylamino, dialkylamino, and haloalkylamino.

In some embodiments of a compound having structural Formula (I) (or a salt thereof), Q is N—$R^2$. In some embodiments, $R^2$ is selected from amino, (e.g., $C_1$-$C_3$) alkyl, and (e.g., $C_1$-$C_3$) alkenyl. In some embodiments, $R^2$ is $C_1$ alkyl. In some embodiments, $R^2$ is $C_2$ alkyl. In some embodiments, $R^2$ is —$CH_2CHCH_2$. In some embodiments, $R^2$ is —$NH_2$.

In some embodiments, $R^{1a}$ and $R^{1b}$ are independently selected from H, (e.g., $C_{1-6}$, such as $C_{1-4}$) alkyl, and (e.g., $C_{1-6}$, such as $C_{1-4}$) haloalkyl. In some embodiments, $R^{1a}$ and $R^{1b}$ are H.

In some embodiments, $R^3$ is selected from (e.g., $C_4$-$C_6$) cycloalkyl, (e.g., 5- or 6-membered) heterocyclyl, aryl (e.g., phenyl), heteroaryl (e.g., pyridine), alkylaryl, and aralkyl (e.g., benzyl). In some embodiments, $R^3$ is

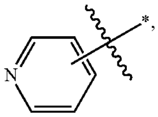,
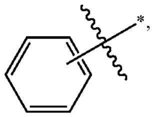,
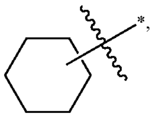, or
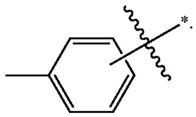.

In some embodiments, $R^3$ is

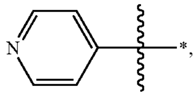,
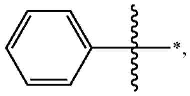,
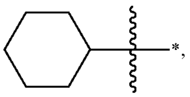, or
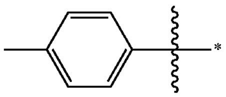

In some embodiments, $R^3$ is

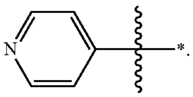.

In some embodiments, $R^3$ is

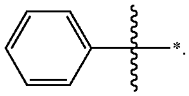.

In some embodiments, $R^3$ is

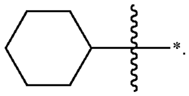.

In some embodiments, $R^3$ is

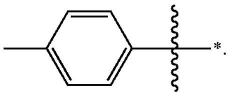.

In some embodiments, q is 0.

In some embodiments, a compound having structural Formula (I) is selected from those set forth in Table 1, and salts thereof.

TABLE 1

Example Compounds of Formula (I)

| ID # | Chemical Structure | Chemical Name | Molecular Weight |
|---|---|---|---|
| I-1 | 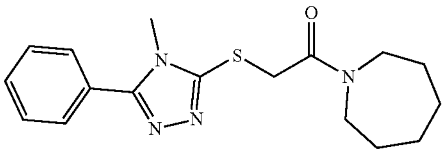 [SMILES: Cn1c(SCC(=O)N2CCCCCC2)nnc1-c1ccccc1] | 1-(azepan-1-yl)-2-[(4-methyl-5-phenyl-1,2,4-triazol-3-yl)sulfanyl]ethanone | 330.457 |
| I-2 | 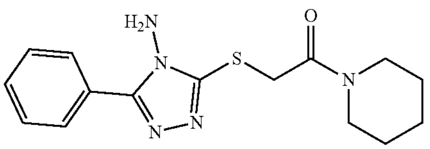 [SMILES: Nn1c(SCC(=O)N2CCCCC2)nnc1-c1ccccc1] | 2-[(4-amino-5-phenyl-1,2,4-triazol-3-yl)sulfanyl]-1-piperidin-1-ylethanone | 317.418 |
| I-3 | 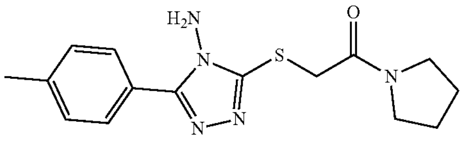 [SMILES: Cc1ccc(-c2nnc(SCC(=O)N3CCCC3)n2N)cc1] | 2-[[4-amino-5-(4-methylphenyl)-1,2,4-triazol-3-yl]sulfanyl]-1-pyrrolidin-1-ylethanone | 317.418 |

TABLE 1-continued

| Example Compounds of Formula (I) | | | |
|---|---|---|---|
| ID # | Chemical Structure | Chemical Name | Molecular Weight |
| I-4 | 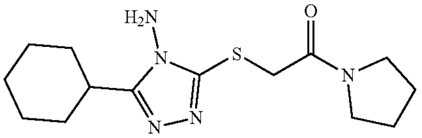 [SMILES: Nn1c(SCC(=O)N2CCCC2)nnc1C1CCCCC1] | 2-[(4-amino-5-cyclohexyl-1,2,4-triazol-3-yl)sulfanyl]-1-pyrrolidin-1-ylethanone | 309.439 |
| I-5 | 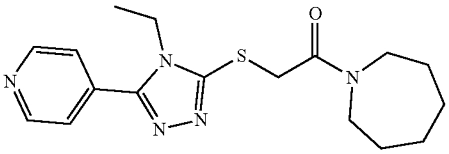 [SMILES: CCn1c(SCC(=O)N2CCCCCC2)nnc1-c1ccncc1] | 1-(azepan-1-yl)-2-[(4-ethyl-5-pyridin-4-yl-1,2,4-triazol-3-yl)sulfanyl]ethanone | 345.472 |
| I-6 | 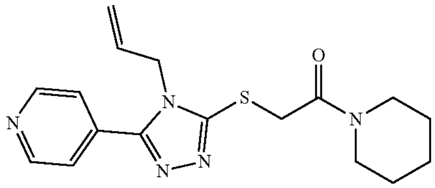 [SMILES: C=CCn1c(SCC(=O)N2CCCCC2)nnc1-c1ccncc1] | 1-piperidin-1-yl-2-[(4-prop-2-enyl-5-pyridin-4-yl-1,2,4-triazol-3-yl)sulfanyl]ethanone | 343.456 |
| I-7 | 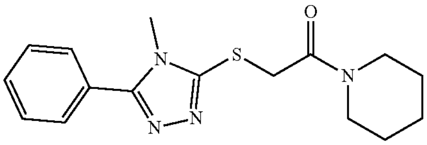 [SMILES: Cn1c(SCC(=O)N2CCCCC2)nnc1-c1ccccc1] | 2-[(4-methyl-5-phenyl-1,2,4-triazol-3-yl)sulfanyl]-1-piperidin-1-ylethanone | 316.430 |

Compounds of Formula (II) and Salts Thereof

In certain aspects, disclosed herein is a compound represented by Formula (II):

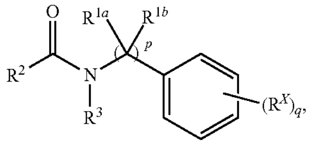

(II)

or a (e.g., pharmaceutically or cosmetically acceptable) salt thereof, wherein:

$R^{1a}$ and $R^{1b}$ are each independently selected from H, alkyl, haloalkyl, alkenyl, haloalkenyl, aryl (e.g., phenyl), and aralkyl (e.g., benzyl);

$R^x$ is each independently selected from halogen, alkyl, haloalkyl, alkenyl, haloalkenyl, —OH, alkoxy, haloalkoxy, nitro, —$NH_2$, alkylamino, dialkylamino, and haloalkylamino;

p is 1, 2, or 3;

q is 0, 1, or 2;

$R^2$ is selected from H, alkyl, alkenyl, haloalkyl, haloalkenyl, nitro, —$NH_2$, alkylamino, dialkylamino, alkyl-dialkylamino, and haloalkylamino; and $R^3$ is selected from H, alkyl, and haloalkyl.

In some embodiments, $R^{1a}$ and $R^{1b}$ are independently selected from H and (e.g., $C_{1-6}$, such as $C_{1-4}$) alkyl. In some embodiments, $R^{1a}$ and $R^{1b}$ are independently $C_{1-4}$ alkyl. In some embodiments, $R^{1a}$ and $R^{1b}$ are independently $C_1$ alkyl. In some embodiments, $R^{1a}$ and $R^{1b}$ are H.

In some embodiments, $R^x$ is $C_1$ to $C_6$ alkoxy. In some embodiments, $R^x$ is —$OCH_3$.

In some embodiments, q is 0 or 1. In some embodiments, q is 0. In some embodiments, q is 1. In some embodiments, p is 1.

In some embodiments, $R^2$ is (e.g., $C_1$ to $C_6$) alkyl, alkyl-dialkylamino, monoalkylamino (e.g., mono-($C_1$-$C_6$)alkylamino), and dialkylamino (e.g., di($C_1$-$C_6$)alkylamino). In some embodiments, alkyl-dialkylamino is, for example, $(CH_3CH_2)_2N(CH_2)$—. In some embodiments, alkylamino is, for example, —$CH_2NH$—. In some embodiments, dialkylamino is, for example, $(CH_3CH_2)_2N$—. In some embodiments, $R^2$ is linear $C_2$ alkyl. In some embodiments, $R^2$ is linear $C_3$ alkyl. In some embodiments, $R^2$ is linear $C_4$ alkyl. In some embodiments, $R^2$ is branched $C_3$ alkyl. In some embodiments, $R^2$ is branched $C_4$ alkyl. In some embodiments, $R^2$ is branched $C_3$ alkyl. In some embodiments, $R^2$ is selected from methyl, ethyl, propyl, butyl, iso propyl, isobutyl, and

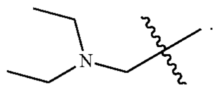 [SMILES: *CN(CC)CC]

In some embodiments, $R^3$ is H.

In some embodiments, a compound having structural Formula (II) is selected from those set forth in Table 2, and salts thereof.

TABLE 2

| ID # | Chemical Structure | Chemical Name | Molecular Weight |
|---|---|---|---|
| Example Compounds of Formula (II) | | | |
| II-1 | 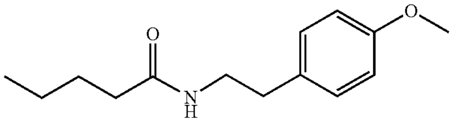 [SMILES: CCCCC(=O)NCCc1ccc(OC)cc1] | N-[2-(4-methoxyphenyl)ethyl]pentanamide | 235.327 |
| II-2 | 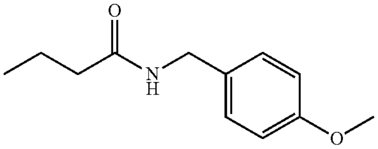 | N-[(4-methoxyphenyl)methyl]butanamide | 207.273 |
| II-3 | 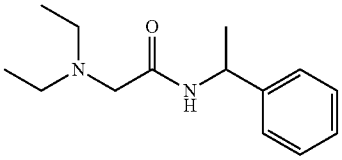 [SMILES: CCN(CC)CC(=O)NC(C)c1ccccc1] | 2-(diethylamino)-N-(1-phenylethyl)acetamide | 234.343 |
| II-4 | 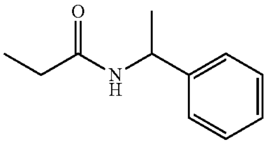 | N-(1-phenylethyl)propanamide | 177.247 |
| II-5 | 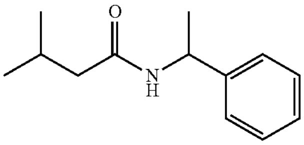 | 3-methyl-N-(1-phenylethyl)butanamide | 205.301 |
| II-6 | 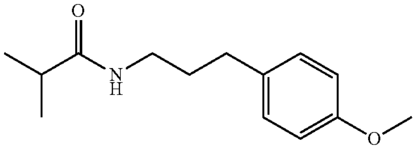 [SMILES: COc1ccc(CCCNC(=O)C(C)C)cc1] | N-[3-(4-methoxyphenyl)propyl]-2-methylpropanamide | 235.327 |

Compounds of Formula (I) and Salts Thereof

In certain aspects, disclosed herein is a compound represented by Formula (III):

(III)

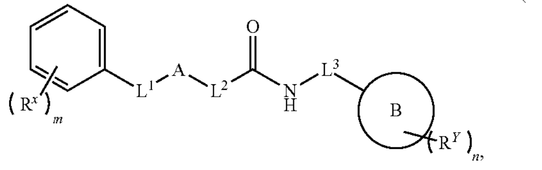

or a (e.g., pharmaceutically or cosmetically acceptable) salt thereof wherein:

$L^1$, $L^2$ and $L^3$ are each independently selected from bond, or (e.g., $C_{1-6}$, such as $C_{1-3}$) alkyl (e.g., linear or branched);

A is N-amido, —NH—C(O)—, or —C(O)—NH—;

Ring B is selected from (e.g., $C_4$-$C_6$) cycloalkyl, (e.g., 5- or 6-membered) heterocyclyl, aryl (e.g., phenyl), heteroaryl (e.g., imidazolyl), and aralkyl (e.g., benzyl);

$R^x$ and $R^y$ are each independently selected from halogen, alkyl, haloalkyl, alkenyl, haloalkenyl, hydroxyl, alkoxy, haloalkoxy, nitro, —$NH_2$, alkylamino, dialkylamino, and haloalkylamino;

m is 0, 1, or 2; and n is 0 or 1.

In some embodiments, $L^1$, $L^2$ and $L^3$ are each independently a bond. In some embodiments, $L^1$, $L^2$ and $L^3$ are each independently linear $C_{1-6}$ alkyl. In some embodiments, $L^1$, $L^2$ and $L^3$ are each independently branched $C_{1-6}$ alkyl. In some embodiments, $L^1$, $L^2$ and $L^3$ are each independently linear $C_{1-3}$ alkyl. In some embodiments, $L^1$, $L^2$ and $L^3$ are each independently branched $C_{1-3}$ alkyl.

In some embodiments, A is N-amido. In some embodiments, A is —NH—C(O)—. In some embodiments, A is —C(O)—NH—.

In some embodiments, for a compound or salt of Formula (III), Ring B is selected from aryl (e.g., phenyl), heteroaryl (e.g., imidazolyl), and aralkyl (e.g., benzyl). In some embodiments, Ring B is selected from aryl (e.g., phenyl), and heteroaryl (e.g., imidazolyl). In some embodiments, Ring B is selected from phenyl and imidazolyl. In some embodiments, Ring B is

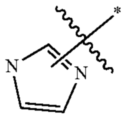

or

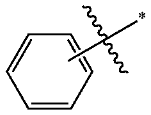

.

In some embodiments, Ring B is

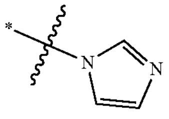

or

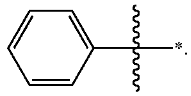

In some embodiments, $R^x$ is $C_1$-$C_3$ alkoxy. In some embodiments, $R^x$ is —$OCH_3$.

In some embodiments, m is 0. In some embodiments, m is 1. In some embodiments, n is 0.

In some embodiments, a compound having structural Formula (III) is selected from those set forth in Table 3, and salts thereof.

TABLE 3

Example Compounds of Formula (III)

| ID # | Chemical Structure | Chemical Name | Molecular Weight |
|---|---|---|---|
| III-1 | 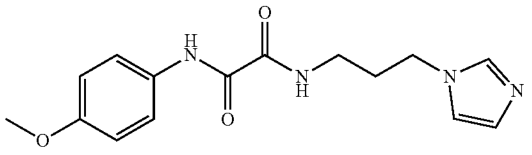 [SMILES: COc1ccc(NC(=O)C(=O)NCCCn2ccnc2)cc1] | N-(3-imidazol-1-ylpropyl)-N'-(4-methoxyphenyl)oxamide | 302.334 |
| III-2 | 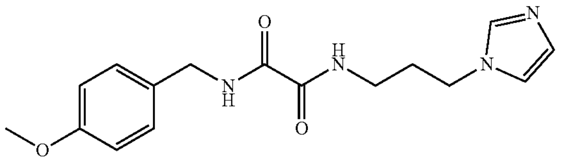 [SMILES: COc1ccc(CNC(=O)C(=O)NCCCn2ccnc2)cc1] | N-(3-imidazol-1-ylpropyl)-N'-[(4-methoxyphenyl)methyl]oxamide | 316.361 |
| III-3 | 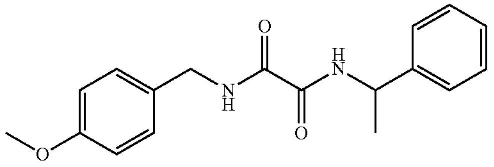 [SMILES: COc1ccc(CNC(=O)C(=O)NC(C)c2ccccc2)cc1] | N-[(4-methoxyphenyl)methyl]-N'-(1-phenylethyl)oxamide | 312.369 |
| III-4 | 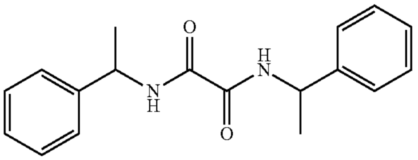 [SMILES: CC(NC(=O)C(=O)NC(C)c1ccccc1)c1ccccc1] | N,N'-bis(1-phenylethyl)oxamide | 296.370 |
| III-5 | 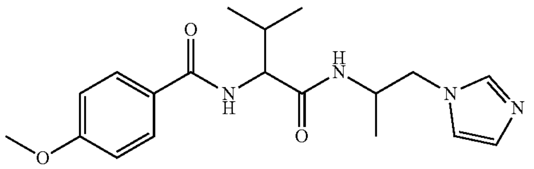 [SMILES: COc1ccc(C(=O)NC(C(=O)NC(C)Cn2ccnc2)C(C)C)cc1] | N-[1-(1-imidazol-1-ylpropan-2-ylamino)-3-methyl-1-oxobutan-2-yl]-4-methoxybenzamide | 358.442 |

Compounds of Formula (IV) and Salts Thereof

In certain aspects, disclosed herein is a compound represented by Formula (IV):

(IV)

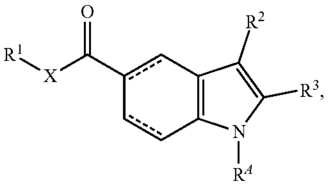

or a (e.g., pharmaceutically or cosmetically acceptable) salt thereof, wherein:

$R^1$ is selected from alkyl, or heterocycloalky, wherein the alkyl or heterocycloalkyl of $R^1$ is optionally substituted with one or more substituents independently selected from heterocycloalkyl (e.g.

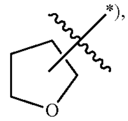

),

—C(O)$NR^{x1}R^{x2}$, alkoxy, —($C_1$-$C_3$ alkylene)-C(O)$OR^{y1}$, —C(O)$OR^{y2}$, and —$OR^z$; wherein:

$R^{x1}$, $R^{x2}$, $R^{y1}$, $R^{y2}$, and $R^z$ are each independently selected from H, alkyl, and haloalkyl; and X is —O—, —S—, or —$NR^B$—; $R^A$ is H, alkyl, or haloalkyl;

$R^2$ and $R^3$ are each independently selected from H, (e.g., $C_{1-6}$, such as $C_{1-3}$) alkyl (e.g., linear or branched); or alternatively, $R^2$ and $R^3$ together with the atoms to which they are attached to form (e.g., $C_4$-$C_6$) cycloalkyl or aryl (e.g., phenyl), wherein the cycloalkyl or aryl is optionally substituted with one or more substituents independently selected from halogen, alkyl, and haloalkyl, wherein the dotted lines indicate the presence of a single or double bond.

In some embodiments, the compound of Formula (IV) has a structural formula:

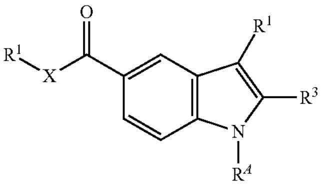

(e.q.,

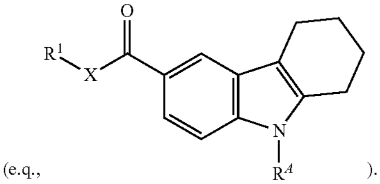

).

In some embodiments, the compound of Formula (IV) has a structural formula

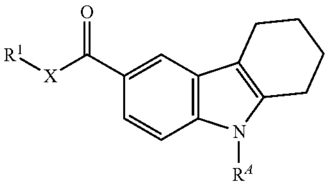

.

In some embodiments, the compound of Formula (IV) has a structural formula:

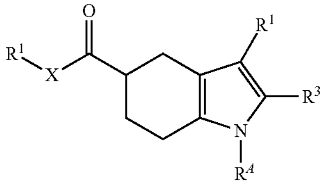

(e.q.,

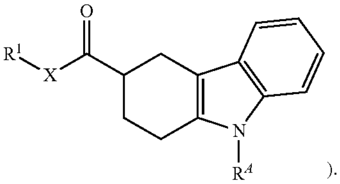

).

In some embodiments, the compound of Formula (IV) has a structural formula:

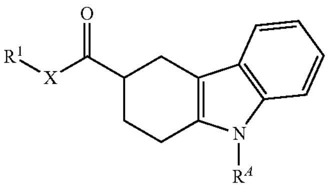

.

In some embodiments, X is —O—. In some embodiments, X is —$NR^B$—, optionally wherein $R^B$ is H.

In some embodiments, $R^1$ is selected from —$(CH_2)_a$C(O)OH, —$(CH_2)_aOCH_3$, —$(CH_2)_a$CH(OH)$CH_3$,

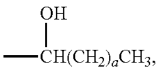

,

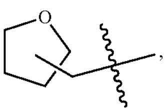

,

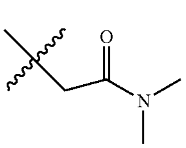

, and

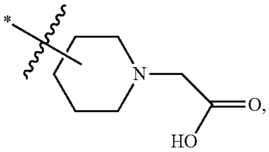

, wherein: a is 0, 1, 2, or 3. In some embodiments, $R^1$ is selected from —$(CH_2)_a$C(O)OH, —$(CH_2)_aOCH_3$, —$(CH_2)_a$CH(OH)$CH_3$,

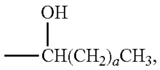,

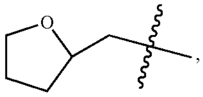,

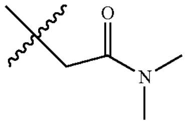, and

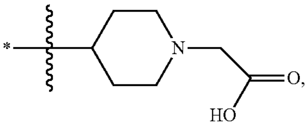, wherein: a is 0, 1, 2, or 3. In some embodiments, $R^1$ is selected from —$CH_2C(O)OH$, —$(CH_2)_2OCH_3$, $CH_2CH(OH)CH_3$,

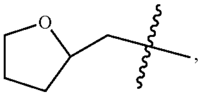,

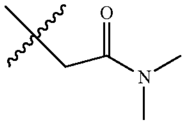, and

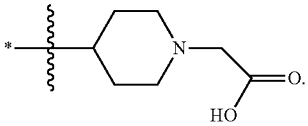.

In some embodiments, $R^{x1}$ and $R^{x2}$ are each independently $C_1$-$C_6$ (e.g., $C_1$-$C_3$) alkyl. In some embodiments, $R^{y1}$ is H. In some embodiments, $R^{y2}$ is H. In some embodiments, $R^z$ is H.

In some embodiments, $R^1$ is $C_{1-4}$ alkyl optionally substituted with one or more substituents independently selected from heterocycloalkyl (e.g.,

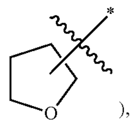),

—$C(O)NR^{x1}R^{x2}$, alkoxy, —($C_1$-$C_3$ alkylene)-$C(O)OR^{y1}$, —$C(O)OR^{y2}$, and —$OR^z$. In some embodiments, $R^1$ is $C_1$ alkyl optionally substituted with one or more heterocycloalkyl (e.g.,

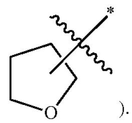).

In some embodiments, $R^1$ is $C_1$ alkyl optionally substituted with one heterocycloalkyl (e.g.,

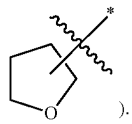).

In some embodiments, $R^1$ is

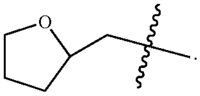 [SMILES: *CC1CCCO1].

In some embodiments, $C_1$ alkyl optionally substituted with one or more —$C(O)NR^{x1}R^{x2}$. In some embodiments, $R^1$ is $C_1$ alkyl optionally substituted with one or more —$C(O)NCH_3CH_3$. In some embodiments, $R^1$ is $C_1$ alkyl optionally substituted with one

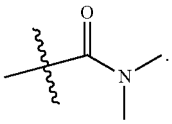 [SMILES: *C(=O)N(C)C].

In some embodiments, $R^1$ is

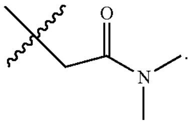 [SMILES: *CC(=O)N(C)C].

In some embodiments, $R^1$ is alkyl optionally substituted with one or more alkoxy. In some embodiments, $R^1$ is —$(CH_2)_aOCH_3$, wherein a is 0, 1, 2, or 3. In some embodiments, $R^1$ is —$(CH_2)OCH_3$. In some embodiments, $R^1$ is —$(CH_2)_2OCH_3$. In some embodiments, $R^1$ is —$(CH_2)_3OCH_3$. In some embodiments, $R^1$ is alkyl optionally substituted with one or more —$OR^z$. In some embodiments, $R^1$ is $C_3$ alkyl substituted with one or more —$OR^z$, wherein $R^z$ is H. In some embodiments, $R^1$ is $CH_2CH(OH)CH_3$. In some embodiments, $R^1$ is heterocycloalky optionally substituted with one or more substituents independently selected from heterocycloalkyl (e.g.,

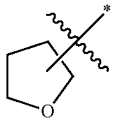),

—$C(O)NR^{x1}R^{x2}$, alkoxy, —($C_1$-$C_3$ alkylene)-$C(O)OR^{y1}$, —$C(O)OR^{y2}$, and —$OR^z$. In some embodiments, $R^1$ is heterocycloalky optionally substituted with one or more substituents independently selected from —($C_1$-$C_3$ alkylene)-$C(O)OR^{y1}$, wherein $R^{y1}$ is H. In some embodiments, the heterocycloalkyl is

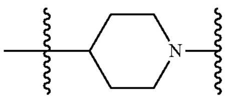 [SMILES: *C1CCN(*)CC1]

In some embodiments, $R^1$ is

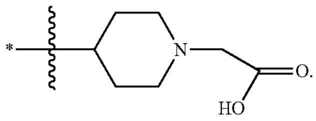

In some embodiments, $R^1$ is $C_1$ alkyl optionally substituted with one or more —C(O)O$R^{y2}$, wherein $R^{y2}$ is H. In some embodiments, $R^1$ is —CC(O)OH.

In some embodiments, $R^2$ and $R^3$ are each independently selected from $C_1$-$C_6$ alkyl. In some embodiments, $R^2$ and $R^3$ together with the atoms to which they are attached to form a $C_4$-$C_6$ cycloalkyl (e.g., cyclohexyl), optionally substituted with one or more substituents independently selected from halogen, alkyl, and haloalkyl. In some embodiments, $R^2$ and $R^3$ together with the atoms to which they are attached to form a cyclohexyl, optionally substituted with one or more substituents independently selected from halogen, alkyl, and haloalkyl. In some embodiments, $R^2$ and $R^3$ together with the atoms to which they are attached to form an aryl (e.g., phenyl), optionally substituted with one or more substituents independently selected from halogen, alkyl, and haloalkyl. In some embodiments, $R^2$ and $R^3$ together with the atoms to which they are attached to form a phenyl, optionally substituted with one or more substituents independently selected from halogen, alkyl, and haloalkyl. In some embodiments, $R^4$ is H.

In some embodiments, a compound having structural Formula (IV) is selected from those set forth in Table 4, and salts thereof.

TABLE 4

Example Compounds of Formula (IV)

| ID # | Chemical Structure | Chemical Name | Molecular Weight |
|---|---|---|---|
| IV-1 | 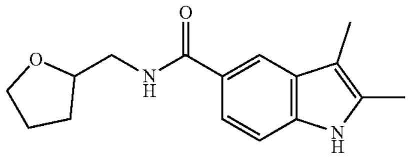 [SMILES: Cc1[nH]c2ccc(C(=O)NCC3CCCO3)cc2c1C] | 2,3-dimethyl-N-(oxolan-2-ylmethyl)-1H-indole-5-carboxamide | 272.348 |
| IV-2 | 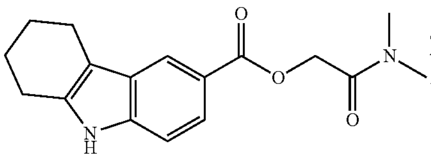 | [2-(dimethylamino)-2-oxoethyl] 6,7,8,9-tetrahydro-5H-carbazole-3-carboxylate | 300.358 |
| IV-3 | 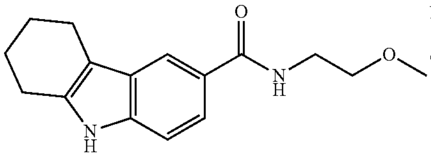 [SMILES: COCCNC(=O)c1ccc2[nH]c3c(c2c1)CCCC3] | N-(2-methoxyethyl)-6,7,8,9-tetrahydro-5H-carbazole-3-carboxamide | 272.348 |
| IV-4 | 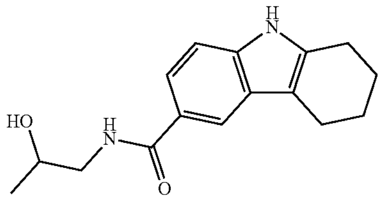 [SMILES: CC(O)CNC(=O)c1ccc2[nH]c3c(c2c1)CCCC3] | N-(2-hydroxypropyl)-6,7,8,9-tetrahydro-5H-carbazole-3-carboxamide | 272.348 |
| IV-5 | 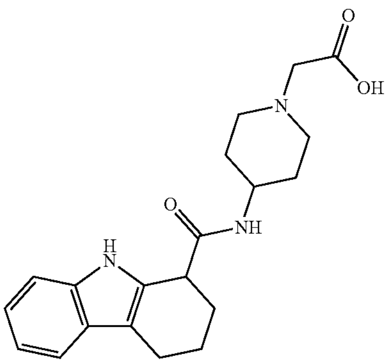 [SMILES: O=C(O)CN1CCC(NC(=O)C2CCCc3c2[nH]c2ccccc32)CC1] | 2-[4-(2,3,4,9-tetrahydro-1H-carbazole-1-carbonylamino)piperidin-1-yl]acetic acid | 355.438 |

TABLE 4-continued

| Example Compounds of Formula (IV) | | | |
|---|---|---|---|
| ID # | Chemical Structure | Chemical Name | Molecular Weight |
| IV-6 | 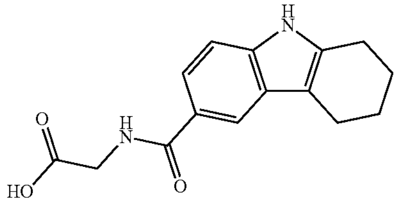 [SMILES: O=C(O)CNC(=O)c1ccc2[nH]c3c(c2c1)CCCC3] | 2-(6,7,8,9-tetrahydro-5H-carbazole-3-carbonylamino)acetic acid | 272.304 |

Compounds of Formula (V) and Salts Thereof

In certain aspects, disclosed herein is a compound represented by Formula (V):

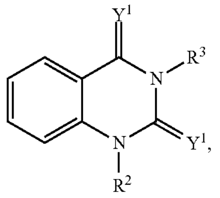

(V)

or a (e.g., pharmaceutically or cosmetically acceptable) salt thereof, wherein:

$Y^1$ is O, S or $NR^1$, wherein $R^1$ is H, alkyl, or haloalkyl;

$R^2$ is selected from H, alkyl, haloalkyl, alkenyl, haloalkenyl, aryl (e.g., phenyl), and aralkyl (e.g., benzyl); and $R^3$ is selected from H, alkyl, haloalkyl, $—(CH_2)_{m1}—OR^{a1}$, $—(CH_2)_{m2}—O—(CH_2)_{m3}—OR^{a2}$, $—(CH_2)_{m4}—NR^{b1}R^{b2}$, $(CH_2)_{m5}—C(O)OR^c$, wherein:

$R^{a1}$, $R^{a2}$, $R^{b1}$, $R^{b2}$, and $R^c$ are each independently selected from H, alkyl, and haloalkyl; and m1, m2, m3, m4, and m5 are each independently selected from 1, 2, 3, and 4.

In some embodiments, for a compound or salt of Formula (V), $Y^1$ is O or S. In some embodiments, $Y^1$ is O. In some embodiments, $R^{a1}$, $R^{a2}$, $R^{b1}$, $R^{b2}$, and $R^c$ are each independently $C_1$-$C_6$ alkyl, such as $C_1$-$C_3$ alkyl. In some embodiments, $R^{a1}$ is $C_1$ alkyl. In some embodiments, $R^{a1}$ is $C_2$ alkyl. In some embodiments, $R^{a1}$ is $C_3$ alkyl. In some embodiments, $R^{a2}$ is $C_1$ alkyl. In some embodiments, $R^{a2}$ is $C_2$ alkyl. In some embodiments, $R^{a2}$ is $C_3$ alkyl. In some embodiments, $R^{b1}$ is $C_1$ alkyl. In some embodiments, $R^{b1}$ is $C_2$ alkyl. In some embodiments, $R^{b1}$ is $C_3$ alkyl. In some embodiments, $R^{b2}$ is $C_1$ alkyl. In some embodiments, $R^{b2}$ is $C_2$ alkyl. In some embodiments, $R^{b2}$ is $C_3$ alkyl. In some embodiments, $R^c$ is $C_1$ alkyl. In some embodiments, $R^c$ is $C_2$ alkyl. In some embodiments, $R^c$ is $C_3$ alkyl. In some embodiments, $R^2$ is H.

In some embodiments, m1 is selected from 1, 2, 3, and 4. In some embodiments, m1 is 1. In some embodiments, m1 is 2. In some embodiments, m1 is 3. In some embodiments, m1 is 4. In some embodiments, m2 is selected from 1, 2, 3, and 4. In some embodiments, m2 is 1. In some embodiments, m2 is 2. In some embodiments, m2 is 3. In some embodiments, m2 is 4. In some embodiments, m3 is selected from 1, 2, 3, and 4. In some embodiments, m3 is 1. In some embodiments, m3 is 2. In some embodiments, m3 is 3. In some embodiments, m3 is 4. In some embodiments, m4 is selected from 1, 2, 3, and 4. In some embodiments, m4 is 1. In some embodiments, m4 is 2. In some embodiments, m4 is 3. In some embodiments, m4 is 4. In some embodiments, m5 is selected from 1, 2, 3, and 4. In some embodiments, m5 is 1. In some embodiments, m5 is 2. In some embodiments, m5 is 3. In some embodiments, m5 is 4.

In some embodiments, a compound having structural Formula (V) is selected from those set forth in Table 5, and salts thereof.

TABLE 5

| Example Compounds of Formula (V) | | | |
|---|---|---|---|
| ID # | Chemical Structure | Chemical Name | Molecular Weight |
| V-1 | 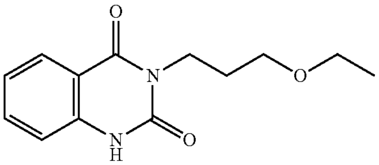 [SMILES: CCOCCCn1c(=O)[nH]c2ccccc2c1=O] | 3-(3-ethoxypropyl)-1H-quinazoline-2,4-dione | 248.282 |
| V-2 | 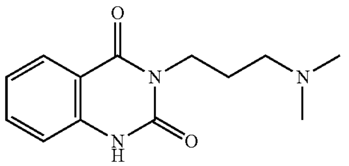 [SMILES: CN(C)CCCn1c(=O)[nH]c2ccccc2c1=O] | 3-[3-(dimethylamino)propyl]-1H-quinazoline-2,4-dione | 247.298 |

TABLE 5-continued

Example Compounds of Formula (V)

| ID # | Chemical Structure | Chemical Name | Molecular Weight |
|---|---|---|---|
| V-3 | 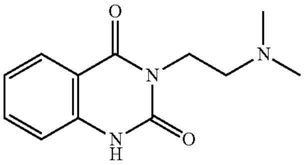 [SMILES: CN(C)CCn1c(=O)[nH]c2ccccc2c1=O] | 3-[2-(dimethylamino)ethyl]-1H-quinazoline-2,4-dione | 233.271 |
| V-4 | 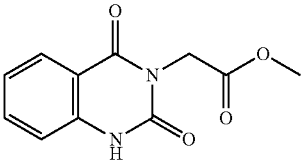 [SMILES: COC(=O)Cn1c(=O)[nH]c2ccccc2c1=O] | methyl 2-(2,4-dioxo-1H-quinazolin-3-yl)acetate | 234.211 |
| V-5 | 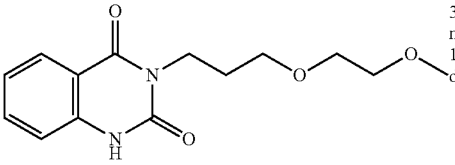 | 3-[3-(2-methoxyethoxy)propyl]-1H-quinazoline-2,4-dione | 278.308 |

Compounds of Formula (VI) and Salts Thereof

In certain aspects, disclosed herein is a compound represented by Formula (VI):

(VI)

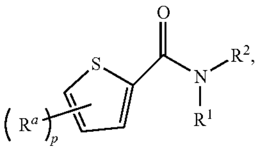

or a (e.g., pharmaceutically or cosmetically acceptable) salt thereof, wherein:

$R^a$ (when present) is each independently selected from alkyl, haloalkyl, alkenyl, haloalkenyl, and alkoxy;

one of $R^1$ and $R^2$ is H, or alkyl;

the other one of $R^1$ and $R^2$ is selected from H, alkyl, alkoxy, —($C_1$-$C_6$ alkylene)-C(O)$NR^{x1}$—($C_1$-$C_6$ alkylene)-aryl, and —($C_1$-$C_6$ alkylene)-C(O)$NR^{x2}$—($C_1$-$C_6$ alkyl), wherein $R^{x1}$ and $R^{x2}$ are each independently H, alkyl, or haloalkyl; and p is 0, 1, or 2.

In certain embodiments, for a compound or salt of Formula (VI), $R^{x1}$ is H. In some embodiments, $R^{x2}$ is H.

In some embodiments, one of $R^1$ and $R^2$ is H. In some embodiments, the other one of $R^1$ and $R^2$ is selected from $C_1$-$C_6$ (e.g., $C_1$-$C_3$) alkyl,

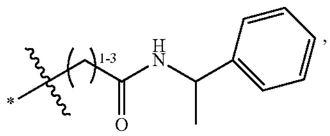

, and

-continued

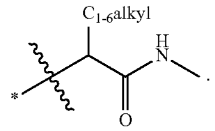

In some embodiments, the other one of $R^1$ and $R^2$ is selected from isopropyl,

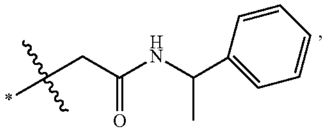

and

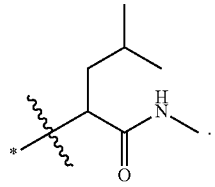

In some embodiments, the other one of $R^1$ and $R^2$ is isopropyl. In some embodiments, the other one of $R^1$ and $R^2$ is

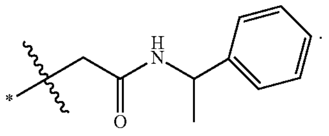

In some embodiments, the other one of $R^1$ and $R^2$ is

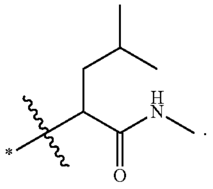

In some embodiments, p is 0. In some embodiments, p is 1.

In some embodiments, $R^a$ is $C_1$-$C_6$ (e.g., $C_1$-$C_3$) alkyl or $C_1$-$C_6$ (e.g., $C_1$-$C_3$) alkoxy. In some embodiments, $R^a$ is —$CH_3$. In some embodiments, $R^a$ is —$OCH_3$.

In some embodiments, a compound having structural Formula (VI) is selected from those set forth in Table 6, and salts thereof.

TABLE 6

Example Compounds of Formula (VI)

| ID # | Chemical Structure | Chemical Name | Molecular Weight |
|---|---|---|---|
| VI-1 | 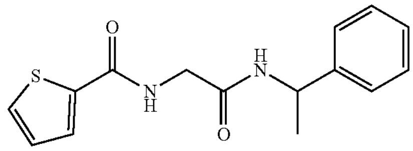 [SMILES: CC(NC(=O)CNC(=O)c1cccs1)c1ccccc1] | N-[2-oxo-2-(1-phenylethylamino)ethyl]thiophene-2-carboxamide | 288.372 |
| VI-2 | 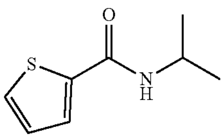 | 3-methyl-N-propan-2-ylthiophene-2-carboxamide | 183.276 |
| VI-3 | 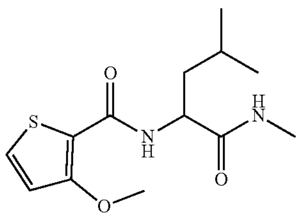 [SMILES: CNC(=O)C(CC(C)C)NC(=O)c1sccc1OC] | 3-methoxy-N-[4-methyl-1-(methylamino)-1-oxopentan-2-yl]thiophene-2-carboxamide | 284.381 |

Compounds of Formula (VII) and Salts Thereof

In certain aspects, disclosed herein is a compound represented by Formula (VII):

(VII)

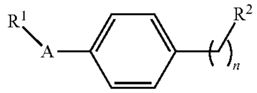

or a (e.g., pharmaceutically or cosmetically acceptable) salt thereof, wherein:

A is selected from 0, NH, S;

$R^1$ is selected from hydrogen, halogen, $C_{1-6}$ alkyl, $C_{1-6}$ haloalkyl, $C_{2-6}$ alkenyl, $C_{2-6}$ alkynyl, $C_{2-10}$ alkynyl, $C_{3-12}$ carbocycle, and 3- to 12-membered heterocycle;

$R^2$ is selected from 6- to 10-membered heterocycle, wherein the 6- to 10-membered heterocycle is optionally substituted with one or more substituents independently selected from halogen, $C_{1-6}$ alkyl, $C_{2-6}$ alkenyl, and $C_{2-6}$ alkynyl, $—OR^{11}$, $—SR^{11}$, $—NO_2$, =O, =NH, —CN, $—C(O)R^{11}$, $—C(O)OR^{11}$, $—OC(O)R^{11}$, $—OC(O)N(R^{11})_2$, $—NR^{11}S(O)_2R^{11}$, $—C(O)N(R^{11})_2$, $—N(R^{11})C(O)R^{11}$, $—N(R^{11})C(O)N(R^{11})_2$, $—N(R^{11})C(O)OR^{11}$, $—S(O)_2(R^{11})$, $—S(O)_2N(R^{11})_2$, $C_{1-10}$ alkyl, $C_3$-$C_{12}$ carbocycle and 5- to 12-membered heterocycle;

n is selected from 1, 2, 3, 4, 5, and 6;

each $R^{11}$ is independently selected at each occurrence from hydrogen; $C_{1-6}$ alkyl, $C_{2-6}$ alkenyl, $C_{2-6}$ alkynyl, and $C_{3-12}$ carbocycle, each of which is optionally substituted with one or more substituents selected from 3- to 6-membered heterocycle.

In some embodiments, A is oxygen. In some embodiments, $R^1$ is $C_{1-6}$ alkyl. In some embodiments, $C_{1-6}$ alkyl is $C_1$ alkyl. In some embodiments, $R^1$ is $—CH_3$.

In some embodiments, n is selected 1 and 3. In some embodiments, n is selected 1. In some embodiments, n is selected 3.

In some embodiments, the 6- to 10-membered heterocycle of $R^2$ is selected from pyran, pyridine, piperidine, imidazole, thiazole, dioxane, morpholine, pyrimidine, benzimidazole, piperazine, thiadiazine, oxepane, thiepine, azocine, indole, isoindole, indolizine, quinoline, isoquinoline, purine, cabazole, and dibesofuran. In some embodiments, the 6- to 10-membered heterocycle of $R^2$ is benzimidazole,

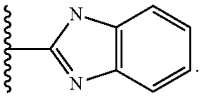 [SMILES: *c1nc2ccccc2[nH]1]

In some embodiments, the 6- to 10-membered heterocycle $R^2$ is piperazine,

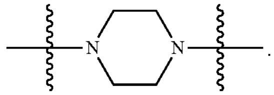

In some embodiments, piperazine is optionally substituted with one or more substituents independently selected from with =O and $—C(O)R^{11}$.

In some embodiments, $R^{11}$ is $C_{1-6}$ alkyl substituted with one or more substituents selected from 3- to 6-membered heterocycle. In some embodiments, $R^{11}$ is $C_1$ alkyl or $C_2$ alkyl. In some embodiments, the 3- to 6-membered heterocycle is

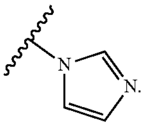

In some embodiments, each $R^2$ is selected from:

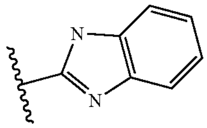

,

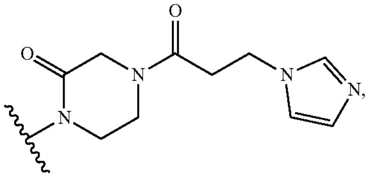

and

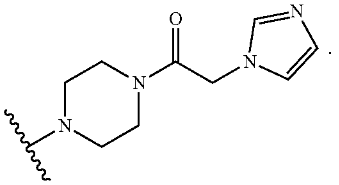

In some embodiments, a compound having structural Formula (VII) is selected from those set forth in Table 7, and salts thereof.

TABLE 7

Example Compounds of Formula (VII)

| ID # | Chemical Structure | Chemical Name | Molecular Weight |
|---|---|---|---|
| VII-32 | 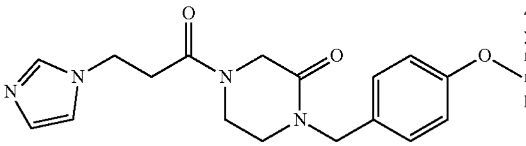 [SMILES: COc1ccc(CN2CCN(C(=O)CCn3ccnc3)CC2=O)cc1] | 4-(3-imidazol-1-ylpropanoyl)-1-[(4-methoxyphenyl) methyl] piperazin-2-one | 342.399 |

TABLE 7-continued

| Example Compounds of Formula (VII) | | | |
|---|---|---|---|
| ID # | Chemical Structure | Chemical Name | Molecular Weight |
| VII-33 | 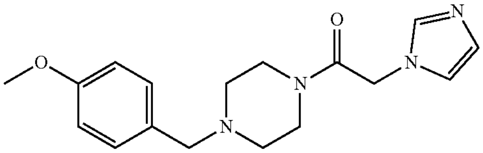 [SMILES: COc1ccc(CN2CCN(C(=O)Cn3ccnc3)CC2)cc1] | 2-imidazol-1-yl-1-[4-[(4-methoxyphenyl) methyl]piperazin-1-yl]ethanone | 314.389 |
| VII-34 | 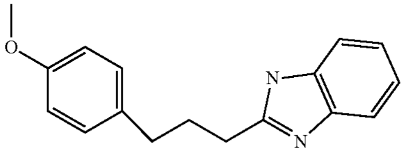 [SMILES: COc1ccc(CCCc2nc3ccccc3[nH]2)cc1] | 2-[3-(4-methoxyphenyl) propyl]-1H-benzimidazole | 266.344 |

Other Compounds and Salts Thereof

In some embodiments, a compound disclosed herein is selected from those set forth in Table 8, and salts thereof.

TABLE 8

| Example Other Compounds | | | |
|---|---|---|---|
| ID # | Chemical Structure | Chemical Name | Molecular Weight |
| VII-1 | 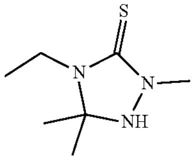 | 4-ethyl-2,5,5-trimethyl-1,2,4-triazolidine-3-thione | 173.285 |
| VII-2 | 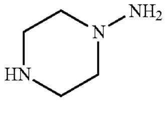 | piperazin-1-amine | 101.153 |
| VII-3 | 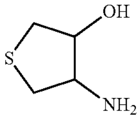 | 4-aminothiolan-3-ol | 119.189 |
| VII-4 | 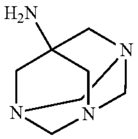 | 1,3,5-triazatricyclo[3.3.1.1 3,7]decan-7-amine | 154.217 |
| VII-5 | 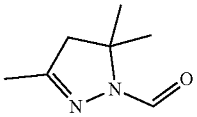 | 3,5,5-trimethyl-4H-pyrazole-1-carbaldehyde | 140.186 |
| VII-6 | 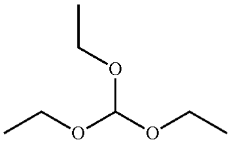 | diethoxymethoxy-ethane | 148.202 |

TABLE 8-continued

Example Other Compounds

| ID # | Chemical Structure | Chemical Name | Molecular Weight |
|---|---|---|---|
| VII-7 | 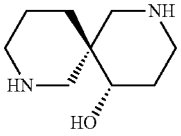 [SMILES: O[C@H]1CCNC[C@]12CCCNC2] | (5S,6R)-2,8-diazaspiro[5.5] undecan-5-ol | 170.256 |
| VII-8 | 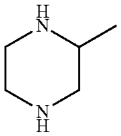 | 2-methylpiperazine | 100.165 |
| VII-9 | 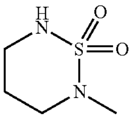 | 2-methyl-1,2,6-thiadiazinane 1,1-dioxide | 150.203 |
| VII-10 | 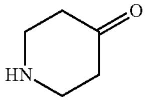 | piperidin-4-one | 99.133 |
| VII-11 | 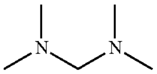 | N,N,N',N'-tetramethylmethane diamine | 102.181 |
| VII-12 | 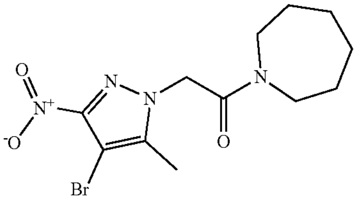 | 1-(azepan-1-yl)-2-(4-bromo-5-methyl-3-nitropyrazol-1-yl)ethanone | 345.197 |
| VII-13 | 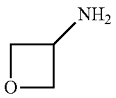 | oxetan-3-amine | 73.095 |
| VII-14 | 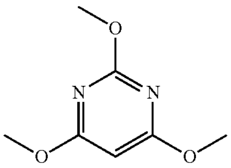 | 2,4,6-trimethoxypyrimidine | 170.168 |
| VII-15 | 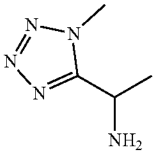 | 1-(1-methyltetrazol-5-yl)ethanamine | 127.151 |

TABLE 8-continued

Example Other Compounds

| ID # | Chemical Structure | Chemical Name | Molecular Weight |
|---|---|---|---|
| VII-16 | 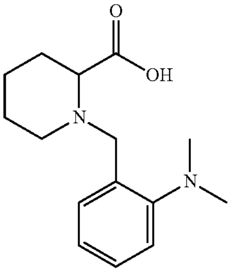 [SMILES: CN(C)c1ccccc1CN1CCCCC1C(=O)O] | 1-[[2-(dimethylamino)phenyl]methyl]piperidine-2-carboxylic acid | 262.353 |
| VII-17 | 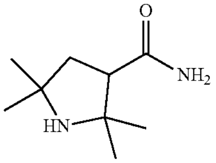 | 2,2,5,5-tetramethylpyrrolidine-3-carboxamide | 170.256 |
| VII-18 | 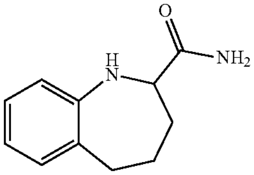 [SMILES: NC(=O)C1CCCc2ccccc2N1] | 2,3,4,5-tetrahydro-1H-1-benzazepine-2-carboxamide | 190.246 |
| VII-19 | 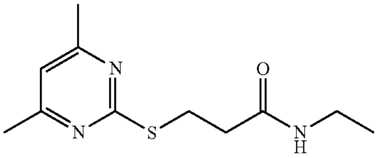 [SMILES: CCNC(=O)CCSc1nc(C)cc(C)n1] | 3-(4,6-dimethylpyrimidin-2-yl)sulfanyl-N-ethylpropanamide | 239.344 |
| VII-20 | 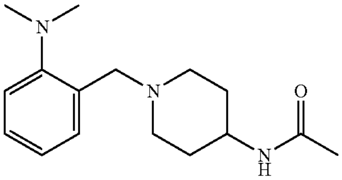 [SMILES: CC(=O)NC1CCN(Cc2ccccc2N(C)C)CC1] | N-[1-[[2-(dimethylamino)phenyl]methyl]piperidin-4-yl]acetamide | 275.396 |
| VII-21 | 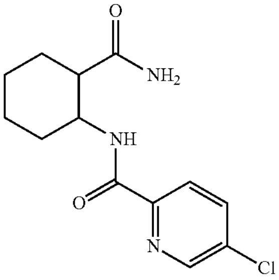 [SMILES: NC(=O)C1CCCCC1NC(=O)c1ccc(Cl)cn1] | N-(2-carbamoylcyclohexyl)-5-chloropyridine-2-carboxamide | 281.743 |
| VII-22 | 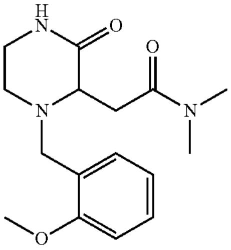 [SMILES: COc1ccccc1CN1CCNC(=O)C1CC(=O)N(C)C] | 2-[1-[(2-methoxyphenyl)methyl]-3-oxopiperazin-2-yl]-N,N-dimethylacetamide | 305.378 |

TABLE 8-continued

| Example Other Compounds | | | |
|---|---|---|---|
| ID # | Chemical Structure | Chemical Name | Molecular Weight |
| VII-23 | 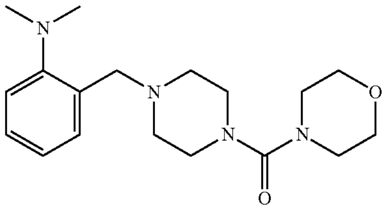 [SMILES: CN(C)c1ccccc1CN1CCN(C(=O)N2CCOCC2)CC1] | [4-[[2-(dimethylamino)phenyl]methyl]piperazin-1-yl]-morpholin-4-ylmethanone | 332.448 |
| VII-24 | 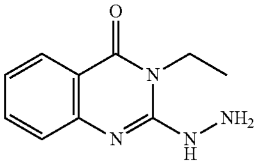 | 3-ethyl-2-hydrazinylquinazolin-4-one | 204.233 |
| VII-25 | 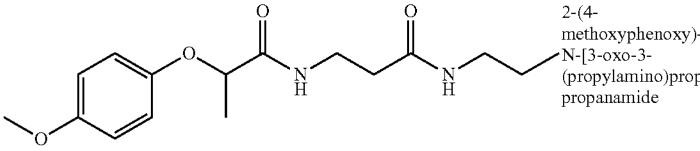 | 2-(4-methoxyphenoxy)-N-[3-oxo-3-(propylamino)propyl]propanamide | 308.378 |
| VII-26 | 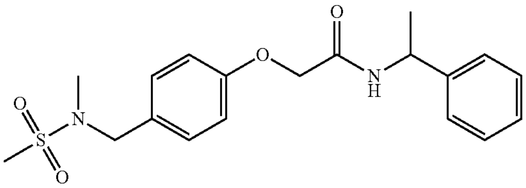 [SMILES: CC(NC(=O)COc1ccc(CN(C)S(C)(=O)=O)cc1)c1ccccc1] | 2-[4-[[methyl(methylsulfonyl)amino]methyl]phenoxy]-N-(1-phenylethyl)acetamide | 376.478 |
| VII-27 | 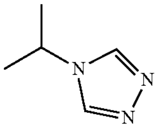 | 4-propan-2-yl-1,2,4-triazole | 111.148 |
| VII-28 | 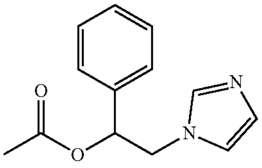 [SMILES: CC(=O)OC(Cn1ccnc1)c1ccccc1] | (2-imidazol-1-yl-1-phenylethyl) acetate | 230.267 |
| VII-29 | 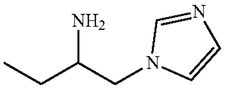 | 1-imidazol-1-ylbutan-2-amine | 139.202 |
| VII-30 | 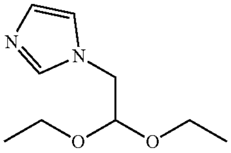 | 1-(2,2-diethoxyethyl)imidazole | 184.239 |

TABLE 8-continued

Example Other Compounds

| ID # | Chemical Structure | Chemical Name | Molecular Weight |
|---|---|---|---|
| VII-31 | 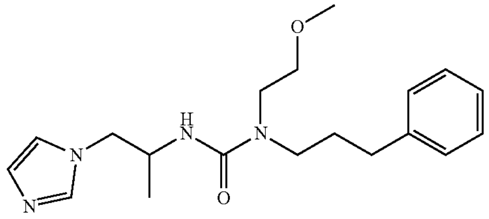 [SMILES: COCCN(CCCc1ccccc1)C(=O)NC(C)Cn1ccnc1] | 3-(1-imidazol-1-ylpropan-2-yl)-1-(2-methoxyethyl)-1-(3-phenylpropyl)urea | 344.459 |
| VII-35 | 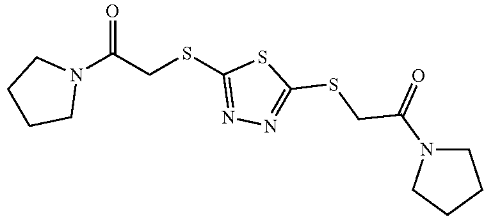 [SMILES: O=C(CSc1nnc(SCC(=O)N2CCCC2)s1)N1CCCC1] | 2-[5-(2-oxo-2-pyrrolidin-1-ylethyl)sulfanyl-1,3,4-thiadiazol-2-yl]sulfanyl]-1-pyrrolidin-1-ylethanone | 372.541 |
| VII-36 | 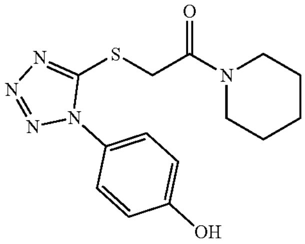 [SMILES: O=C(CSc1nnnn1-c1ccc(O)cc1)N1CCCCC1] | 2-[1-(4-hydroxyphenyl) tetrazol-5-yl]sulfanyl-1-piperidin-1-ylethanone | 319.390 |
| VII-37 | 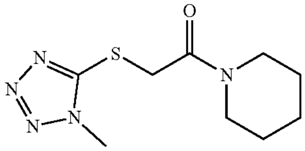 [SMILES: Cn1nnnc1SCC(=O)N1CCCCC1] | 2-(1-methyltetrazol-5-yl)sulfanyl-1-piperidin-1-ylethanone | 241.320 |
| VII-38 | 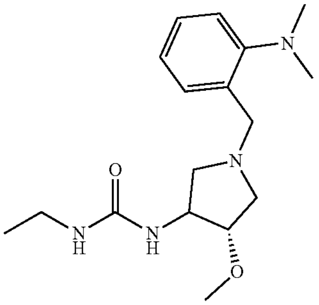 [SMILES: CCNC(=O)NC1CN(Cc2ccccc2N(C)C)C[C@@H]1OC] | 1-[(4S)-1-[[2-(dimethylamino) phenyl]methyl]-4-methoxypyrrolidin-3-yl]-3-ethylurea | 320.437 |

In some embodiments, a compound disclosed herein is selected from those (or any subset thereof) set forth in any one or combination of Tables 1 through 8, and salts thereof.

Compounds of the present invention may also include crystalline and amorphous forms of those compounds, pharmaceutically acceptable salts, and active metabolites of these compounds having the same type of activity, including, for example, polymorphs, pseudopolymorphs, solvates, hydrates, unsolvated polymorphs (including anhydrates), conformational polymorphs, and amorphous forms of the compounds, as well as mixtures thereof.

Included in the present disclosure are salts, particularly pharmaceutically acceptable salts, of the compounds described herein. The compounds of the present disclosure that possess a sufficiently acidic, a sufficiently basic, or both functional groups, can react with any of a number of inorganic bases, and inorganic and organic acids, to form a salt. Alternatively, compounds that are inherently charged, such as those with a quaternary nitrogen, can form a salt with an appropriate counterion, e.g., a halide such as bromide, chloride, or fluoride, particularly bromide.

The compounds described herein may in some cases exist as diastereomers, enantiomers, or other stereoisomeric forms. The compounds presented herein include all diastereomeric, enantiomeric, and epimeric forms as well as the appropriate mixtures thereof. Separation of stereoisomers may be performed by chromatography or by forming diastereomers and separating by recrystallization, or chromatography, or any combination thereof. (Jean Jacques, Andre Collet, Samuel H. Wilen, "Enantiomers, Racemates and Resolutions", John Wiley and Sons, Inc., 1981, herein incorporated by reference for this disclosure). Stereoisomers may also be obtained by stereoselective synthesis.

The methods and compositions described herein include the use of amorphous forms as well as crystalline forms (also known as polymorphs). The compounds described herein may be in the form of pharmaceutically acceptable salts. As well, in some embodiments, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

Synthetic chemistry transformations and methodologies useful in synthesizing the compounds described herein are known in the art and include, for example, those described in R. Larock, *Comprehensive Organic Transformations* (1989); T. W. Greene and P. G. M. Wuts, *Protective Groups in Organic Synthesis,* 2d. Ed. (1991); L. Fieser and M. Fieser, *Fieser and Fieser's Reagents for Organic Synthesis* (1994); and L. Paquette, ed., *Encyclopedia of Reagents for Organic Synthesis* (1995).

Compositions

The disclosure provides compositions of compounds disclosed herein and salts thereof.

In some embodiments, the composition is for preventing or treating a skin condition, disorder, or disease comprising a compound having a structure of Formula (I), (II), (III), (IV), (V), (VI), (VII), or Table 8. In some embodiments, the composition is for treating a skin condition, disorder, or disease comprising a compound having a structure of Formula (I), (II), (III), (IV), (V), (VI), (VII), or Table 8. In some embodiments, a weight % of the compound in the composition ranges from about 0.05% to about 10.0% by weight relative to the total weight of the composition. In some embodiments, a weight % of the compound in the composition ranges from about 0.01% to about 5%. In some embodiments, a weight % of the compound in the composition ranges from about 0.01% to about 2.0%. In some embodiments, a weight % of the compound in the composition ranges from about 0.01% to about 10% by weight relative to the total weight of the composition. In some embodiments, a weight % of the compound in the composition is at least about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by weight relative to the total weight of the composition. In some embodiments, a weight % of the compound in the composition is at most about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by weight relative to the total weight of the composition. In some embodiments, a weight % of the compound in the composition ranges from about 0.01 to 10, 0.02 to 9, 0.03 to 8, 0.04 to 7, 0.05 to 6, 0.06 to 5, 0.07 to 4, 0.08 to 3, 0.09 to 2, 0.1 to 1, 0.2 to 0.9, 0.3 to 0.8, 0.4 to 0.7, or 0.5 to 0.6% by weight relative to the total weight of the composition.

The composition disclosed herein may further comprise at least one additive selected from, but are not limited to, the group consisting of water, preservatives, antioxidants, sunscreen agents, surfactants, emulsifiers, opacifying agents, volatiles, propellants, liquid vehicles, carriers, salts, pH adjusting agents, neutralizing agents, buffers, natural extracts, humectants, fragrances, perfumes, oils, emollients, lubricants, butters, penetrants, thickeners, viscosity modifiers, polymers, resins, film formers, absorbents, oils, moisturizers, whitening agents, anti-wrinkle agents, and acne relievers, atopic reliever, sunscreen, hair restorer, vitamins and derivatives, amino acids or polypeptides, anti-inflammatory agents, female hormones, exfoliating agents, fungicides, placenta, allantoin, yeast extract, collagen, elastin, DHA, EPA, ceramide, and combinations thereof, in order to achieve a close approximation to commercially available product forms. The composition disclosed herein for preventing or treating a skin condition, disorder, or disease may be formulated in any suitable physical form. For example, in some embodiments, the suitable physical forms include, but not limited to, toner, emulsion, cream, gel, conditioner, soap, serum, spray, liquids with low to moderate viscosity, lotions, milks, mousses, oil, and the like. In some embodiments, the composition is formulated to be administered by misting, wiping, rubbing, wetting, dropping, or squirting.

In some embodiments, the composition is a pharmaceutical composition. In some embodiments, the pharmaceutical composition comprises a compound having a structure of Formula (I), (II), (III), (IV), (V), (VI), or (VII), or a salt thereof. In some embodiments, the pharmaceutical composition comprises a compound having a structure in Table 1, Table 2, Table 3, Table 4, Table 5, Table 6, Table 7, or Table 8, or a salt thereof. The pharmaceutical composition may further comprise at least one additive selected from the group consisting of pharmaceutically acceptable carriers, excipients, adjuvants, diluents, and combinations thereof, in order to achieve a close approximation to commercially available product forms.

In some embodiments, the composition is a cosmetic composition. In some embodiments, the cosmetic composition comprises a compound having a structure of Formula (I), (II), (III), (IV), (V), (VI), or (VII), or a salt thereof. In some embodiments, the cosmetic composition comprises a compound having a structure in Table 1, Table 2, Table 3, Table 4, Table 5, Table 6, Table 7, or Table 8, or a salt thereof. The cosmetic composition may further comprise at least one additive selected from the group consisting of cosmetically acceptable carriers, excipients, adjuvants, diluents, and combinations thereof, in order to achieve a close approximation to commercially available product forms. The composition may be formulated as a liquid solution. The cosmetic composition disclosed herein may be formulated in any suitable physical form. For example, in some embodiments, the suitable physical forms include, but not limited to, toner, emulsion, cream, gel, conditioner, soap, serum, spray, liquids with low to moderate viscosity, lotions, milks, mousses, oil, and the like. In some embodiments, the composition may be used as a spray. In some embodiments, the composition may be used as a mist.

In some embodiments, non-limiting examples of the skin include face skin, elbow skin, neck skin, hand skin, skin around a joint, or combinations thereof. In some embodiments, the face skin comprises skin of forehead, temple, malar area, nasolabial fold, marionette line, chin, mandible, midface, preauricular zone, periorbital hollow, cheek, jaw contour, lip, or any combination of thereof.

In some embodiments, the composition disclosed herein prevents or reduces wrinkle(s) or fine line(s). In some embodiments, the compositions disclosed herein increases skin tightness. In some embodiments, the compositions disclosed herein fades age spot(s). In some embodiments, the compositions disclosed herein softens rough skin patch(es). In some embodiments, the compositions disclosed herein moisturizes/hydrates skin. In some embodiments, the compositions disclosed herein protects skin from ultraviolet damage. In some embodiments, the compositions disclosed herein increases skin collagen production or collagen-depositing cell proliferation. In some embodiments, the compositions disclosed herein increases fibroblast proliferation. In some embodiments, the compositions disclosed herein heals wound(s).

Non-limiting examples of the composition are shown in Table 9 to Table 13. The composition may include any aspect or combination of aspects from any of these tables. A, B, C, D, and E in Tables 9 to 13 represent example ranges of percent weights of each ingredient. For instance, A refers to values less than about 0.5%, B refers to values equal to or larger than about 0.5% and less than about 2%, C represents values equal to or larger than about 2% and less than about 10%, and D refers to values equal to or larger than about 10%. Based on these examples, a composition may include any aspect in Tables 9 to 13 in an amount shown therein.

TABLE 9

| Example of composition | |
|---|---|
| Ingredient | % Weight |
| Water | D |
| Glycerin | C |
| DMI | C |
| Ethoxydiglycol | C |
| Polyglyceryl-4 Caprate | B |
| Compound disclosed herein | B |
| Caprylic/Capric Triglyceride | C |
| Isostearyl Isostearate | C |
| Lauryl Lactate | C |
| Sucrose Stearate | C |
| Polyglyceryl-4 Laurate/Sebacate (and) Polyglyceryl-6 Caprylate/Caprate (and) Aqua | C |
| Polyacrylate Crosspolymer-6 | B |
| Vinyl Dimethicone/Methicone Silsesquioxane Crosspolymer | B |
| Phenoxyethanol | B |
| Caprylhydroxamic Acid, 1,2-Hexanediol, Propanediol | B |

TABLE 10

| Example of composition | |
|---|---|
| Ingredient | % Weight |
| Aqua/Eau/Water | D |
| Propanediol | C |
| Glycerin | C |
| Caprylic/Capric Triglyceride | C |
| Isostearyl Isostearate | C |
| Lauryl Lactate | C |
| Dicaprylyl Carbonate | C |
| Polyacrylamide & C13-14 Isoparaffin & Laureth-7 | C |
| Dimethyl Isosorbide | C |
| Ethoxydiglycol | C |
| Polyglyceryl-4 Caprate | B |
| Compound disclosed herein | B |
| Phenoxyethanol | B |
| Ethylhexylglycerin | A |
| Polymethylsilsesquioxane | B |
| Fragrance | A |

TABLE 11

| Example of composition | |
|---|---|
| Ingredient | % Weight |
| Aqua/Eau/Water | D |
| Xanthan Gum | A |
| Propanediol | C |
| Glycerin | C |
| Caprylic/Capric Triglyceride | C |
| Isostearyl Isostearate | C |
| Lauryl Lactate | C |
| Dicaprylyl Carbonate | C |
| Cetearyl Alcohol (and) Cetaryl Glucoside | C |
| Arachidyl Alcohol (and) Behenyl Alcohol (and) Arachidyl Glucoside | B |
| Glyceryl Stearate | C |
| Dimethyl Isosorbide | C |
| Ethoxydiglycol | C |
| Polyglyceryl-4 Caprate | B |
| Polyacrylate Crosspolymer-6 | B |
| Compound disclosed herein | B |
| Phenoxyethanol | B |
| Chlorphenesin | A |
| Disodium EDTA | A |
| Vinyl Dimethicone/Methicone Silsesquioxane Crosspolymer | B |
| Fragrance | A |

TABLE 12

| Example of composition | |
|---|---|
| Ingredient | % Weight |
| Aqua/Eau/Water | D |
| Propanediol | C |
| Glycerin | C |
| Sclerotium Gum | A |
| Caprylic/Capric Triglyceride | C |
| Isostearyl Isostearate | C |
| Lauryl Lactate | C |
| Dicaprylyl Carbonate | C |
| Behenyl Alcohol | C |
| Stearyl Alcohol | C |
| Potassium Cetyl Phosphate | B |
| Dimethyl Isosorbide | C |
| Ethoxydiglycol | C |
| Polyglyceryl-4 Caprate | B |
| Compound disclosed herein | B |
| Phenoxyethanol | B |
| Ethylhexylglycerin | A |
| Nylon-12 | B |
| Fragrance | A |

TABLE 13

| Example of composition | |
|---|---|
| Ingredient | % Weight |
| Aqua/Eau/Water | D |
| Propanediol | C |
| Glycerin | C |
| Caprylic/Capric Triglyceride | C |
| Isostearyl Isostearate | C |
| Lauryl Lactate | C |
| Dicaprylyl Carbonate | C |
| Polyacrylamide & C13-14 Isoparaffin & Laureth-7 | C |
| Dimethyl Isosorbide | C |
| Ethoxydiglycol | C |
| Polyglyceryl-4 Caprate | B |

TABLE 13-continued

| Example of composition | |
|---|---|
| Ingredient | % Weight |
| Compound disclosed herein | B |
| Phenoxyethanol | B |
| Ethylhexylglycerin | A |
| Boron Nitride | B |
| Fragrance | A |

In Tables 9-13, the "Compound disclosed herein" may include a compound having a structure of Formula (I), (II), (III), (IV), (V), (VI), (VII), or Table 8, or a salt thereof. In Tables 9-13, the "Compound disclosed herein" may include a compound having a structure in Table 1, Table 2, Table 3, Table 4, Table 5, Table 6, Table 7, or Table 8, or a salt thereof.

Disclosed herein, in some embodiments, are formulations that include an aspect or combination of aspects in any of Tables 9-13. The aspect or combination of aspects in any of Tables 9-13 may each comprise 0.001%, 0.002%, 0.003%, 0.004%, 0.005%, 0.006%, 0.007%, 0.008%, 0.009%, 0.01%, 0.02%, 0.03%, 0.04%, 0.05%, 0.06%, 0.07%, 0.08%, 0.09%, or 0.1%, or a range defined by any two of the aforementioned percentages, of the composition. The percentage may be weight/weight or weight/volume. The aspect or combination of aspects in any of Tables 9-13 may each comprise about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, or about 0.1%, or a range defined by any two of the aforementioned percentages, of the composition. The aspect or combination of aspects in any of Tables 9-13 may each comprise at least 0.001%, at least 0.002%, at least 0.003%, at least 0.004%, at least 0.005%, at least 0.006%, at least 0.007%, at least 0.008%, at least 0.009%, at least 0.01%, at least 0.02%, at least 0.03%, at least 0.04%, at least 0.05%, at least 0.06%, at least 0.07%, at least 0.08%, at least 0.09%, or at least 0.1% of the composition. The aspect or combination of aspects in any of Tables 9-13 may each comprise no greater than 0.001%, no greater than 0.002%, no greater than 0.003%, no greater than 0.004%, no greater than 0.005%, no greater than 0.006%, no greater than 0.007%, no greater than 0.008%, no greater than 0.009%, no greater than 0.01%, no greater than 0.02%, no greater than 0.03%, no greater than 0.04%, no greater than 0.05%, no greater than 0.06%, no greater than 0.07%, no greater than 0.08%, no greater than 0.09%, or no greater than 0.1% of the composition. The aspect or combination of aspects in any of Tables 9-13 may each comprise 0.1%, 0.2%, 0.3%, 0.4%, 0.5%, 0.6%, 0.7%, 0.8%, 0.9%, 1%, 2.5%, 5%, 7.5%, 10%, 15%, 20%, 25%, 30%, 35%, 40%, 45%, 50%, 55%, 60%, 65%, 70%, 75%, 80%, 85%, 90%, 95%, or 100%, or a range defined by any two of the aforementioned percentages, of the composition. The percentage may be weight/weight or weight/volume. The aspect or combination of aspects in any of Tables 9-13 may each comprise about 0.1%, about 0.2%, about 0.3%, about 0.4%, about 0.5%, about 0.6%, about 0.7%, about 0.8%, about 0.9%, about 1%, about 2.5%, about 5%, about 7.5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, or a range defined by any two of the aforementioned percentages, of the composition. The aspect or combination of aspects in any of Tables 9-13 may each comprise at least 0.1%, at least 0.2%, at least 0.3%, at least 0.4%, at least 0.5%, at least 0.6%, at least 0.7%, at least 0.8%, at least 0.9%, at least 1%, at least 2.5%, at least 5%, at least 7.5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, or at least 95%, of the composition. The aspect or combination of aspects in any of Tables 9-13 may each comprise no greater than 0.1%, no greater than 0.2%, no greater than 0.3%, no greater than 0.4%, no greater than 0.5%, no greater than 0.6%, no greater than 0.7%, no greater than 0.8%, no greater than 0.9%, no greater than 1%, no greater than 2.5%, no greater than 5%, no greater than 7.5%, no greater than 10%, no greater than 15%, no greater than 20%, no greater than 25%, no greater than 30%, no greater than 35%, no greater than 40%, no greater than 45%, no greater than 50%, no greater than 55%, no greater than 60%, no greater than 65%, no greater than 70%, no greater than 75%, no greater than 80%, no greater than 85%, no greater than 90%, or no greater than 95%, of the composition.

Methods

Also provided herein include methods for skin treatment with the compound(s) or salt(s) disclosed herein.

In certain aspects, disclosed herein is a method for preventing or treating a skin condition, disorder, or disease (whether or not a diagnosis of the skin condition, disorder, or disease has been made). In some embodiments, the method is for treating a skin condition, disorder, or disease. In some embodiments, the method comprises administering to a subject in need thereof a composition comprising a compound or salt described herein, or a composition described herein. The compound(s) or salt(s) thereof may have a structural Formula of (I), (II), (III), (IV), (V), (VI), (VII), or Table 8. The compound(s) or salt(s) thereof may be selected from those set forth in any one of Tables 1-8, or any subset thereof, or any combination thereof. In some embodiments, the method includes use, administration, or application of a compound having a structure of Formula (I), (II), (III), (IV), (V), (VI), or (VII), or a salt thereof. In some embodiments, the method includes use, administration, or application of a compound having a structure in Table 1, Table 2, Table 3, Table 4, Table 5, Table 6, Table 7, or Table 8, or a salt thereof.

A diagnosis of skin condition, disorder, or disease may or may not have been made. In some embodiments of any method described herein, the subject may have been diagnosed with skin condition, disorder, or disease. In some embodiments of any method described herein, the subject may not have been diagnosed with skin condition, disorder, or disease.

In some embodiments, the method comprises administering the composition to a skin area of said subject. In some embodiments, the skin area is face skin, elbow skin, neck skin, hand skin, or skin around a joint. In some embodiments, the face skin comprises skin of forehead, temple, malar area, nasolabial fold, marionette line, chin, mandible, midface, preauricular zone, periorbital hollow, cheek, jaw contour, lip, or any combination of thereof.

In some embodiments, the method prevents or reduces wrinkle(s) or fine line(s). In some embodiments, the method increases skin tightness. In some embodiments, the method fades age spot(s). In some embodiments, the method softens rough skin patch(es). In some embodiments, the method moisturizes/hydrates skin. In some embodiments, the method protects skin from ultraviolet damage. In some embodiments, the method increases skin collagen production or collagen-depositing cell proliferation. In some embodiments, the method increases fibroblast proliferation. In some embodiments, the method heals wound(s).

In some embodiments, the method comprises administering the composition to a skin area of said subject. In some embodiments, the composition is a pharmaceutical composition. In some embodiments, the pharmaceutical composition may further comprise at least one additive selected from the group consisting of pharmaceutically acceptable carriers, excipients, adjuvants, diluents, and combinations thereof, in order to achieve a close approximation to commercially available product forms.

In some embodiments, the pharmaceutical composition is administered one to three times a day. In some embodiments, the pharmaceutical composition is administered once a day. In some embodiments, the pharmaceutical composition is administered two times a day. In some embodiments, the pharmaceutical composition is administered three times a day. In some embodiments, the pharmaceutical composition is administered every other day. In some embodiments, the pharmaceutical composition is administered for at least two consecutive days. In some embodiments, the pharmaceutical composition is administered for at least three consecutive days. In some embodiments, the pharmaceutical composition is administered for at least four consecutive days. In some embodiments, the pharmaceutical composition is administered for at least five consecutive days. In some embodiments, the pharmaceutical composition is administered for at least seven consecutive days.

In some embodiments, the pharmaceutical composition is administered at least for about 2 days, 3 days, 5 days, 7 days, 10 days, 15 days, 20 days, 30 days, 50 days, 60 days, 80 days, 90 days, 5 months, 6 months, 7 months, 8 months, 9 months, 10 months, 11 months, a year, 2 years, or 3 years. In some embodiments, the pharmaceutical composition is administered at most for about 2 days, 3 days, 5 days, 7 days, 10 days, 15 days, 20 days, 30 days, 50 days, 60 days, 80 days, 90 days, 5 months, 6 months, 7 months, 8 months, 9 months, 10 months, 11 months, a year, 2 years, or 3 years. In some embodiments, the pharmaceutical composition is administered from about 2 days to 3 years, 3 days to 2 years, 5 days to a year, 7 days to 11 months, 10 days to 10 months, 15 days to 9 months, 20 days to 8 months, 30 days to 7 months, 50 days to 6 months, 60 days to 5 months, 80 days to 4 months, or 90 days to 3 years.

In some embodiments, the composition is a cosmetic composition. In some embodiments, the cosmetic composition further comprises at least one additive selected from the group consisting of cosmetically acceptable carriers, excipients, adjuvants, diluents, and combinations thereof, in order to achieve a close approximation to commercially available product forms. The composition may be formulated as a liquid solution. The cosmetic composition disclosed herein may be formulated in any suitable physical form. For example, in some embodiments, the suitable physical forms include, but not limited to, toner, emulsion, cream, gel, conditioner, soap, serum, spray, liquids with low to moderate viscosity, lotions, milks, mousses, oil, and the like.

EXAMPLES

The invention now being generally described, it will be more readily understood by reference to the following examples which are included merely for purposes of illustration of certain aspects and embodiments of the present invention, and are not intended to limit the invention in any way.

Example 1: Assay of Human Dermal Fibroblast Cells (hDFC) Proliferation

The ability of a compound or salt of the present disclosure to increase proliferation of human dermal fibroblasts was tested using a cell viability assay, such as the Promega CellTiter-Glo® Luminescent Cell Viability Assay, MTT cell proliferation assay (ATCC® 30-1010K) or manual cell counting. In some cases, the Promega CellTiter-Glo® and manual cell counting were used.

The compound or salt was added at different concentrations spanning at least a 2-log range. Fibroblasts were cultured on tissue culture-treated plastic using predefined growth media (i.e., fibroblast growth media; Promocell) containing basic fibroblast growth factor (FGFβ). In Table 14, "Activity" refers to Percent Increase Proliferation of hFDPCs (%). For the activity, "A" represents increased proliferation of hFDPCs of less than 1%, "B" represents increased proliferation of hFDPCs equals to or larger than 1% and less than 4%, "C" represents increased proliferation of hFDPCs equals to or larger than 4% and less than 8%, and "D" represents increased proliferation of hFDPCs equals to or larger than 8%.

TABLE 14

Evaluation of small molecules based on hDFCs proliferation

| ID | Chemical Name | Activity |
|---|---|---|
| I-1 | 1-(azepan-1-yl)-2-[(4-methyl-5-phenyl-1,2,4-triazol-3-yl)sulfanyl]ethanone | C |
| I-2 | 2-[(4-amino-5-phenyl-1,2,4-triazol-3-yl)sulfanyl]-1-piperidin-1-ylethanone | B |
| I-3 | 2-[[4-amino-5-(4-methylphenyl)-1,2,4-triazol-3-yl]sulfanyl]-1-pyrrolidin-1-ylethanone | C |
| I-4 | 2-[(4-amino-5-cyclohexyl-1,2,4-triazol-3-yl)sulfanyl]-1-pyrrolidin-1-ylethanone | C |
| I-5 | 1-(azepan-1-yl)-2-[(4-ethyl-5-pyridin-4-yl-1,2,4-triazol-3-yl)sulfanyl]ethanone | C |
| I-6 | 1-piperidin-1-yl-2-[(4-prop-2-enyl-5-pyridin-4-yl-1,2,4-triazol-3-yl)sulfanyl]ethanone | C |
| I-7 | 2-[(4-methyl-5-phenyl-1,2,4-triazol-3-yl)sulfanyl]-1-piperidin-1-ylethanone | B |
| II-1 | N-[2-(4-methoxyphenyl)ethyl]pentanamide | C |
| II-2 | N-[(4-methoxyphenyl)methyl]butanamide | B |
| II-3 | 2-(diethylamino)-N-(1-phenylethyl)acetamide | A |
| II-4 | N-(1-phenylethyl)propanamide | C |
| II-5 | 3-methyl-N-(1-phenylethyl)butanamide | D |

TABLE 14-continued

| Evaluation of small molecules based on hDFCs proliferation | | |
|---|---|---|
| ID | Chemical Name | Activity |
| II-6 | N-[3-(4-methoxyphenyl)propyl]-2-methylpropanamide | C |
| III-1 | N-(3-imidazol-1-ylpropyl)-N'-(4-methoxyphenyl)oxamide | D |
| III-2 | N-(3-imidazol-1-ylpropyl)-N'-[(4-methoxyphenyl)methyl]oxamide | D |
| III-3 | N-[(4-methoxyphenyl)methyl]-N'-(1-phenylethyl)oxamide | B |
| III-4 | N,N'-bis(1-phenylethyl)oxamide | B |
| III-5 | N-[1-(1-imidazol-1-ylpropan-2-ylamino)-3-methyl-1-oxobutan-2-yl]-4-methoxybenzamide | B |
| IV-1 | 2,3-dimethyl-N-(oxolan-2-ylmethyl)-1H-indole-5-carboxamide | C |
| IV-2 | [2-(dimethylamino)-2-oxoethyl] 6,7,8,9-tetrahydro-5H-carbazole-3-carboxylate | B |
| IV-3 | N-(2-methoxyethyl)-6,7,8,9-tetrahydro-5H-carbazole-3-carboxamide | D |
| IV-4 | N-(2-hydroxypropyl)-6,7,8,9-tetrahydro-5H-carbazole-3-carboxamide | C |
| IV-5 | 2-[4-(2,3,4,9-tetrahydro-1H-carbazole-1-carbonylamino)piperidin-1-yl]acetic acid | D |
| IV-6 | 2-(6,7,8,9-tetrahydro-5H-carbazole-3-carbonylamino)acetic acid | B |
| V-1 | 3-(3-ethoxypropyl)-1H-quinazoline-2,4-dione | C |
| V-2 | 3-[3-(dimethylamino)propyl]-1H-quinazoline-2,4-dione | A |
| V-3 | 3-[2-(dimethylamino)ethyl]-1H-quinazoline-2,4-dione | A |
| V-4 | methyl 2-(2,4-dioxo-1H-quinazolin-3-yl)acetate | A |
| V-5 | 3-[3-(2-methoxyethoxy)propyl]-1H-quinazoline-2,4-dione | D |
| VI-1 | N-[2-oxo-2-(1-phenylethylamino)ethyl]thiophene-2-carboxamide | D |
| VI-2 | 3-methyl-N-propan-2-ylthiophene-2-carboxamide | B |
| VI-3 | 3-methoxy-N-[4-methyl-1-(methylamino)-1-oxopentan-2-yl]thiophene-2-carboxamide | D |
| VII-1 | 4-ethyl-2,5,5-trimethyl-1,2,4-triazolidine-3-thione | D |
| VII-2 | piperazin-1-amine | D |
| VII-3 | 4-aminothiolan-3-ol | D |
| VII-4 | 1,3,5-triazatricyclo[3.3.1.13,7]decan-7-amine | D |
| VII-5 | 3,5,5-trimethyl-4H-pyrazole-1-carbaldehyde | D |
| VII-6 | diethoxymethoxyethane | D |
| VII-7 | (5S,6R)-2,8-diazaspiro[5.5]undecan-5-ol | D |
| VII-8 | 2-methylpiperazine | D |
| VII-9 | 2-methyl-1,2,6-thiadiazinane 1,1-dioxide | D |
| VII-10 | piperidin-4-one | C |
| VII-11 | N,N,N',N'-tetramethylmethanediamine | D |
| VII-12 | 1-(azepan-1-yl)-2-(4-bromo-5-methyl-3-nitropyrazol-1-yl)ethanone | C |
| VII-13 | oxetan-3-amine | D |
| VII-14 | 2,4,6-trimethoxypyrimidine | B |
| VII-15 | 1-(1-methyltetrazol-5-yl)ethanamine | D |
| VII-16 | 1-[[2-(dimethylamino)phenyl]methyl]piperidine-2-carboxylic acid | D |
| VII-17 | 2,2,5,5-tetramethylpyrrolidine-3-carboxamide | D |
| VII-18 | 2,3,4,5-tetrahydro-1H-1-benzazepine-2-carboxamide | D |
| VII-19 | 3-(4,6-dimethylpyrimidin-2-yl)sulfanyl-N-ethylpropanamide | C |
| VII-20 | N-[1-[2-(dimethylamino)phenyl]methyl]piperidin-4-yl]acetamide | D |
| VII-21 | N-(2-carbamoylcyclohexyl)-5-chloropyridine-2-carboxamide | D |
| VII-22 | 2-[1-[(2-methoxyphenyl)methyl]-3-oxopiperazin-2-yl]-N,N-dimethylacetamide | D |
| VII-23 | [4-[[2-(dimethylamino)phenyl]methyl]piperazin-1-yl]-morpholin-4-ylmethanone | D |
| VII-24 | 3-ethyl-2-hydrazinylquinazolin-4-one | D |
| VII-25 | 2-(4-methoxyphenoxy)-N-[3-oxo-3-(propylamino)propyl]propanamide | B |
| VII-26 | 2-[4-[methyl(methylsulfonyl)amino]methyl]phenoxy]-N-(1-phenylethyl)acetamide | D |
| VII-27 | 4-propan-2-yl-1,2,4-triazole | D |
| VII-28 | (2-imidazol-1-yl-1-phenylethyl) acetate | A |
| VII-29 | 1-imidazol-1-ylbutan-2-amine | A |
| VII-30 | 1-(2,2-diethoxyethyl)imidazole | D |
| VII-31 | 3-(1-imidazol-1-ylpropan-2-yl)-1-(2-methoxyethyl)-1-(3-phenylpropyl)urea | A |
| VII-32 | 4-(3-imidazol-1-ylpropanoyl)-1-[(4-methoxyphenyl)methyl]piperazin-2-one | A |
| VII-33 | 2-imidazol-1-yl-1-[4-[(4-methoxyphenyl)methyl]piperazin-1-yl]ethanone | C |
| VII-34 | 2-[3-(4-methoxyphenyl)propyl]-1H-benzimidazole | D |
| VII-35 | 2-[[5-(2-oxo-2-pyrrolidin-1-ylethyl)sulfanyl-1,3,4-thiadiazol-2-yl]sulfanyl]-1-pyrrolidin-1-ylethanone | C |
| VII-36 | 2-[1-(4-hydroxyphenyl)tetrazol-5-yl]sulfanyl-1-piperidin-1-ylethanone | D |
| VII-37 | 2-(1-methyltetrazol-5-yl)sulfanyl-1-piperidin-1-ylethanone | C |
| VII-38 | 1-[(4S)-1-[[2-(dimethylamino)phenyl]methyl]-4-methoxypyrrolidin-3-yl]-3-ethylurea | D |
| | Retinol | B |

*Control is DMSO.

Example 2: Assay on Human Dermal Microvascular Endothelial Cells (HDMEC)

The ability of a compound or salt of the present disclosure to impact proliferation of human adult dermal microvascular endothelial cells was tested using a cell viability assay, such as Promega CellTiter-Glo® Luminescent Cell Viability Assay, MTT cell proliferation assay (ATCC® 30-1010K) or cell counting after 48 hr. The compound or salt was added at different concentrations spanning at least a 2-log range.

Example 3: Assay on Keratinocytes

Human adult epidermal keratinocytes were cultured on poly-L-lysine treated plates and the ability of a compound or salt of the present disclosure to impact proliferation was measured using a cell viability assay, such as Promega CellTiter-Glo® Luminescent Cell Viability Assay, MTT cell proliferation assay (ATCC® 30-1010K) or cell counting after 48 hr. The compound or salt was added at different concentrations spanning at least a 2-log range.

Example 4: Assay on Primary Epidermal Melanocytes; Normal, Human, Adult (HEMa)

The ability of a compound or salt of the present disclosure to impact proliferation of human adult epidermal melanocytes was tested using a cell viability assay, such as Promega CellTiter-Glo® Luminescent Cell Viability Assay, MTT cell proliferation assay (ATCC® 30-1010K) or cell counting after 48 hr. The compound or salt was added at different concentrations spanning at least a 2-log range. Melanocytes derived from at least two different donors of varying degrees of basal skin pigmentation were used.

Example 5: In Silico Safety/Toxicology Studies

The in silico safety/toxicology profiles of compounds were determined by screening chemical structures against a series of computational models. These include the Pred-hERG 4.2 cardiotoxicity model and the NeuroDeRisk IL Profiler neurotoxicity model, as well as reproductive and developmental toxicity, carcinogenicity (genotoxic and non-genotoxic), skin sensitization, DNA mutation, and chromosomal aberration models from QSAR Toolbox.

Example 6: Safety/Toxicology Studies

The safety/toxicology profiles of a compound or salt of the present disclosure was evaluated via a series of in vitro genotoxicity assays, including the SOS-chromotest to determine bacterial genotoxicity, and the TK.6 micronucleus assay to determine chromosomal damage and forward mutations. Standard reactive oxygen species (ROS) and caspase 3/7 assay were conducted to determine general cellular toxicity. Moreover, a series of sensitization tests were conducted to predict any potential skin sensitivity. These include the direct peptide reactivity assay to evaluate haptenization, the KeratinoSens reporter assay to determine any potential sensitivity via the activation of a cytoprotective pathway, and an immunological assay using human immature monocyte-derived dendritic cells to evaluate any potential immunogenicity.

Figure 5A:
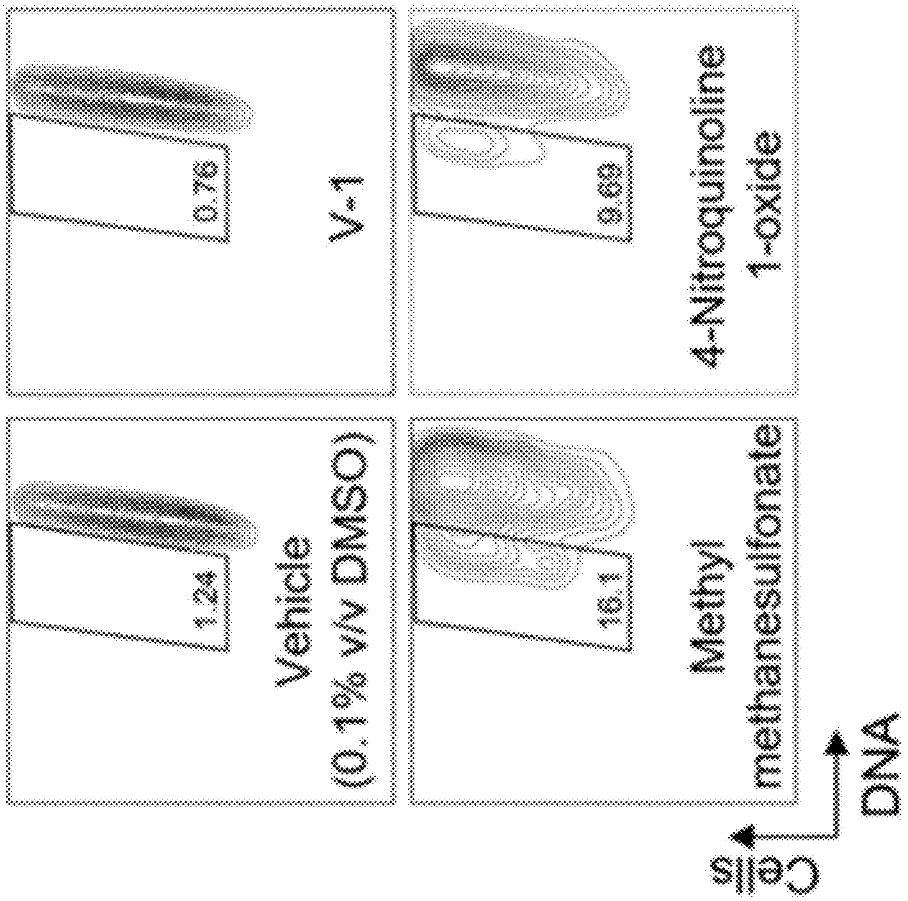
FIG. 5A-FIG. 5E show example compounds exhibiting no genotoxic transformation potential.
Figure 5B:
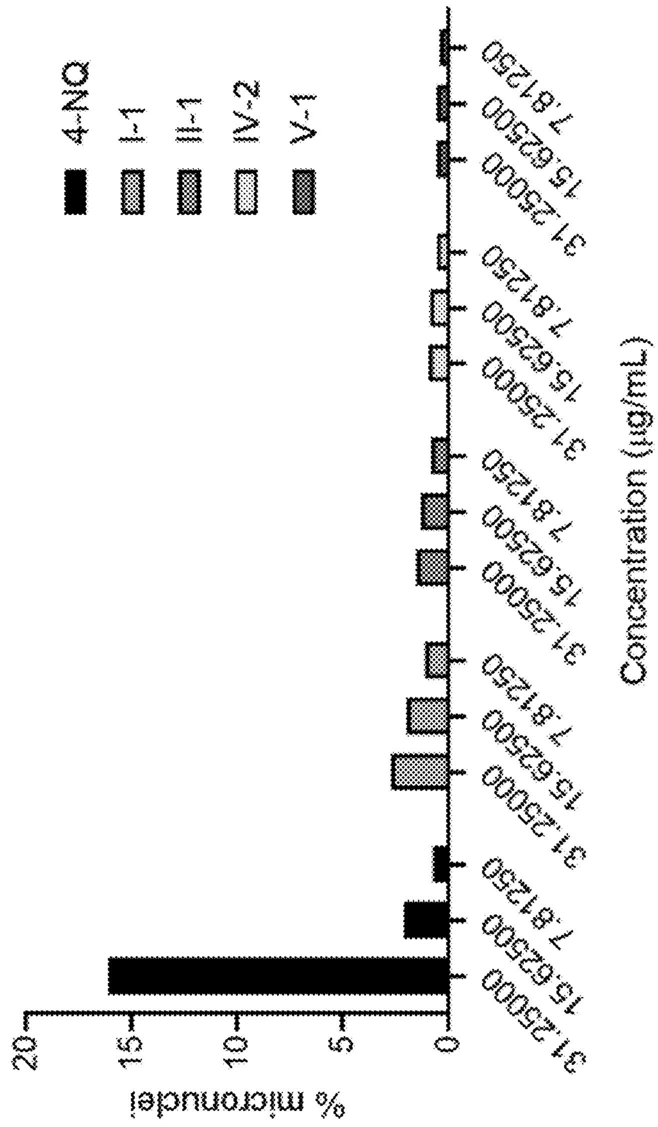
Figure 5C:
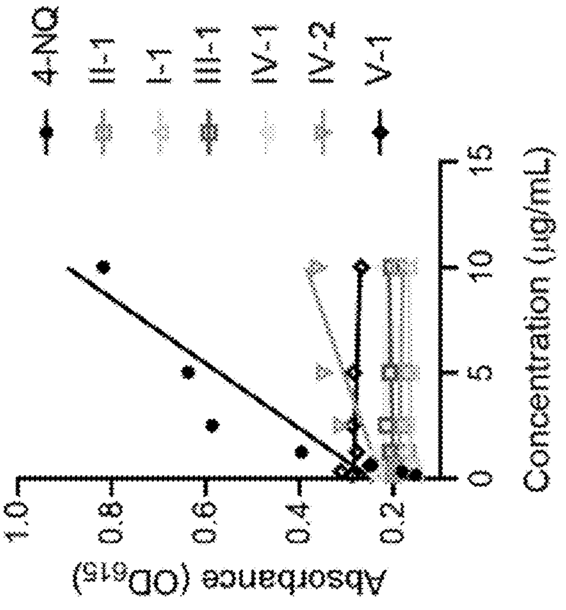
Figure 5D:
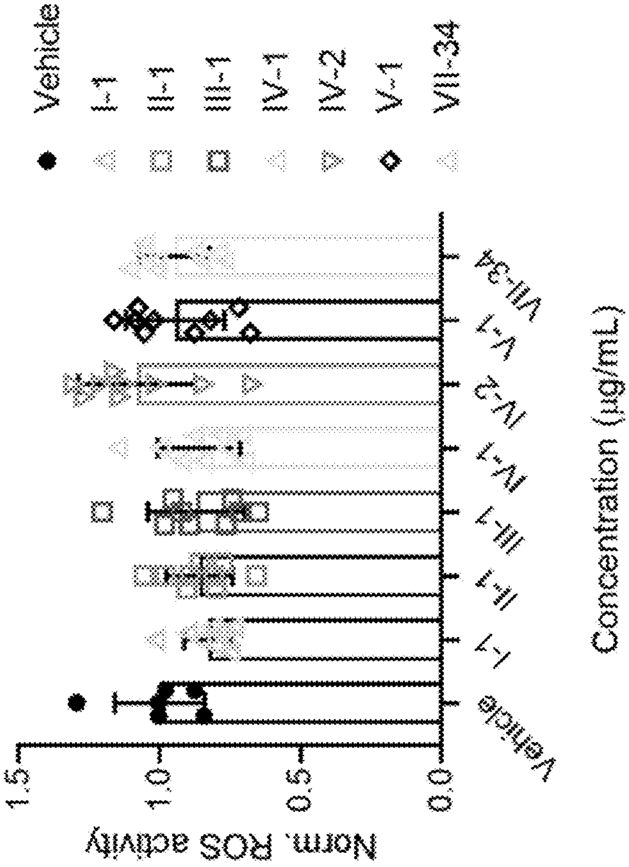
Figure 5E:
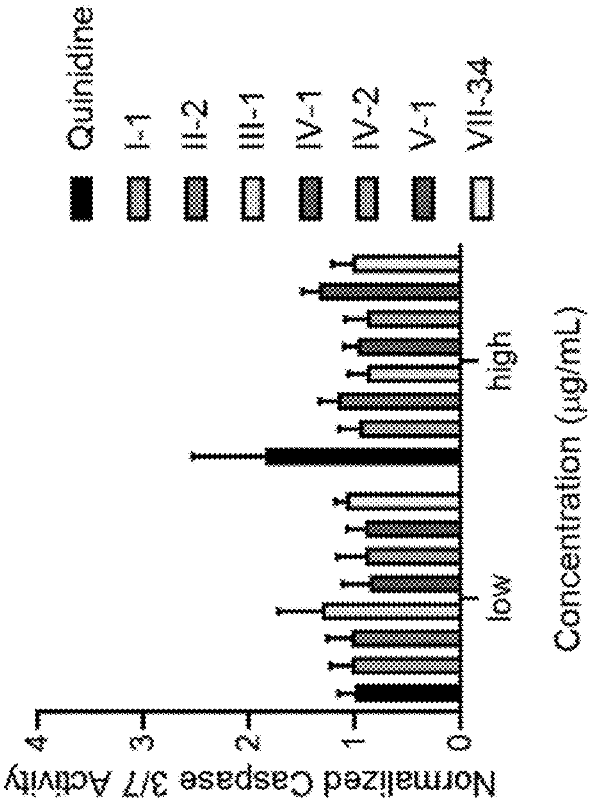

Example compounds exhibited no genotoxic transformation potential (FIG. 5A-FIG. 5E). TK.6 lymphoblasts are a cell line used for gene mutation analyses. TK.6 lymphoblasts are heterozygous for the thymidine kinase gene (TK) and enable the detection of forward mutations and chromosomal damage, which manifests as micronuclei. TK.6 lymphoblasts are detectable via flow cytometry. TK.6 cells were dosed with the compounds or a vehicle control (0.1% v/v DMSO) and cultured without S9 metabolic activation for 24 hr. FIG. 5A-FIG. 5E show the results of in vitro genotoxicity assay and the TK.6 micronucleus assay. FIG. 5A are example plots of TK.6 cells treated with compound V-1. Methyl methanesulfonate, a genotoxic, alkylating agent was used as a positive control for micronuclei detection. FIG. 5B shows quantification of TK.6 micronuclei assay following treatment with various compounds across a concentration range. FIG. 5C shows normalized β-galactosidase activity (as quantified via absorbance) from the SOS chromotest using a genotoxin (4-NQ; 4-nitroquinoline-1-oxide) and example compounds at varying concentrations. The SOS chromotest is a bacteria-based test for genotoxicity. The results of FIG. 5B and FIG. 5C show that the example compound V-1 did not exhibit any genotoxic transformation potential, while compounds IV-2, I-1, II-1, III-1, and IV-1 exhibited mild genotoxicity at higher concentrations. FIG. 5D shows normalized reactive oxygen species (ROS) activity in human dermal papilla cells treated with 5 g/mL example compounds relative to vehicle control (0.1% v/v DMSO) after 24 hr. All tested example compounds induced minimal or no changes in ROS activity compared to baseline vehicle control. FIG. 5E displays normalized caspase 3/7 activity in HepG2 cells, an immortalized liver cell line used for studying apoptosis induced by small molecules. Cells were treated with either the compounds or vehicle control containing correspondingly % v/v-matched amounts of DMSO. High represents 10 g/mL while low represents 1 μg/mL. Tested compounds elicited no or minor caspase 3/7 activation at low and high concentrations. In FIG. 5A-FIG. 5E, data represents mean±s.d. and representative of at least 2 experimental replicates.

Future studies will include mechanism-oriented studies, including metabolism and transport studies focusing on the ability of a compound or salt of the present disclosure to induce or inhibit cytochrome P450, passive/active transport using the Caco-2 cell line, a well-established compound transport assay. Additional safety and toxicity studies include functional cardiotoxicity and neurotoxicity in human iPSC-derived cardiomyocytes and neurons, respectively. Finally, a repeated insult patch test will be performed using a compound or salt of the present disclosure on 200 human subjects to predict any potential induced allergic contact dermatitis and associated responses.

Example 7: Skin Sensitizing Potential or Immunogenicity

Figure 6A:
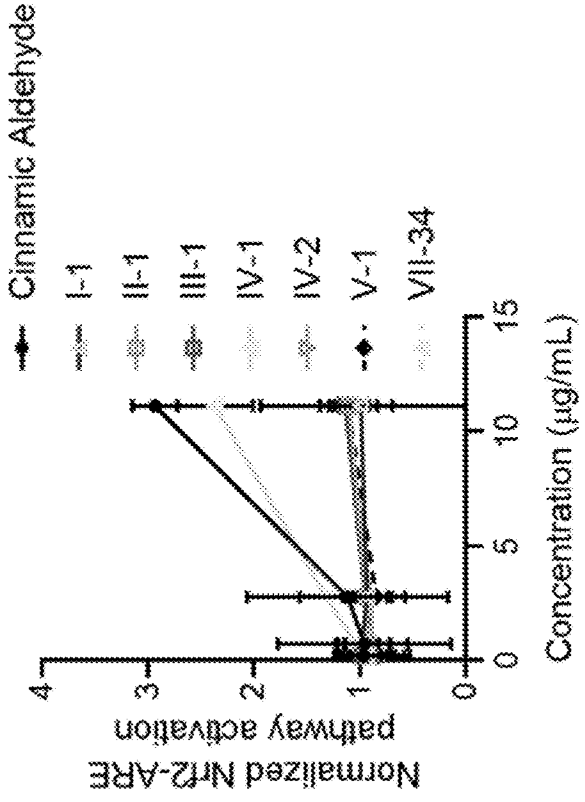
FIG. 6A-FIG. 6E show example compounds that do not exhibit any skin sensitizing potential or immunogenicity.
Figure 6B:
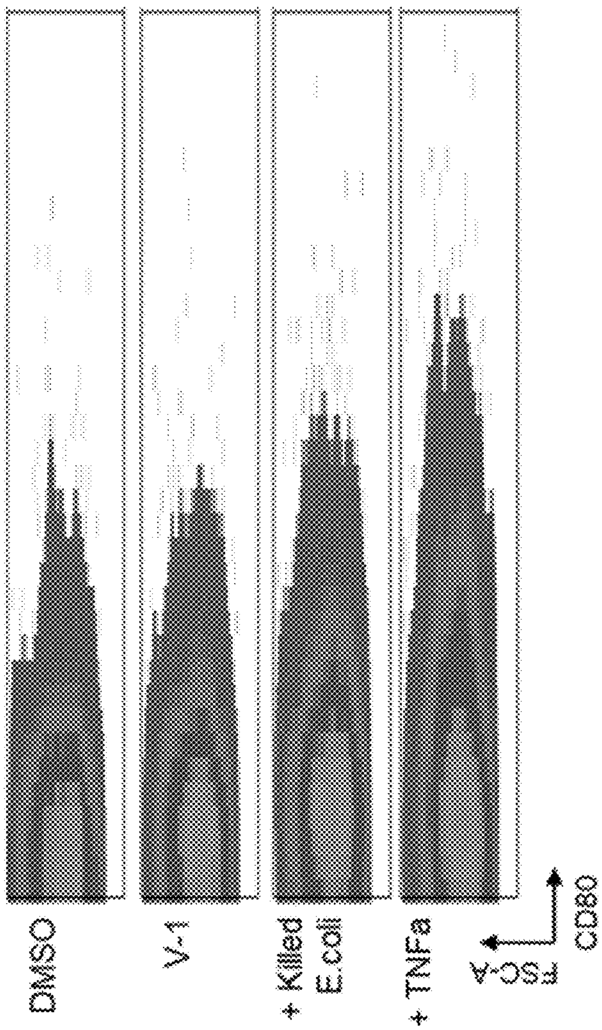
Figure 6C:
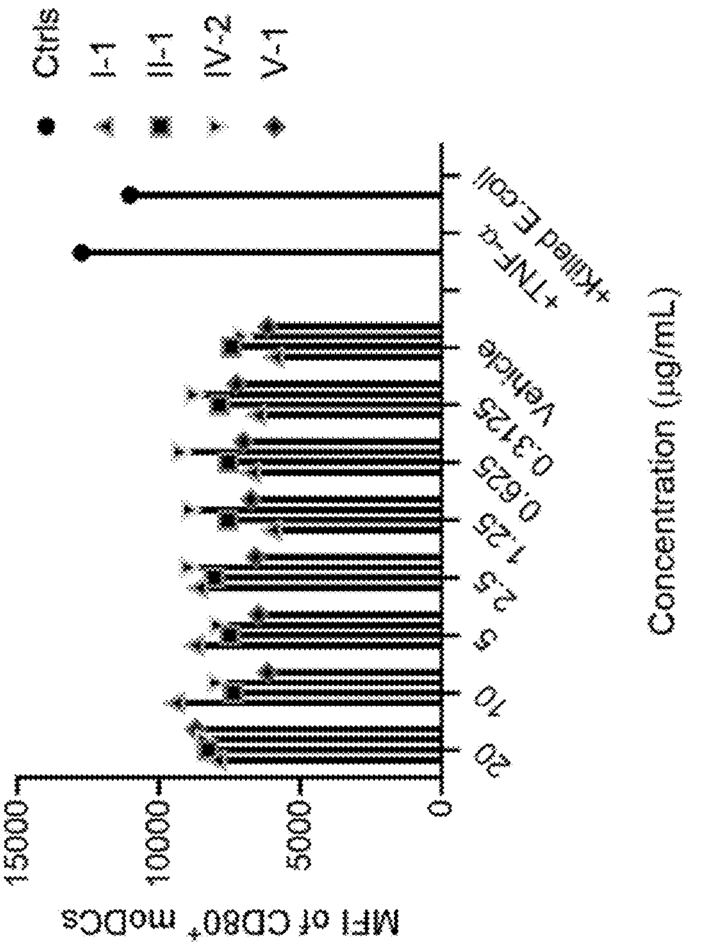
Figure 6D:
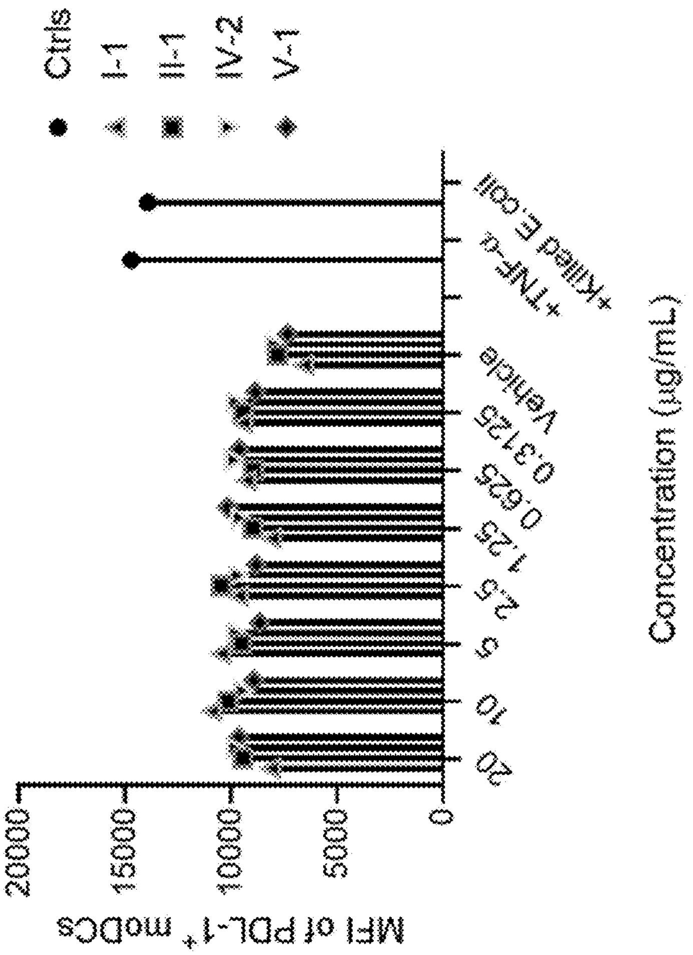
Figure 6E:
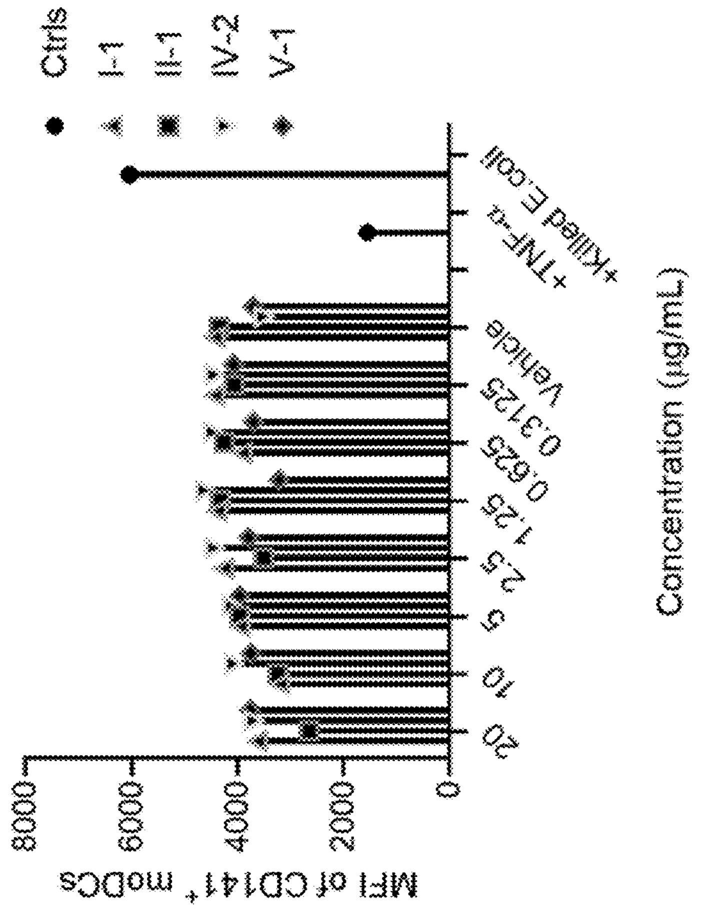

Example compounds do not exhibit any skin sensitizing potential or immunogenicity (FIG. 6A-FIG. 6E). The Nrf2-ARE pathway is a master regulator of cytoprotective responses to oxidative stress, and is an early indicator of skin sensitization. Nrf2 (nuclear factor erythroid 2-related factor) is a transcription factor that binds to antioxidant responsive elements (ARE). By fusing ARE to the light-producing luciferase gene, a KeratinoSens Nrf2-ARE reporter assay was constructed whereby luciferase signal is directly correlated to Nrf2-ARE pathway activation. FIG. 6A shows normalized ARE-luciferase activity using a sensitizing compound (cinnamic aldehyde) and example compounds across a concentration range. Compound IV-1 exhibited sensitizing potential, while compounds I-1, II-1, III-1, IV-2, V-1, and VII-34 did not exhibit apparent Nrf2-ARE pathway activation. FIG. 6B describes an in vitro dendritic cell sensitization test. Dendritic cell activation is widely-associated with downstream immunogenicity. CD14+ cells from human donor peripheral mononuclear cells were harvested and differentiated them into immature monocyte-derived DCs using granulocyte-macrophage colony-stimulating factor (GM-CSF) and interleukin-4 (IL-4), then treated with the lead compounds. Killed *E. Coli* and TNF-α were used as positive controls. FIG. 6C-FIG. 6E are example plots showing change in HLA-DR expression. Expression of CD80 (FIG. 6C), PDL-1 (FIG. 6D), and CD141 (FIG. 6E) as quantified via mean fluorescence intensity (MFI) following dosing with example compounds. FIG. 6C-FIG. 6E show that none of the example compounds exhibit any mo-DC activation potential. In FIG. 6A-FIG. 6E, data represents mean±s.d. and representative of at least 2 experimental replicates.

Example 8: Clinical Studies

Clinical test was performed by Eurofins|CRL, Inc. The test followed the established, standardized procedures for clinical testing that has been designed to ensure the well-being of clinical study subjects and the generation of reliable study data. A total of 120 male and female subjects, ranging in age from 18 to 70 years old, were selected for study participation. The objective of the study was to determine the potential of the test material containing 0.01% v/v of compound V-1 (in formulation) to elicit dermal irritation and/or induce sensitization following repeated patch applications.

TABLE 15

Clinical repeat insult patch test using compound V-1

| Subjects Completed | Gender | Patch | Adverse reactions |
|---|---|---|---|
| 105/120 (11 subjects lost during follow-up, 4 subjects discontinued for personal reasons) | 26 males and 79 females | Occlusive | 0/105 (0%)* |

Clinical consumer perception study was performed using compound V-1. A third cell (Cell3) was conducted to test general formulation compatibility and irritability of both compound V-1 and a low-dose of retinol in formulation. As reported, there were 0 adverse effects in all cells, including Cell3. The test results are shown in Table 16.

TABLE 16

Clinical consumer perception study using compound V-1

| Study Design | | | Questions | | | Cutometer | |
|---|---|---|---|---|---|---|---|
| Cell | Adverse effects | Blinding | I enjoyed the results of the product so far (4 weeks) | The product made my skin feel hydrated | The side effects from the product are more tolerable and miler than other treatments I've used | Skin elasticity measurement at 8 weeks | |
| Cell1 (0.5% retinol) | 0/43 (0%)* | Subjects were blinded to the name of the test material | 69.23% | 53.85% | 53.85% | Mean Percent Difference from Baseline | 11.55% (p = 0.037) |
| | | | | | | Percent of Subjects Improved | 69.23% (NS) |
| Cell2 (formula containing V-1) | | | 78.57% | 78.57% | 71.43% | Mean Percent Difference from Baseline | 20.58% (p = 0.031) |
| | | | | | | Percent of Subjects Improved | 92.86% (p = 0.012) |

Figure 7:
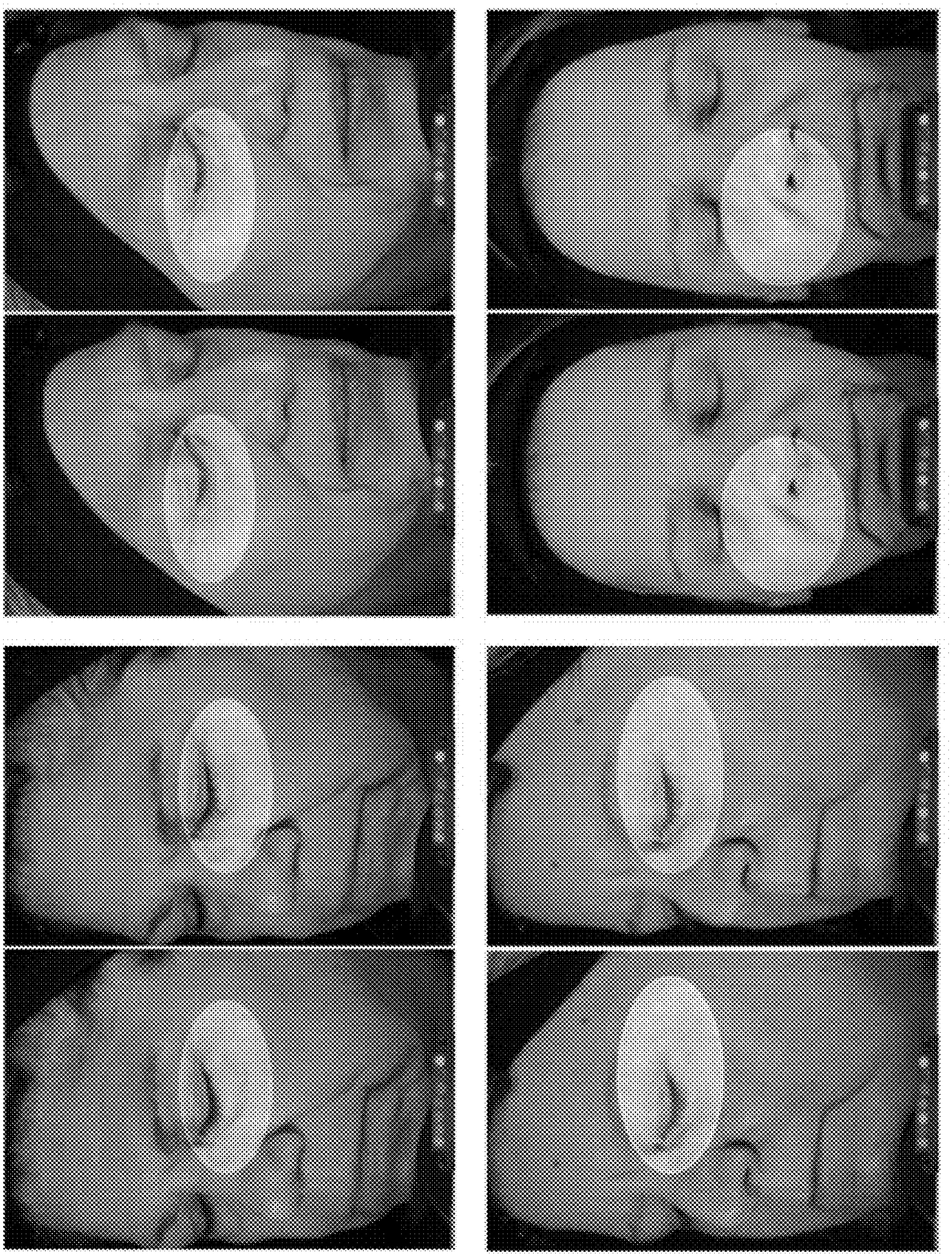
FIG. 7 shows example photographs of subjects in a clinical study.

Photographs were taken using a Canfield Visia-CR system after 8 weeks (FIG. 7). Subjects were female and ranged in age from 51-70 years. A simple, water-based formula containing the example compound V-1 (at 0.5% w/v) was used. Subjects were instructed to apply the formula 1-2 times a day after cleansing with Cetaphil's Daily Cleanser. Sunscreen application was requested (Neutrogena Oil Free Moisture with SPF 35) and direct sun avoidance was encouraged. No randomization was required for the study and subjects were blinded to the name of the test material. Based on cutometer readings, subjects using the formula containing compound V-1 exhibited a 2-fold improvement in skin elasticity versus the gold-standard 0.5% retinol formula. Subjects also reported fewer side effects relatively compared to the 0.5% retinol.

A total of 43 healthy female subjects consented, enrolled, and completed the clinical study. In Table 17, Cell 1 represents the cohort of participants that used a gold-standard 0.5% retinol formula. Cell 2 represents the cohort of participants that used a simple, water-based formula containing the example compound V-1 (at 0.5% w/v). Cell 3 represents the cohort of participants that used a combination formula of example compound V-1 and a low-dose retinol (0.3% retinol).

TABLE 17

Subject demographics of clinical consumer perception study using compound V-1

| No. | Subject ID | Age | Treatment |
|---|---|---|---|
| 1 | 001 | 68 | Cell 2 |
| 2 | 002 | 65 | Cell 3 |
| 3 | 003 | 68 | Cell 1 |
| 4 | 004 | 63 | Cell 1 |
| 5 | 005 | 61 | Cell 3 |
| 6 | 006 | 62 | Cell 1 |
| 7 | 007 | 68 | Cell 3 |
| 8 | 008 | 65 | Cell 3 |
| 9 | 009 | 69 | Cell 3 |
| 10 | 010 | 54 | Cell 3 |
| 11 | 011 | 63 | Cell 1 |
| 12 | 012 | 67 | Cell 2 |
| 13 | 013 | 63 | Cell 2 |
| 14 | 014 | 66 | Cell 3 |
| 15 | 015 | 70 | Cell 3 |
| 16 | 016 | 64 | Cell 2 |
| 17 | 017 | 65 | Cell 2 |
| 18 | 018 | 53 | Cell 1 |
| 19 | 019 | 55 | Cell 3 |
| 20 | 021 | 70 | Cell 3 |
| 21 | 022 | 59 | Cell 2 |
| 22 | 023 | 67 | Cell 2 |
| 23 | 024 | 70 | Cell 3 |
| 24 | 025 | 58 | Cell 1 |
| 25 | 026 | 62 | Cell 2 |
| 26 | 027 | 69 | Cell 3 |
| 27 | 028 | 68 | Cell 1 |
| 28 | 029 | 67 | Cell 3 |
| 29 | 030 | 63 | Cell 1 |
| 30 | 031 | 61 | Cell 2 |
| 31 | 032 | 64 | Cell 1 |
| 32 | 033 | 65 | Cell 3 |
| 33 | 034 | 67 | Cell 2 |
| 34 | 035 | 69 | Cell 2 |
| 35 | 036 | 63 | Cell 2 |
| 36 | 037 | 57 | Cell 1 |
| 37 | 038 | 51 | Cell 1 |
| 38 | 039 | 61 | Cell 3 |
| 39 | 040 | 67 | Cell 1 |
| 40 | 041 | 63 | Cell 2 |
| 41 | 042 | 69 | Cell 2 |
| 42 | 043 | 54 | Cell 1 |
| 43 | 045 | 56 | Cell 3 |

Example 9: Efficacy Studies

The functional profile of a compound or salt of the present disclosure continues to be investigated in a number of ex vivo models and observational clinical trials. Additionally, transcriptomic and proteomic analyses will be conducted on relevant genes and proteins with well-established functional roles such as collagen on cells exposed to a compound or salt of the present disclosure. A compound or salt of the present disclosure will be treated on excised live human skin grafts from cosmetic surgeries to evaluate the targeted activation of human dermal fibroblasts in histology studies. Additional mechanical testing, including stiffness and viscoelasticity measurements, will be performed to further evaluate the functional benefit of a compound of salt of the present disclosure. Finally, a clinical efficacy trial will be performed with at least 30 human subjects to determine effectiveness of a compound or salt of the present disclosure to improve the appearance of skin tightening. Additional trials with more subjects and spanning wider age groups and demographics may follow.

Example 10: Mechanistic Analysis

Using the transcriptomics dataset, a series of mechanistic computational analyses will be performed to identify possible mechanisms of action. These may include DE analyses followed by GO term and pathway enrichment to characterize the biological imprint of our lead chemicals. In addition, we will perform pseudo-time and cell-cycle analyses to probe the developmental effects of these chemicals on target cells. We may validate the extracted insight in further investigations using various models.

Example 11: Synthesis of Compound V-1

Sheme 1

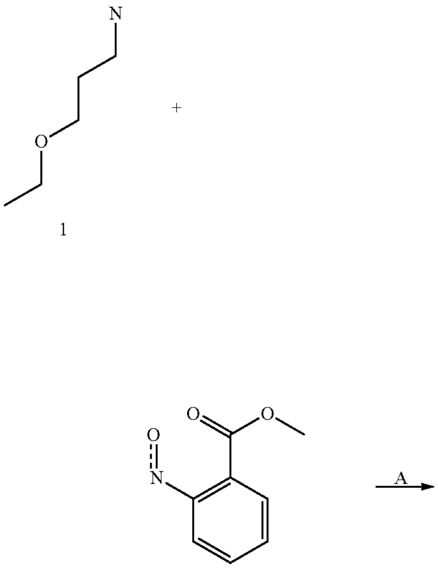

1

2

-continued

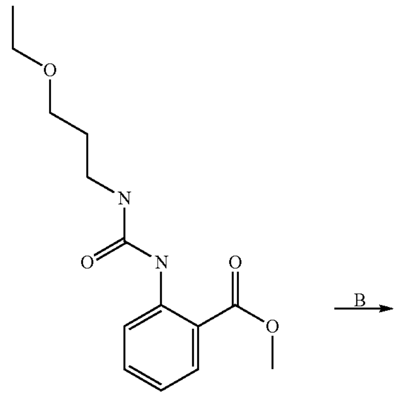

3

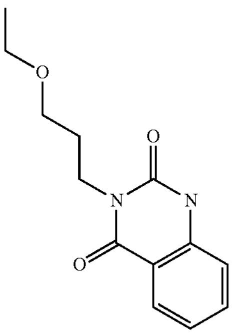

Step A: Compound 1 (20 g, 0.2 mol) was dissolved in 150 ml of dichloromethane, and compound 2 (34.3 g, 0.2 mol) was added. The mixture was vigorously shaken for 12 hours. The solvent was evaporated in vacuo. 150 ml of n-hexane was added to the remaining solid and the mixture was vigorously shaken for 20 min. The solvent was decanted from the solid residue, and the solid was dried in vacuo. Yield: 43 g.

Step B: To a solution of compound 3 (43 g, 0.15 mol) in MeOH (155 ml) at room temperature was added an aqueous solution of 1 M KOH (2 eq)). The reaction mixture was refluxed until complete consumption of the starting materials as monitored by Liquid Chromatography Mass Spectrometry (LCMS). The aqueous layer was washed with $CH_2Cl_2$ (300 ml), then acidified with conc HCl to pH 2 to obtain a solid precipitate, which was collected by filtration. The precipitate was thoroughly washed with water (3×100 ml) to afford the product. Yield is 32 g.

Example 12: Synthesis of Compound IV-2

Scheme 2

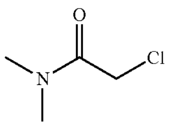

\+

1

-continued

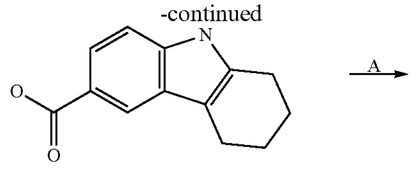

2

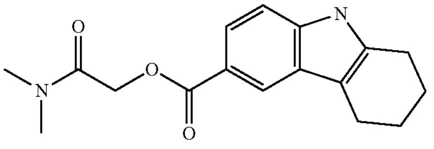

Step A: Compound 2 (20 g, 0.1 mol) was dissolved in 150 ml of acetonitrile and $NaHCO_3$ (0.2 mol) was added. The mixture was stirred for 30 min at room temperature and compound 1 (12.4 g, 0.11 mol) was added. The reaction mixture was stirred at room temperature for 12 h (Thin Layer Chromatography and LCMS control), solvent was evaporated in vacuo and 150 ml of water was added at 10° C. The precipitate was filtered, washed with cold water (3×100 ml) and dried in vacuo for 10 h. Yield is 9.8 g.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for treating a skin condition, disorder, or disease, the method comprising administering to a subject in need thereof a composition comprising a compound having a structure of Formula (V):

(V)

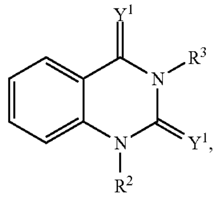

or a salt thereof, wherein:

$Y^1$ is O or $NR^1$, wherein $R^1$ is H, alkyl, or haloalkyl;

$R^2$ is selected from H, alkyl, haloalkyl, alkenyl, haloalkenyl, aryl, and aralkyl; and $R^3$ is selected from H, alkyl, haloalkyl, $-(CH_2)_{m1}-OR^{a1}$, $-(CH_2)_{m2}-O-(CH_2)_{m3}-OR^{a2}$, $(CH_2)_{m5}-C(O)OR^c$, wherein:

$R^{a1}$, $R^{a2}$, and $R^c$ are each independently selected from H, alkyl, and haloalkyl; and m1, m2, m3, and m5 are each independently selected from 1, 2, 3, and 4.

2. The method of claim 1, wherein $Y^1$ is O.

3. The method of claim 1, wherein $R^{a1}$, $R^{a2}$, and $R^c$ are each independently $C_1$-$C_6$ alkyl.

4. The method of claim 1, wherein $R^{a1}$, $R^{a2}$, and $R^c$ are each independently $C_1$-$C_3$ alkyl.

5. The method of claim 4, wherein $R^{a1}$, $R^{a2}$, and $R^c$ are each independently $C_1$ alkyl or $C_2$ alkyl.

6. The method of claim 1, wherein m1, m2, and m3 are each independently 2 or 3.

7. The method of claim 1, wherein m5 is 1.

8. The method of claim 1, wherein $R^2$ is H.

9. The method of claim 1, wherein the compound of Formula (V) is selected from the group consisting of:

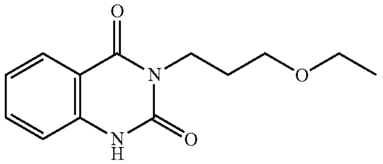
,

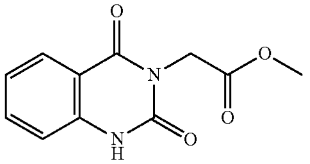
,

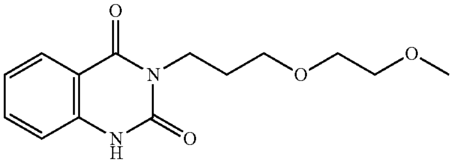
, and a salt thereof.

10. The method of claim 1, wherein the subject has been diagnosed with the skin condition, disorder, or disease.

11. The method of claim 1, wherein the subject has not been diagnosed with the skin condition, disorder, or disease.

12. The method of claim 1, wherein the composition is a pharmaceutical composition comprising a pharmaceutically acceptable additive selected from the group consisting of a carrier, an excipient, an adjuvant, and a diluent.

13. The method of claim 1, wherein the composition is a cosmetic composition comprising an additive selected from the group consisting of a carrier, an excipient, an adjuvant, and a diluent.

14. The method of claim 1, wherein the composition is formulated as a toner, cream, emulsion, lotion, ointment, paste, gel, suspension, serum, oil, spray, milk, mousse, or mist.

15. The method of claim 1, wherein a site of the administration comprises a skin area comprising face skin, elbow skin, neck skin, hand skin, skin around a joint or a combination thereof.

16. The method of claim 15, wherein the face skin comprises skin of forehead, temple, malar area, nasolabial fold, marionette line, chin, mandible, midface, preauricular zone, periorbital hollow, cheek, jaw contour, lip, or a combination thereof.

17. The method of claim 1, wherein the method prevents or reduces a wrinkle or fine line of the subject.

18. The method of claim 1, wherein the method increases skin tightness of the subject or moisturizes or hydrates skin of the subject.

19. The method of claim 1, wherein the method increases skin collagen production, collagen-depositing cell proliferation, or fibroblast proliferation in the subject or in a cell of the subject.

* * * * *